(12) United States Patent
Oshiyama et al.

(10) Patent No.: US 10,862,048 B2
(45) Date of Patent: Dec. 8, 2020

(54) ORGANIC ELECTROLUMINESCENT DEVICE, THIN LUMINOUS FILM, DISPLAY APPARATUS, AND LIGHTING APPARATUS

(71) Applicant: Konica Minolta, Inc., Tokyo (JP)

(72) Inventors: Tomohiro Oshiyama, Hachioji (JP); Hiroshi Kita, Hachioji (JP); Taketo Namikawa, Osaka (JP); Michihiro Okuyama, Hino (JP); Tatsuya Hattori, Nerima-ku (JP); Yasuo Miyata, Yokohama (JP)

(73) Assignee: Merck Patent GmbH, Darmstadt (DE)

( * ) Notice: Subject to any disclaimer, the term of this patent is extended or adjusted under 35 U.S.C. 154(b) by 379 days.

(21) Appl. No.: 15/329,823

(22) PCT Filed: Jul. 30, 2015

(86) PCT No.: PCT/JP2015/071647
§ 371 (c)(1),
(2) Date: Jan. 27, 2017

(87) PCT Pub. No.: WO2016/017760
PCT Pub. Date: Feb. 4, 2016

(65) Prior Publication Data
US 2018/0212157 A1    Jul. 26, 2018

(30) Foreign Application Priority Data
Jul. 31, 2014 (JP) .................. 2014-156059

(51) Int. Cl.
*H01L 51/00* (2006.01)
*C07D 219/02* (2006.01)
(Continued)

(52) U.S. Cl.
CPC ........ *H01L 51/0072* (2013.01); *C07D 209/86* (2013.01); *C07D 219/02* (2013.01); *C07D 311/90* (2013.01); *C07D 333/76* (2013.01); *C07D 401/10* (2013.01); *C07D 403/10* (2013.01); *C07D 403/12* (2013.01); *C07D 403/14* (2013.01); *C07D 405/10* (2013.01); *C07D 409/14* (2013.01); *C07D 413/10* (2013.01); *C07D 413/14* (2013.01); *C07D 471/04* (2013.01); *C07D 471/14* (2013.01); *C07D 487/04* (2013.01); *C07D 491/22* (2013.01); *C07F 7/0812* (2013.01); *C07F 9/65685* (2013.01); *C09K 11/06* (2013.01); *H01L 51/0052* (2013.01); *H01L 51/0061* (2013.01); *H01L 51/0067* (2013.01); *H01L 51/0068* (2013.01); *H01L 51/0069* (2013.01); *H01L 51/0071* (2013.01); *H01L 51/0073* (2013.01); *H01L 51/0074* (2013.01); *H01L 51/0094* (2013.01); *H05B 33/14* (2013.01); *H05B 33/20* (2013.01); *C09K 2211/1029* (2013.01); *H01L 51/5012* (2013.01); *H01L 51/5016* (2013.01); *H01L 51/5028* (2013.01); *H01L 2251/552* (2013.01)

(58) Field of Classification Search
CPC .. C07D 403/12; C07D 413/10; C07D 487/04; C07D 498/22; C07D 491/22; C07D 471/14; C07D 471/04; C07D 413/14; C07D 409/14; C07D 405/10; C07D 403/10; C07D 401/10; C07D 333/76; C07D 311/90; C07D 219/02; C07D 209/86; C07D 403/14; C07F 9/65685; C07F 7/0812; H05B 33/20; H05B 33/14; C09K 2211/1029; C09K 11/06; C09K 2211/1044; H01L 51/5012; H01L 51/0061; H01L 51/0052; H01L 51/0072; H01L 51/0073; H01L 51/5004; H01L 51/50; H01L 51/0094; H01L 51/0074; H01L 51/0071; H01L 51/0069; H01L 51/0068; H01L 51/0067; H01L 2251/552; H01L 51/5028; H01L 51/5016
USPC .............................................. 428/690
See application file for complete search history.

(56) References Cited

U.S. PATENT DOCUMENTS 8,778,507 B2 * 7/2014 Tamura ............... C09K 11/025
257/40
8,890,126 B2   11/2014 Ryu et al.
(Continued)

FOREIGN PATENT DOCUMENTS

JP    2011213643 A    10/2011
JP    2012-099515     5/2012
(Continued)

OTHER PUBLICATIONS

Office Action issued in corresponding Korean application 10-2017-7001392 dated Dec. 19, 2018.
(Continued)

*Primary Examiner* — Douglas J Mc Ginty
(74) *Attorney, Agent, or Firm* — Lucas & Mercanti, LLP

(57) ABSTRACT

An organic electroluminescent device contains an anode, a cathode, and an organic layer containing at least one luminous layer. The organic layer is disposed between the anode and the cathode. At least one luminous layer contains a π-conjugated compound exhibiting no overlap between the electron density distributions of the HOMO and the LUMO in the molecule, such that electron transition between the HOMO and the LUMO occurs by a through-space interaction in the molecule. The π-conjugated compound has a π-conjugated aromatic ring at a moiety on which at least one of the HOMO and the LUMO is localized.

6 Claims, 10 Drawing Sheets

(51) Int. Cl.
| | |
|---|---|
| *C07D 311/90* | (2006.01) |
| *C07D 333/76* | (2006.01) |
| *C07D 401/10* | (2006.01) |
| *C07D 403/10* | (2006.01) |
| *C07D 403/12* | (2006.01) |
| *C07D 403/14* | (2006.01) |
| *C07D 405/10* | (2006.01) |
| *C07D 409/14* | (2006.01) |
| *C07D 413/10* | (2006.01) |
| *C07D 413/14* | (2006.01) |
| *C07D 471/04* | (2006.01) |
| *C07D 471/14* | (2006.01) |
| *C07D 487/04* | (2006.01) |
| *C07D 491/22* | (2006.01) |
| *C07F 7/08* | (2006.01) |
| *C07F 9/6568* | (2006.01) |
| *C09K 11/06* | (2006.01) |
| *H05B 33/14* | (2006.01) |
| *H05B 33/20* | (2006.01) |
| *C07D 209/86* | (2006.01) |
| *H01L 51/50* | (2006.01) |

(56) References Cited

U.S. PATENT DOCUMENTS

| | | | |
|---|---|---|---|
| 9,130,183 B2 * | 9/2015 | Sugita | H01L 51/5016 |
| 9,812,653 B2 | 11/2017 | Jung et al. | |
| 10,297,761 B2 * | 5/2019 | Kawamura | C09K 11/06 |
| 2012/0098413 A1 | 4/2012 | Lin | |
| 2016/0197286 A1 * | 7/2016 | Kawamura | C09K 11/06 257/40 |
| 2016/0268516 A1 * | 9/2016 | Tanaka | H01L 51/0072 |
| 2016/0372683 A1 * | 12/2016 | Tanimoto | H01L 51/0067 |

FOREIGN PATENT DOCUMENTS

| | | | |
|---|---|---|---|
| JP | 2012-153628 A | | 8/2012 |
| JP | 2013-165192 A | | 8/2013 |
| JP | 2013191804 A | * | 9/2013 |
| JP | 2014-138006 A | | 7/2014 |
| KR | 10-2010-0135815 | | 12/2010 |
| KR | 20110118542 A | | 10/2011 |
| KR | 10-2013-0139996 A | | 12/2013 |
| KR | 20150061975 A | | 6/2015 |
| WO | 2009/069442 | | 11/2007 |
| WO | 2010134350 A1 | | 11/2010 |
| WO | 2014/092083 A1 | | 6/2014 |
| WO | WO-2014097866 A1 | * | 6/2014 |

OTHER PUBLICATIONS

Office Action dated Feb. 19, 2019 from the corresponding Korean Patent Application No. 10-2017-7001392 and English translation.
Office Action issued in corresponding Korean Application KR 10-2017-7001392 dated May 28, 2018 and English translation.
Jitsuyoka Suteji o Mukaeta Yukiko Erekutoronikusu (An advanced stage of organic optoelectronics with the aim of commercialization); Oyo Buturi; vol. 82; No. 6; 2013.
H. Uoyama, et al; Nature; vol. 492; 2012; pp. 234-238.
S.Y. Lee, et al; Applied Physics Letters; vol. 101; 2012; pp. 093306-093309.
T. Nakagawa, et al; Chem. Commun., vol. 48; 2012; pp. 9580-9582.
Yuki EL Toronkai Dai-10-Kai Reikai Yokoshu (Proceedings of Japan OLED Forum, 10th Meeting); 2010; pp. 11-12.
International Search Report dated Oct. 6, 2015 for PCT/JP2015/071647 and English translation.
IPRP dated Jun. 10, 2015 from the corresponding International Application No. PCT/JP2015/071647; Applicant: Konica Minolta, Inc.; English translation of IPRP; Total of 14 pages.
KIPO, Notice of Final Rejection for the corresponding Korean Patent Application No. 10-2017-7001392, dated Aug. 22, 2019, with a machine English translation.
Office Action dated Dec. 16, 2019 and English translation thereof which corresponds to Korean Patent Application No. 10-2019-7028877, 15 Total Pages.
JPO, Office Action for the corresponding Japanese Patent Application No. 2016-538438, dated Jan. 14, 2020, with English translation.
KIPO, English translation of the Office Action for the corresponding Korean Patent Application No. 10-2017-7001392, dated Jul. 21, 2020.

* cited by examiner

Energy diagram of 2CzPN

Energy diagram of 2CzPN a b

○ : Hydrogen atom ◎ : Carbon atom ● : Nitrogen atom ● : Oxygen atom

Light

Light

ORGANIC ELECTROLUMINESCENT DEVICE, THIN LUMINOUS FILM, DISPLAY APPARATUS, AND LIGHTING APPARATUS

CROSS REFERENCE TO RELATED APPLICATION

This Application is a 371 of PCT/JP2015/071647 filed on Jul. 30, 2015, which, in turn, claimed the priority of Japanese Patent Application No. JP 2014-156059 filed on Jul. 31, 2014, both applications are incorporated herein by reference.

TECHNICAL FIELD

The present invention relates to an organic electroluminescent device, a thin luminous film, a display apparatus, and a lighting apparatus, each of the apparatuses including the organic electroluminescent device. In particular, the present invention relates to an organic electroluminescent device exhibiting improved emission efficiency and high stability, a thin luminous film, a display apparatus, and a lighting apparatus, each of the apparatuses including the organic electroluminescent device.

BACKGROUND ART

Organic electroluminescent (hereinafter may be referred to as "EL") devices, which are based on electroluminescence of organic materials, have already been put into practice as new light-emitting systems capable of planar emission. Organic EL devices have recently been applied to electronic displays and also to lighting apparatuses. Thus, a demand has arisen for further development of organic EL devices.

Organic EL devices emit light based on either the following two emission modes: "phosphorescence," which occurs during transition of excitons from the triplet excited state to the ground state, and "fluorescence," which occurs during transition of excitons from the singlet excited state to the ground state.

Under the application of an electric field to such an organic EL device, holes and electrons are respectively injected from an anode and a cathode into a luminous layer, and the injected hole and electrons are recombined in the luminous layer, to generate excitons. In this process, singlet excitons and triplet excitons are generated at a ratio of 25%:75%; i.e., a phosphorescent mode, which is based on triplet excitons, theoretically provides higher internal quantum efficiency than a fluorescent mode.

Unfortunately, the achievement of high quantum efficiency in a phosphorescent mode requires the use of a complex of a rare metal (e.g., iridium or platinum) as a central metal, which may cause future problems in the industry in terms of the reserves and prices of rare metals.

In recent years, new techniques have been proposed for development of various fluorescent devices exhibiting improved emission efficiency.

For example, PTL 1 discloses a technique focused on a triplet-triplet annihilation (TTA) phenomenon (hereinafter also called "triplet-triplet fusion (TTF)") wherein singlet excitons are generated by collision of two triplet excitons. This technique prompts the TTA phenomenon to occur effectively and thus improves the emission efficiency of a fluorescent device. Although this technique can increase the emission efficiency of the fluorescent material (hereinafter may be referred to as "fluorescent compound") to two to three times that of a traditional fluorescent material, the emission efficiency is not as high as that of a phosphorescent material because singlet excitons are theoretically generated at an efficiency of only about 40% by the TTA phenomenon.

Adachi, et al. have recently reported fluorescent materials based on a thermally activated delayed fluorescence (hereinafter may be referred to as "TADF") mechanism and applicability of the materials to organic EL devices (refer to, for example, NPLs 1 to 5 and PTL 2).

As illustrated in FIG. 1, the TADF mechanism of a fluorescent material involves a phenomenon wherein excitons undergo reverse intersystem crossing from the triplet excited state to the singlet excited state if the difference between singlet excited energy level and triplet excited energy level ($\Delta Est$) is smaller than that in a common fluorescent compound. A reduction in $\Delta Est$ of an organic compound desirably involves prevention of the overlap between the highest occupied molecular orbital (HOMO) and the lowest unoccupied molecular orbital (LUMO) in the molecule; i.e., complete separation of the HOMO and the LUMO. For example, in a compound 2CzPN illustrated in FIG. 1a, the HOMO spreads over carbazolyl groups at positions 1 and 2 of the benzene ring, and the LUMO spreads over cyano groups at positions 4 and 5 of the benzene ring. Thus, the HOMO and the LUMO are separated from each other, and the compound 2CzPN has a very small $\Delta Est$ (about 0.1 eV or less) and exhibits a TADF phenomenon. In contrast, in a compound 2CzXy (see FIG. 1b) having methyl groups (instead of cyano groups) at positions 4 and 5 of the benzene ring, the HOMO and the LUMO are not clearly separated from each other. Thus, the compound 2CzXy has a relatively large $\Delta Est$ and exhibits no TADF phenomenon.

A small difference in energy level ($\Delta Est$) allows fluorescence to occur. In detail, triplet excitons generated at a probability of 75% through electrical excitation, which would otherwise fail to contribute to fluorescence, transit to the singlet excited state by heat energy during operation of the organic EL device. Fluorescence occurs by radiative deactivation (also referred to as "radiative transition") during transition of the excitons from the singlet excited state to the ground state. The TADF mechanism can theoretically achieve 100% internal quantum efficiency even in a fluorescent material. Unfortunately, the TADF mechanism has not yet been practically used in organic EL devices because of problems derived from luminous materials exhibiting TADF and problems upon application of the mechanism to organic EL devices. A compound having a benzene ring provided with a carbazolyl group (i.e., an electron-donating substituent) and a strong electron-accepting substituent (e.g., a cyano, sulfonyl, or triazinyl group) exhibits TADF properties. Such a compound, however, is still unsatisfactory in terms of blue light-emitting efficiency or molecular stability. Thus, a demand has arisen for a further improvement in properties of the compound.

In general, an organic EL device preferably includes a hole transporting layer composed of a triphenylamine derivative in view of durability and hole transportability. A triphenylamine derivative exhibits a HOMO level of about −4.5 eV to −5.5 eV, which may vary depending on the selection of a substituent. In general, difficulty is encountered in injecting holes into a luminous material contained in a luminous layer if the HOMO level of the luminous material is lower than that of a hole transporting layer.

If holes are injected into the luminous material through a host compound, the HOMO level of the host compound should be equal to or lower than that of the luminous material. In any case, difficulty is encountered in injecting holes into the luminous layer. Thus, emission requires a high voltage capable of injecting holes into the luminous layer from a layer having a HOMO level higher than that of the luminous layer. Even if emission quantum efficiency is improved, high driving voltage leads to difficulty in increasing power efficiency [lm/W], resulting in failure to reduce power consumption. This phenomenon is pronounced in a luminous material having a large band gap; i.e., the phenomenon is more likely to occur in the following order: a deep blue light-emitting material, a blue light-emitting material, a green light-emitting material, and a red light-emitting material. The delayed fluorescence mechanism encounters problems including technical difficulty in the design of a luminous material and a few alternatives of the host compound used in combination with the luminous material. The technical development of a blue light-emitting material is the most difficult hurdle.

A TADF material is synthesized on the basis of the molecular design for reducing ΔEst (i.e., a reduction in overlap between the HOMO and the LUMO in the molecule). The complete separation of the HOMO and the LUMO, however, leads to reduced electron transition between the HOMO and the LUMO (i.e., generation of few excitons), resulting in insufficient emission intensity despite the occurrence of TADF. Thus, a very large overlap between the HOMO and the LUMO leads to no occurrence of TADF, whereas a very small overlap therebetween leads to low emission intensity despite the occurrence of TADF. Although both the occurrence of TADF and high emission intensity are achieved in a traditional compound by the molecular design for appropriate overlap between the HOMO and the LUMO, difficulty is encountered in the design of a TADF molecule exhibiting practical emission intensity and efficiency; i.e., the molecular design has room for improvement. Thus, emission from a TADF compound is affected by a slight variation in overlap between the HOMO and the LUMO in the compound. In detail, the overlap between the HOMO and the LUMO is varied through a slight structural change of the molecule by the transition of excitons from the ground state to the excited state or by external factors, such as heat and electric field, resulting in a variation in emission intensity or formation of broad spectra. These phenomena may apply to the overlap between the HOMO and the LUMO in an exciplex (i.e., a bimolecular complex).

CITATION LIST

Patent Literature

PTL 1: WO2010/134350
PTL 2: Japanese Unexamined Patent Application Publication No. 2011-213643

Non-Patent Literature

NPL 1: "Jitsuyoka Suteji o Mukaeta Yukiko Erekutoronikusu (An advanced stage of organic optoelectronics with the aim of commercialization)" *Oyo Buturi*, Vol. 82, No. 6, 2013
NPL 2: H. Uoyama, et al., Nature, 2012, 492, 234-238
NPL 3: S. Y. Lee, et al., Applied Physics Letters, 2012, 101, 093306-093309
NPL 4: T. Nakagawa, et al., Chem. Commun., 2012, 48, 9580-9582
NPL 5: *Yuki EL Toronkai Dai-10-Kai Reikai Yokoshu* (Proceedings of Japan OLED Forum, 10th Meeting), pp. 11-12, 2010

SUMMARY OF THE INVENTION

Problems to be Solved by the Invention

The present invention has been attained in consideration of the problems and circumstances described above. An object of the present invention is to provide an organic electroluminescent device exhibiting high emission efficiency and high stability (i.e., a slight variation in emission properties over time). Another object of the present invention is to provide a thin luminous film containing a π-conjugated compound for use in the organic electroluminescent device. Still another object of the present invention is to provide a display apparatus and a lighting apparatus, each of the apparatuses including the organic electroluminescent device.

Means to Solve the Problems

The present inventors, who have conducted studies to solve the problems described above, have developed a π-conjugated compound exhibiting no or little overlap between the electron density distributions of the HOMO and the LUMO in the molecule, such that electron transition from the ground state to the excited state (i.e., electron transition between the HOMO and the LUMO) occurs by a through-space interaction in the molecule. The present inventors have found that an organic electroluminescent device including a luminous layer containing the π-conjugated compound exhibits strong fluorescence and high stability. The present invention has been accomplished on the basis of this finding.

The present invention to solve the problems described above is characterized by the following aspects:

1. An organic electroluminescent device including:
   an anode;
   a cathode; and
   an organic layer including at least one luminous layer, the organic layer being disposed between the anode and the cathode, wherein
   at least one of the at least one luminous layer includes a π-conjugated compound exhibiting no overlap between the electron density distributions of the HOMO and the LUMO in the molecule, such that electron transition between the HOMO and the LUMO occurs by a through-space interaction in the molecule, and the π-conjugated compound has a π-conjugated aromatic ring at a moiety on which at least one of the HOMO and the LUMO is localized.

2. The organic electroluminescent device according to item 1, wherein the π-conjugated compound has a structure represented by General formula (A):

[Chem 1]

General formula (A)

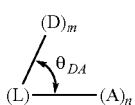

where m and n each represent an integer of 1 to 6, D represents an electron-donating moiety on which the HOMO is localized, A represents an electron-accepting moiety on which the LUMO is localized, and L represents a linkage moiety that connects the electron-donating moiety D and the electron-accepting moiety A and exhibits a HOMO electron density of less than 10% and a LUMO electron density of less than 10%;

the compound having a structure represented by General formula (A) exhibits an angle $\theta_{DA}$ of less than 90° in a stable ground state, the angle $\theta_{DA}$ being formed by a straight line connecting the centroid of the HOMO localized on the electron-donating moiety D and the centroid of the atom of the linkage moiety L adjacent to the electron-donating moiety D and a straight line connecting the centroid of the LUMO localized on the electron-accepting moiety A and the centroid of the atom of the linkage moiety L adjacent to the electron-accepting moiety A; and the distance r between the centroid of the HOMO localized on the electron-donating moiety D and the centroid of the LUMO localized on the electron-accepting moiety A is more than 0 nm and 0.6 nm or less.

3. The organic electroluminescent device according to item 1, wherein the π-conjugated compound has a structure represented by General formula (A):

[Chem 2]

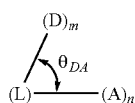

General formula (A)

where m and n each represent an integer of 1 to 6, D represents an electron-donating moiety on which the HOMO is localized, A represents an electron-accepting moiety on which the LUMO is localized, and L represents a linkage moiety that connects the electron-donating moiety D and the electron-accepting moiety A and exhibits a HOMO electron density of less than 10% and a LUMO electron density of less than 10%;

the compound having a structure represented by General formula (A) exhibits an angle $\theta_{DA}$ of less than 90° in a stable ground state, the angle $\theta_{DA}$ being formed by a straight line connecting the centroid of the HOMO localized on the electron-donating moiety D and the centroid of the atom of the linkage moiety L adjacent to the electron-donating moiety D and a straight line connecting the centroid of the LUMO localized on the electron-accepting moiety A and the centroid of the atom of the linkage moiety L adjacent to the electron-accepting moiety A; and the probability of electron transition between the electron-donating moiety D and the electron-accepting moiety A is 80% or more.

4. The organic electroluminescent device according to any one of items 1 to 3, wherein the π-conjugated compound is at least one of compounds having structures represented by General formulae (1) to (5):

[Chem 3]

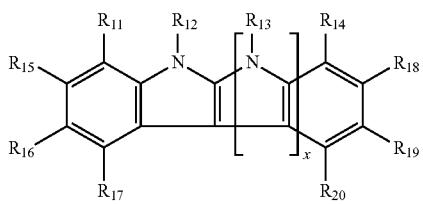

General formula (1)

General Formula (1)
where $R_{11}$, $R_{12}$, $R_{13}$, $R_{14}$, $R_{15}$, $R_{16}$, $R_{17}$, $R_{18}$, $R_{19}$, and $R_{20}$ each independently represent a hydrogen atom or a substituent, and at least one of $R_{11}$, $R_{12}$, $R_{13}$, and $R_{14}$ is represented by General formula (1-A):

[Chem 4]

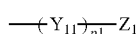

General formula (1-A)

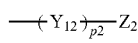

General formula (1-B)

where $Y_{11}$ represents a divalent linkage group, $Z_1$ represents an electron-donating aromatic hydrocarbon or heteroaromatic group, at least one of $R_{11}$, $R_{12}$, $R_{13}$, and $R_{14}$ is represented by General formula (1-B) where $Y_{12}$ represents a divalent linkage group and $Z_2$ represents an electron-accepting aromatic hydrocarbon or heteroaromatic group, and x, p1, and p2 each represent an integer of 0 or 1;

[Chem 5]

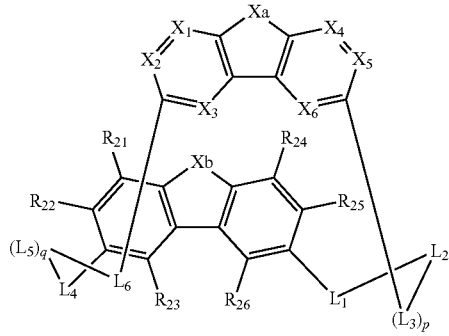

General formula (2)

where $X_a$ and $X_b$ each independently represent an oxygen atom, a sulfur atom, or $NR_c$, $X_1$, $X_2$, $X_3$, $X_4$, $X_5$, and $X_6$ each independently represent a nitrogen atom or $CR_d$ and at least one of $X_1$, $X_2$, $X_3$, $X_4$, $X_5$, and $X_6$ is a nitrogen atom, $R_c$, $R_d$, $R_{21}$, $R_{22}$, $R_{23}$, $R_{24}$, $R_{25}$, and $R_{26}$ each independently represent a hydrogen atom or a substituent, $L_1$, $L_2$, $L_3$, $L_4$, $L_5$, and $L_6$ each represent a divalent linkage group, and p and q each represent an integer of 0 or 1;

[Chem 6]

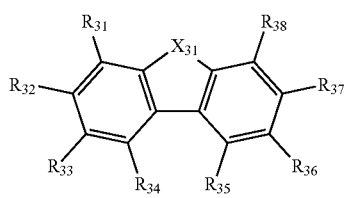

General formula (3)

where $X_{31}$ represents $PR_b(=O)$, $SO_2$, or $SO$, $R_b$, $R_{31}$, $R_{32}$, $R_{33}$, $R_{34}$, $R_{35}$, $R_{36}$, $R_{37}$, and $R_{38}$ each independently represent a hydrogen atom or a substituent, and at least one of $R_{31}$, $R_{33}$, $R_{36}$, and $R_{38}$ is represented by General formula (3-A):

[Chem 7]

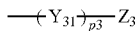

General formula (3-A)

where $Y_{31}$ represents a divalent linkage group, $Z_3$ represents an electron-donating aromatic hydrocarbon or heteroaromatic group, and p3 represents an integer of 0 or 1;

[Chem 8]

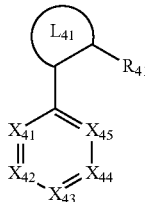

General formula (4)

where $X_{41}$, $X_{42}$, $X_{43}$, $X_{44}$, and $X_{45}$ each independently represent a nitrogen atom or $CR_e$, $R_e$ represents a hydrogen atom or a substituent, $L_{41}$ represents an aromatic hydrocarbon group or a heteroaromatic group, and $R_{41}$ is represented by General formula (4-A):

[Chem 9]

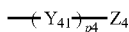

General formula (4-A)

where $Y_{41}$ represents a divalent linkage group, $Z_4$ represents an electron-donating aromatic hydrocarbon or heteroaromatic group, and p4 represents an integer of 0 or 1; and

[Chem 10]

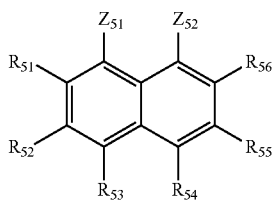

General formula (5)

where $R_{51}$, $R_{52}$, $R_{53}$, $R_{54}$, $R_{55}$, and $R_{56}$ each independently represent a hydrogen atom or a substituent, and $Z_{51}$ and $Z_{52}$ each independently represent an electron-donating aromatic hydrocarbon or heteroaromatic group or an electron-accepting aromatic hydrocarbon or heteroaromatic group, with the proviso that both $Z_{51}$ and $Z_{52}$ are not an electron-donating aromatic hydrocarbon or heteroaromatic group and that both $Z_{51}$ and $Z_{52}$ are not an electron-accepting aromatic hydrocarbon or heteroaromatic group.

5. The organic electroluminescent device according to any one of items 1 to 4, wherein the π-conjugated compound exhibits a ΔEst of 0.5 eV or less where ΔEst represents the absolute value of the difference between the lowest excited singlet energy level and the lowest excited triplet energy level.

6. The organic electroluminescent device according to any one of items 1 to 5, wherein the luminous layer includes the π-conjugated compound and at least one of a fluorescent compound and a phosphorescent compound.

7. The organic electroluminescent device according to any one of items 1 to 6, wherein the luminous layer includes the π-conjugated compound, at least one of a fluorescent compound and a phosphorescent compound, and a host compound.

8. A thin luminous film including the π-conjugated compound according to any one of items 1 to 5.

9. A display apparatus including the organic electroluminescent device according to any one of items 1 to 7.

10. A lighting apparatus including the organic electroluminescent device according to any one of items 1 to 7.

Effects of the Invention

The present invention can provide an organic electroluminescent device exhibiting high emission efficiency and high stability (i.e., a slight variation in emission properties over time). The present invention can also provide a thin luminous film containing a π-conjugated compound for use in the organic electroluminescent device. The present invention can also provide a display apparatus and a lighting apparatus, each of the apparatuses including the organic electroluminescent device.

The mechanisms and operations that establish the advantageous effects of the present invention are not clarified but are inferred as described below.

The terms "electron-donating moiety D" and "electron-accepting moiety A" used herein will be defined below.

The π-conjugated compound according to the present invention is characterized in that no overlap is present between the electron density distributions of the HOMO and the LUMO, and electron transition between the HOMO and the LUMO occurs by a through-space interaction.

The electron transition between the HOMO and the LUMO by a through-space interaction cannot be determined on the basis of actual experimental values, but can be determined on the basis of, for example, the electron transition probability between the HOMO and the LUMO obtained through molecular orbital calculation, or the molecular structure such that the HOMO and the LUMO are completely separated but in physically close contact with each other so as to allow electron transition between the HOMO and the LUMO.

In order to facilitate electron transition between the HOMO and the LUMO, the π-conjugated compound preferably has a structure such that conjugated π-electron planes included in the electron-donating moiety D and the electron-accepting moiety A face each other, and the electron-donating moiety D and the electron-accepting moiety A are in close contact with each other. The π-conjugated compound also preferably has a structure such that a linkage moiety L between the electron-donating moiety D and the electron-accepting moiety A has an aromatic ring or a spiral structure, or the moieties D and A are in close contact with each other and projection planes of the moieties D and A, each having the maximum area, overlap with each other.

In the present invention, the distance r between the centroids of the HOMO and the LUMO is preferably 0.6 nm (6 Å) or less for allowing electron transition between the HOMO and the LUMO.

The term "electron-donating moiety D" used herein refers to a moiety of the π-conjugated compound on which the HOMO is localized and which has a HOMO electron density of 10% or more. The electron-donating moiety D may be composed of a single group or a plurality of groups.

The term "electron-accepting moiety A" used herein refers to a moiety of the π-conjugated compound on which the LUMO is localized and which has a LUMO electron density of 10% or more. The electron-accepting moiety A may be composed of a single group or a plurality of groups.

At least one (preferably both) of the electron-donating moiety D and the electron-accepting moiety A contains a π-conjugated aromatic ring in view of ease of localization of the HOMO or the LUMO and electron transition.

The group contained in the electron-donating moiety D is preferably a π-conjugated aromatic ring group. Specific examples of the group include groups of carbazole, thiophene, pyrrole, benzene, phenoxazine, acridan, indole, and indoloindole rings, and amino groups (e.g., a triphenylamino group). Such a group may further have one or more substituents. The substituents may be bonded together to form a ring. The HOMO may be localized on such a substituent.

The substituent may be of any type that does not inhibit the function of the π-conjugated compound according to the present invention. The substituent may be used for increasing glass transition temperature, preventing the cohesion between molecules of the compound, and adjusting the position of localization of the HOMO and the level of the HOMO.

The group contained in the electron-accepting moiety A is preferably a π-conjugated aromatic ring group. Specific examples of the group include cyano, sulfonyl, and trifluoromethyl groups, a fluorine atom, groups of pyridine, pyrimidine, pyridazine, pyrazine, triazine, dibenzothiophene 5,5-dioxide, oxazole, isoxazole, thiazole, isothiadiazole, imidazole, pyrazole, furazan, indazole, benzothiazole, benzoxazole, benzimidazole, quinolone, isoquinoline, quinazoline, quinoxaline, isoindole, naphthylidine, phthalazine, carboline, diazacarbazole (i.e., prepared through replacement of one of the carbon atoms of carboline with a nitrogen atom), phenanthridine, phenanthroline, phenazine, azadibenzofuran, and azadibenzothiophene rings, and fluorine-substituted alkyl and cycloalkyl groups.

Other examples of the group include cyano, sulfonyl, trifluoromethyl, and fluorine-substituted benzene ring groups.

Such a group may further have one or more substituents. The substituents may be bonded together to form a ring. The LUMO may be localized on such a substituent.

The substituent may be of any type that does not inhibit the function of the π-conjugated compound according to the present invention. The substituent may be used for increasing glass transition temperature, preventing the cohesion between molecules of the compound, and adjusting the position of localization of the LUMO and the level of the LUMO.

Specific examples of the substituent may be similar to substituents represented by $R_{11}$ of General formula (1) described below.

As described above, a small ΔEst is required for occurrence of TADF. A ΔEst of 0.5 eV or less leads to an increase in probability of occurrence of TADF. The structure represented by General formula (A) contributes to localization of the LUMO and the HOMO on the electron-accepting moiety A and the electron-donating moiety D, respectively, resulting in a ΔEst of 0.5 eV or less and occurrence of TADF. In the case of a traditional delayed fluorescent compound, complete separation of the HOMO and the LUMO leads to no electron transition, resulting in no occurrence of TADF. Thus, difficulty is encountered in achieving both occurrence of TADF and practical emission intensity and efficiency. In general, the electron transition during TADF occurs by a through-bond interaction between the HOMO localized on the electron-donating moiety D and the LUMO localized on the electron-accepting moiety A via covalent molecular chains. Fluorene or acridan derivatives are known as TADF materials wherein the HOMO and the LUMO are separated and localized. In such a fluorene or acridan derivative, a moiety having a HOMO electron density is completely orthogonal to a moiety having a LUMO electron density ($\theta_{BA}$=180° in the definition of General formula (A)). Although such a derivative is advantageous in terms of TADF because of a small ΔEst, the electron transition by a through-bond interaction is less likely to occur due to complete separation of the HOMO and the LUMO. In such a derivative, electron transition by a through-space interaction is also less likely to occur due to no close contact between the HOMO and the LUMO. Thus, these phenomena result in low emission intensity and efficiency.

Electron transition by a through-space interaction (instead of a through-bond interaction) has been found to ensure high electron transition probability and high emission efficiency because of close contact between the HOMO and the LUMO (despite complete separation of the HOMO and the LUMO).

The angle $\theta_{DA}$ defined in General formula (A) will now be described with reference to FIG. 2, which is a schematic illustration of a material having an electron-donating moiety D and an electron-accepting moiety A. FIG. 2 schematically illustrates the relationship between the angle $\theta_{DA}$ and electron transition in a π-conjugated compound having a structure represented by General formula (A). As illustrated in FIGS. 2a, 2b, and 2c, an angle $\theta_{DA}$ within the range of the present invention leads to close contact between electron clouds of π-conjugated planes of an electron-donating moiety D and an electron-accepting moiety A, resulting in a small distance between the moieties capable of electron transition therebetween. Thus, electron transition is likely to occur between the HOMO on the electron-donating moiety D and the LUMO on the electron-accepting moiety A, leading to high emission efficiency of the resultant organic EL device. In contrast, an angle $\theta_{DA}$ outside the range of the present invention (see FIGS. 2d and 2e) leads to a large distance between electron clouds of π-conjugated planes of an electron-donating moiety D and an electron-accepting moiety A, resulting in no occurrence of electron transition. In addition, the electron transition by a through-bond interaction is less likely to occur because of no overlap between the electron clouds, resulting in failure to exhibit high emission efficiency.

In the case of overlap between the projection planes of the electron-donating moiety D and the electron-accepting moiety A and close contact between these moieties as described above, electron transition occurs by a through-space interaction (instead of a through-bond interaction via molecular chains between the moieties D and A); i.e., direct electron hopping occurs from the HOMO on the moiety D to the LUMO on the moiety A because of a small distance between the moieties D and A (i.e., close contact between the HOMO and the LUMO). The through-space interaction corresponds to a spatial orbital interaction without formation of chemical bonds. Catenane or rotaxane is an interlocked molecular structure wherein molecules are joined with spatial coupling rather than chemical bonds. Such a molecular structure is known to exhibit a through-space interaction and rapid electron transition (reference: "*Denshi Ido (Kagaku no Yoten Shirizu* 5)" (Electron Transition, Chemical Point Series No. 5), Masashi Ito, The Chemical Society of Japan). A basket-shaped cyclophane having a plurality of aromatic rings and crosslinks (reference: "*Karubazoruto no Hukusokan o*

Kibantosuru Paikyoyakukei Kagobutsu no Gosei to Bussei" (Synthesis and Properties of π-Conjugated Compounds Based on Carbazole), Yosuke Nakamura, Shinichiro Kato, Hiroto Noguchi, Journal of Synthetic Organic Chemistry, Japan, Vol. 71, page 779, 2013) and exciplex are also known to exhibit a through-space interaction (reference: Kenichi Goushi and Chihaya Adachi, Appl. Phys. Lett., Vol. 101, page 023306 (2012)).

In the aforementioned case, the HOMO is completely separated from the LUMO, but the electron-donating moiety D on which the HOMO is localized is in close contact with the electron-accepting moiety A on which the LUMO is localized. In such a case, electron transition occurs by a through-space interaction (instead of a through-bond interaction) because of close contact between the HOMO and the LUMO, resulting in occurrence of TADF. Thus, emission efficiency can be ensured while the HOMO is completely separated from the LUMO; i.e., efficient TADF can be achieved because of minimized ΔEst.

The electron transition between the HOMO and the LUMO occurs by a through-space interaction in the case where the angle $\theta_{DA}$ is less than 90° and the distance r between the centroid of the HOMO on the electron-donating moiety D and the centroid of the LUMO on the electron-accepting moiety A is more than 0 nm and 0.6 nm or less, or the probability of electron transition from the electron-donating moiety D to the electron-accepting moiety A is 80% or more.

The π-conjugated compound having a structure represented by General formula (A) does not necessarily have both the electron-donating moiety D and the electron-accepting moiety A in the molecule. The π-conjugated compound may have at least one of the moieties D and A or a plurality of moieties D and/or moieties A. In a traditional TADF compound, the HOMO is separated from the LUMO through incorporation of a strong electron-accepting group (e.g., a cyano or sulfonyl group) into the molecule. The π-conjugated compound according to the present invention does not necessarily require a strong electron-accepting group because the distance of electron transition is shorter as compared with the case of the traditional TADF compound. Thus, the π-conjugated compound exhibits a lower HOMO level than the traditional TADF compound, and can be used in combination with many types of host compounds. It has been found that the molecular design based on this technical idea can achieve both TADF efficiency and emission intensity, and thus the π-conjugated compound can be used in combination with various types of host molecules.

The π-conjugated compound, which does not have a strong electron-accepting moiety, exhibits reduced localization of charges. Thus, the polarization of charges is reduced between the π-conjugated compound and a medium surrounding the compound (e.g., a host molecule or a solvent), leading to a smaller interaction between the compound and the medium as compared with the case of a traditional TADF material, resulting in reduced broadening of emission spectra.

EMBODIMENTS TO CARRY OUT THE INVENTION

Figure 1:
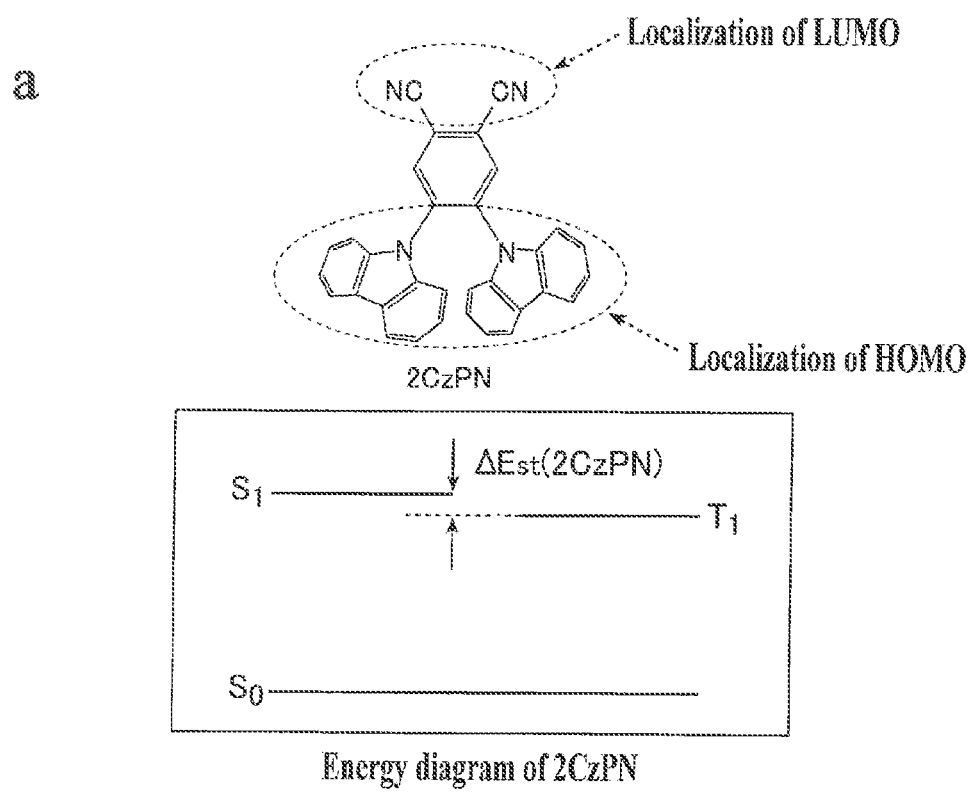
FIG. 1 is a schematic illustration of energy diagrams of a TADF compound (2CzPN: separation of HOMO and LUMO) and a common fluorescent compound (2CzXy: no separation of HOMO and LUMO).
Figure 1:
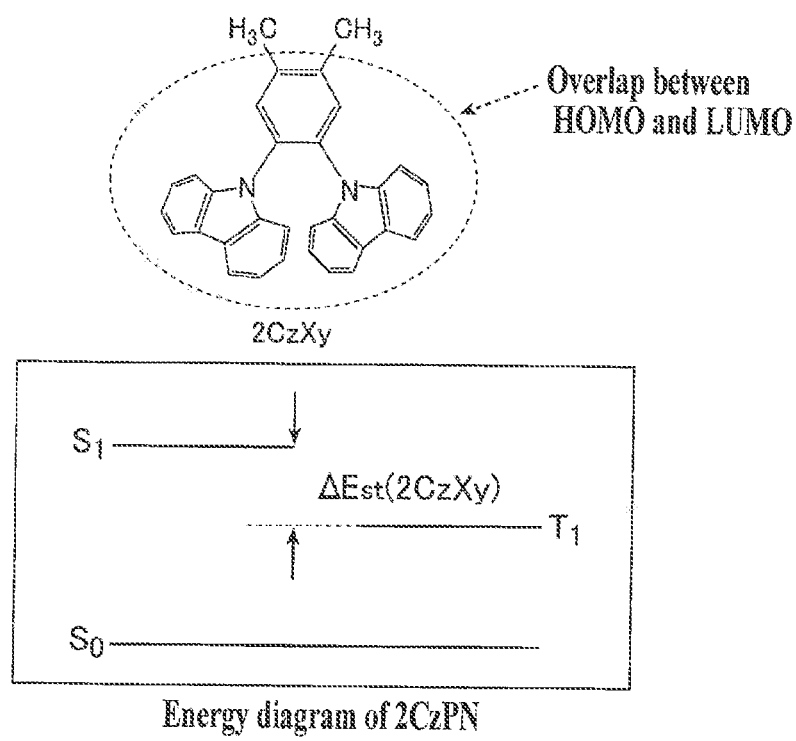
Figure 2:
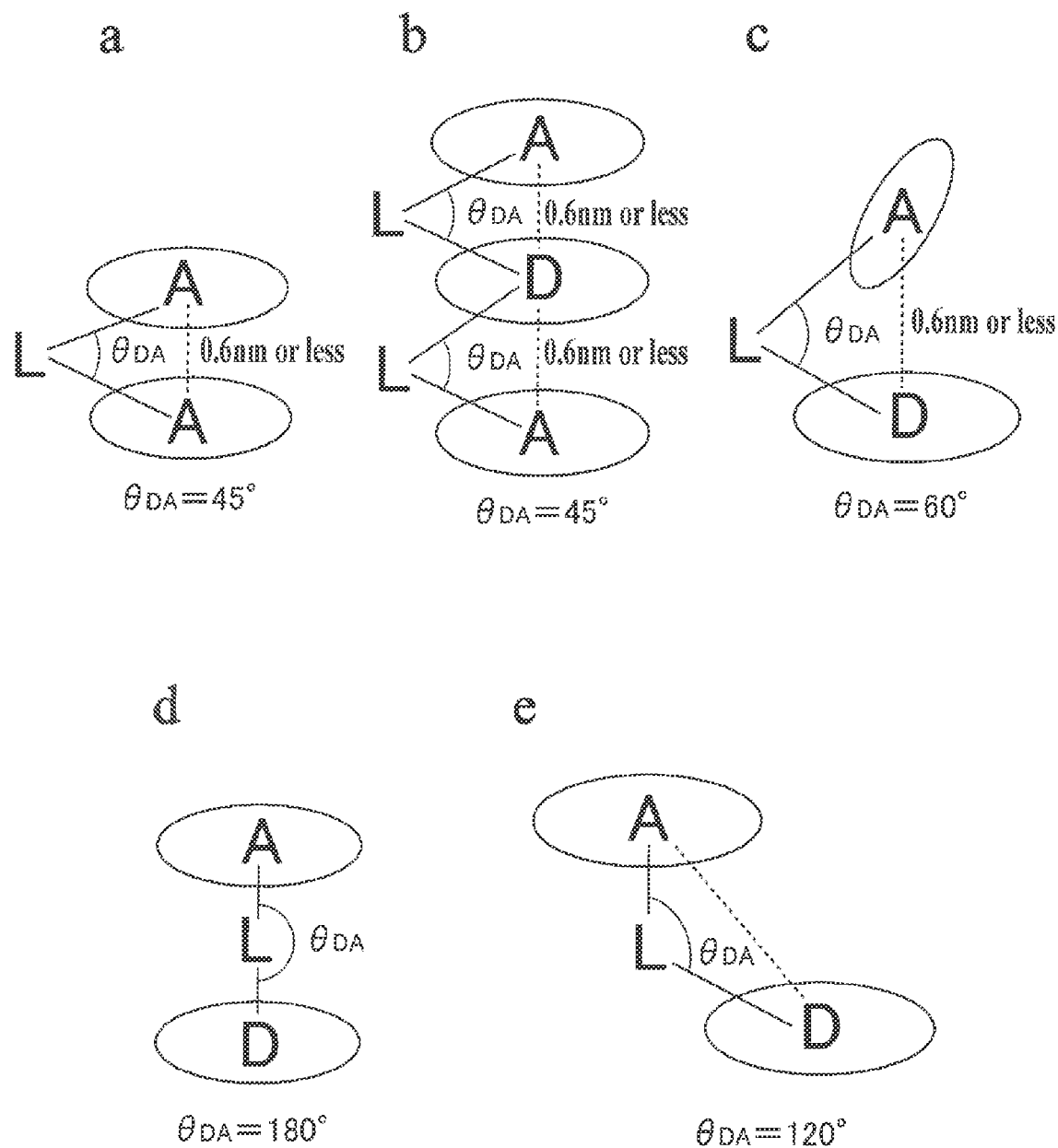
FIG. 2 is a schematic illustration of the relationship between angle $\theta_{DA}$ and electron transition in a π-conjugated compound having a structure represented by General formula (A).

The organic electroluminescent device of the present invention includes an anode, a cathode, and an organic layer including at least one luminous layer, the organic layer being disposed between the anode and the cathode. At least one of the at least one luminous layer includes a π-conjugated compound exhibiting no overlap between the electron density distributions of the HOMO and the LUMO in the molecule, such that electron transition between the HOMO and the LUMO occurs by a through-space interaction in the molecule. The π-conjugated compound has a η-conjugated aromatic ring at a moiety on which at least one of the HOMO and the LUMO is localized.

These technical characteristics are common in Aspects 1 to 10 of the present invention.

In a preferred embodiment of the present invention, the π-conjugated compound has a structure represented by General formula (A) in view of achievement of the advantageous effects of the present invention. In General formula (A), D represents an electron-donating moiety, and A represents an electron-accepting moiety.

The HOMO is localized on the moiety D, and the LUMO is localized on the moiety A.

In General formula (A), L represents a linkage moiety that connects the electron-donating moiety D and the electron-accepting moiety A. The linkage moiety L exhibits a HOMO electron density of less than 10% and a LUMO electron density of less than 10%.

The compound having a structure represented by General formula (A) exhibits an angle $\theta_{DA}$ of less than 90° in a stable ground state, the angle $\theta_{DA}$ being formed by a straight line connecting the centroid of the HOMO localized on the electron-donating moiety D and the centroid of the atom of the linkage moiety L adjacent to the electron-donating moiety D and a straight line connecting the centroid of the LUMO localized on the electron-accepting moiety A and the centroid of the atom of the linkage moiety L adjacent to the electron-accepting moiety A.

The distance r between the centroid of the HOMO localized on the electron-donating moiety D and the centroid of the LUMO localized on the electron-accepting moiety A is more than 0 nm and 0.6 nm or less. This configuration contributes to efficient electron transition between the HOMO and the LUMO and an improvement in emission efficiency.

In another preferred embodiment, the π-conjugated compound has a structure represented by General formula (A). In General formula (A), D represents an electron-donating moiety, and A represents an electron-accepting moiety.

The HOMO is localized on the moiety D, and the LUMO is localized on the moiety A.

In General formula (A), L represents a linkage moiety that connects the electron-donating moiety D and the electron-accepting moiety A. The linkage moiety L exhibits a HOMO electron density of less than 10% and a LUMO electron density of less than 10%.

The compound having a structure represented by General formula (A) exhibits an angle $\theta_{DA}$ of less than 90° in a stable ground state, the angle $\theta_{DA}$ being formed by a straight line connecting the centroid of the HOMO localized on the electron-donating moiety D and the centroid of the atom of the linkage moiety L adjacent to the electron-donating moiety D and a straight line connecting the centroid of the LUMO localized on the electron-accepting moiety A and the centroid of the atom of the linkage moiety L adjacent to the electron-accepting moiety A.

The probability of electron transition between the electron-donating moiety D and the electron-accepting moiety A is 80% or more. This configuration contributes to an improvement in emission efficiency.

In still another preferred embodiment, the π-conjugated compound is at least one of compounds having structures represented by General formulae (1) to (4). This configuration contributes to efficient electron transition between the HOMO and the LUMO and an improvement in emission efficiency.

In still another preferred embodiment, the π-conjugated compound exhibits an absolute value (ΔEst) of the difference between the lowest excited singlet energy level and the lowest excited triplet energy level of 0.5 eV or less. This configuration contributes to reverse intersystem crossing of excitons from the triplet excited state to the singlet excited state, resulting in an improvement in emission efficiency.

In still another preferred embodiment, the luminous layer includes the π-conjugated compound and at least one of a fluorescent compound and a phosphorescent compound. This configuration contributes to an improvement in emission efficiency and stability (i.e., a slight variation in emission properties over time).

In still another preferred embodiment, the luminous layer includes the π-conjugated compound, at least one of a fluorescent compound and a phosphorescent compound, and a host compound. This configuration contributes to a further improvement in emission efficiency and stability (i.e., a slight variation in emission properties over time).

The π-conjugated compound according to the present invention is suitable for use in a thin luminous film.

The organic electroluminescent device of the present invention is suitable for use in a display apparatus and a lighting apparatus.

The present invention, the contexture thereof, and embodiments and aspects for implementing the present invention will now be described in detail. As used herein, the term "to" between two numerical values indicates that the numeric values before and after the term are inclusive as the lower limit value and the upper limit value, respectively.

Now will be described emission modes of an organic EL device and luminous materials, which relate to the technical concept of the present invention.

<Emission Mode of Organic EL Device>

Organic EL devices emit light based on either the following two emission modes: "phosphorescence," which occurs during transition of excitons from the triplet excited state to the ground state, and "fluorescence," which occurs during transition of excitons from the singlet excited state to the ground state.

In the case of electrical excitation of an organic EL device, triplet excitons are generated at a probability of 75%, and singlet excitons are generated at a probability of 25%. Thus, a phosphorescent mode exhibits emission efficiency higher than that of a fluorescent mode, and is effective for reducing power consumption.

A fluorescent mode has been proposed which involves a triplet-triplet annihilation (TTA) mechanism (also called "triplet-triplet fusion (TTF)") wherein emission efficiency is improved by generating one singlet exciton from two triplet excitons, which are generated at a probability of 75% and are generally thermally deactivated (i.e., non-radiative deactivation of the exciton energy).

Adachi, et al. have recently reported that a reduced energy gap between the singlet excited state and the triplet excited state causes reverse intersystem crossing from the triplet excited state (which has a lower energy level) to the singlet excited state depending on the Joule heat during emission and/or the temperature around a luminous device, resulting in fluorescence at substantially 100% (this phenomenon may be referred to as "thermally activated delayed fluorescence" or "thermally activated delayed fluorescence (TADF)"). They have also reported a fluorescent substance that achieves this phenomenon (refer to, for example, NPL 1).

<Phosphorescent Compound>

In theory, phosphorescence has emission efficiency three times higher than that of fluorescence as described above. Unfortunately, energy deactivation from the triplet excited state to the singlet ground state (i.e., phosphorescence) is a forbidden transition and the intersystem crossing from the singlet excited state to the triplet excited state is also a forbidden transition; hence, the rate constant of such a transition is generally small, in other words, the transition is less likely to occur. Thus, the lifetime of excitons is on the order of milliseconds to seconds, and intended emission is difficult to achieve.

In the case of emission of a complex containing a heavy metal, such as iridium or platinum, the rate constant of the aforementioned forbidden transition increases by three or more orders of magnitude by the heavy atom effect of the central metal, and a phosphorescent quantum yield of 100% may be achieved depending on the selection of a ligand.

Unfortunately, such ideal emission requires the use of a rare metal (noble metal), such as a platinum group metal (e.g., iridium, palladium, or platinum), and the use of large amounts of rare metals may cause industrial problems on the reserves and prices of the metals.

<Fluorescent Compound>

Unlike the phosphorescent compound, the fluorescent compound is not necessarily a heavy metal complex, and may be an organic compound composed of combination of common elements, such as carbon, oxygen, nitrogen, and hydrogen. Alternatively, the fluorescent compound may be composed of substantially any substance; for example, a non-metal element, such as phosphorus, sulfur, or silicon, or a complex of a typical metal, such as aluminum or zinc.

Unfortunately, a traditional fluorescent compound is not suitable for highly efficient emission unlike the phosphorescent compound because only 25% of the excitons of the fluorescent compound are used for emission as described above.

<Delayed Fluorescent Compound>

[Excited Triplet-Triplet Annihilation (TTA) Delayed Fluorescent Compound]

An emission mode utilizing delayed fluorescence has been developed for solving the problems involved in a fluorescent compound. The TTA mode, which is based on collision between triplet excitons, is described by the formula illustrated below. In detail, the TTA mode is advantageous in that some triplet excitons, the energy of which would otherwise be converted into only heat by non-radiative deactivation, undergo reverse intersystem crossing, to generate singlet excitons that can contribute to luminescence. In the organic EL device, the TTA mode can achieve an external quantum efficiency about twice that achieved in a traditional fluorescent device.

General formula: $T^*+T^* \rightarrow S^*+S$ where T* represents a triplet exciton, S* represents a singlet exciton, and S represents a molecule in the ground state.

Unfortunately, the TTA mode fails to achieve 100% internal quantum efficiency in principle because two triplet excitons generate only one singlet exciton that contributes to luminescence as illustrated in the aforementioned formula.

[Thermally Activated Delayed Fluorescent (TADF) Compound]

The TADF mode, which is another highly efficient fluorescent mode, can solve problems involved in the TTA mode.

As described above, an advantage of the fluorescent compound is boundless molecular design. Some molecularly designed compounds exhibit a very small absolute value of the difference between excited triplet energy level and excited singlet energy level (hereinafter the absolute value will be referred to as "ΔEst") (see FIG. 1a). Such a compound, although having no heavy atom in the molecule, undergoes reverse intersystem crossing from the triplet excited state to the singlet excited state because of small ΔEst. Since the rate constant of deactivation from the singlet excited state to the ground state (i.e., fluorescence) is very large, the transition of triplet excitons to the ground state via the singlet excited state with emission of fluorescence is kinetically more advantageous than the transition of the triplet excitons to the ground state with thermal deactivation (non-radiative deactivation). Thus, the TADF mode can achieve 100% fluorescence in principle.

<Molecular Design on ΔEst>

The molecular design for reducing ΔEst will now be described.

The most effective way for decreasing ΔEst in a molecule is to reduce the spatial overlap between the highest occupied molecular orbital (HOMO) and the lowest unoccupied molecular orbital (LUMO) in principle.

In general, HOMO spreads over an electron-donating moiety, and LUMO spreads over an electron-accepting moiety. Thus, the HOMO and LUMO in a molecule can be separated from each other through introduction of an electron donor and an electron acceptor into the molecule.

For example, the technique disclosed in NPL 1 involves the separation of LUMO and HOMO from each other through introduction of an electron acceptor (e.g., a cyano group, a sulfonyl group, or triazine) and an electron donor (e.g., carbazole or a diphenylamino group).

Another effective way for decreasing ΔEst is to reduce a change in molecular structure of a compound between the ground state and the triplet excited state by, for example, providing the compound with rigidity. As used herein, the term "rigidity" refers to a reduced number of freely movable portions in the molecule; for example, prevention of free rotation of a bond between rings in the molecule, or introduction of a condensed ring having a large π-conjugated surface. In particular, a change in molecular structure of a compound can be reduced in the excited state by providing a luminous moiety of the compound with rigidity.

<General Problems of TADF Compound>

A TADF compound poses various problems in terms of emission mechanism and molecular structure.

General problems involved in a TADF compound will now be described.

In a TADF compound, the HOMO moiety should be separated from the LUMO moiety for reducing ΔEst. Thus, the electronic state of a molecule is similar to a donor-acceptor intermolecular charge transfer (CT) state in which the HOMO and LUMO moieties are separated from each other.

In the presence of a plurality of such molecules, the molecular structure is stabilized by bringing the donor moiety of one molecule into close contact with the acceptor moiety of another molecule. Such stabilization can be achieved between two or more molecules (e.g., three molecules or five molecules). Thus, various stable states are provided, resulting in broad absorption and emission spectra. Even in the case where a molecular aggregate is not formed from three or more molecules, various stable states are provided depending on the direction or angle of the interaction between two molecules, resulting in broad absorption and emission spectra.

A broad emission spectrum poses two serious problems.

One problem is a reduction in color purity of emitted light. Reduced color purity does not cause serious problems when the organic EL device is used for lighting applications. Reduced color purity, however, precludes application of the organic EL device in a commercial electronic display, due to a reduction in region of color reproduction and poor color reproducibility.

The other problem is shortening of the rising wavelength (also called "fluorescent zero-zero band") of an emission spectrum; i.e., an increase in lowest excited singlet energy level $S_1$.

If the fluorescent zero-zero band is shortened, the phosphorescent zero-zero band, which is derived from the energy level $T_1$ lower than $S_1$, is also shortened (i.e., an increase in $T_1$). Thus, the $T_1$ and $S_1$ of a host compound should be increased for preventing reverse energy transfer from the dopant, which may result in serious problems.

The host compound, which is generally an organic compound, may be in the state of a plurality of unstable active chemical species (i.e., cationic radical state, anionic radical state, and excited state) in the organic EL device. Such chemical species can be relatively stabilized through the extension of an intramolecular π-conjugated system.

In a TADF compound containing no heavy metal, transition from the triplet excited state to the ground state (energy deactivation) is forbidden, and thus the lifetime of excitons in the triplet excited state is very long; i.e., on the order of several hundreds of microseconds to milliseconds. Thus, even if the energy level $T_1$ of the host compound is higher than that of the fluorescent compound, reverse energy transfer is highly likely to occur from the triplet excited state of the fluorescent compound to the host compound due to long lifetime of the excitons. Accordingly, undesired reverse energy transfer to the host compound predominates over the intended reverse intersystem crossing of the TADF compound from the triplet excited state to the singlet excited state, resulting in insufficient emission efficiency.

In order to solve the aforementioned problems, the TADF compound needs to be modified such that the compound exhibits a sharp emission spectrum and a small difference between the maximum emission wavelength and the rising wavelength of the emission spectrum. This can be achieved by reducing a change in molecular structure between the singlet excited state and the triplet excited state.

In addition, the lifetime of excitons in the triplet excited state of the TADF compound is shortened for effectively preventing the reverse energy transfer to the host compound. This can be achieved by reducing a change in molecular structure between the ground state and the triplet excited state, and introducing a substituent or element suitable for avoiding the forbidden transition.

In the organic EL device of the present invention, the luminous layer includes, as a TADF compound, a π-conjugated compound exhibiting no overlap between the electron density distributions of the HOMO and the LUMO in the molecule, such that electron transition between the HOMO and the LUMO occurs by a through-space interaction in the molecule. In this case, the π-conjugated compound serves as a fluorescent compound exhibiting TADF properties.

The incorporation of the π-conjugated compound exhibiting TADF properties (serving as a third component (assist dopant)) into a luminous layer including a host compound and a luminous compound (i.e., a fluorescent or phosphorescent compound) is effective for achievement of high emission efficiency (reference: H. Nakanotani, et al., Nature Communication, 2014, 5, 4016-4022). In the case of generation of singlet excitons (25%) and triplet excitons (75%) on the assist dopant through electrical excitation, the triplet excitons can be converted into singlet excitons by reverse intersystem crossing (RISC). The energy of the singlet excitons is transferred to the luminous compound to cause the compound to emit light. In theory, the exciton energy (100%) can be used to cause the luminous compound to emit light, resulting in high emission efficiency.

As described above, the concept of the present invention includes a π-conjugated compound exhibiting reduced structural change in the excited state and shortened exciton lifetime in the triplet excited state.

Now will be described methods of determining the properties of the π-conjugated compound according to the present invention.

[Electron Density Distribution]

In the π-conjugated compound according to the present invention, it is preferred that the HOMO and the LUMO be substantially separated in molecules in view of a reduction in ΔEst. The spreading of the HOMO and the LUMO can be determined from the electron density distribution obtained through the structural optimization by molecular orbital calculation.

In the π-conjugated compound according to the present invention, the structural optimization by molecular orbital calculation and determination of the electron density distribution can be performed with software for molecular orbital calculation using B3LYP (functional) and 6-31G(d) (basis function). The electron density distribution can be determined with any software.

The software for molecular orbital calculation used in the present invention is Gaussian 09 (Revision C.01, M. J. Frisch, et al., Gaussian, Inc., 2010).

The state of separation of the HOMO and the LUMO may be determined by the following expression: $\Delta Est = E(S_1) - E(T_1)$ where $E(S_1)$ and $E(T_1)$ are respectively the excited energy levels $S_1$ and $T_1$, which are calculated through the time-dependent density functional theory (time-dependent DFT) on the basis of the structural optimization determined using the aforementioned B3LYP (functional) and 6-31G(d) (basis function). A smaller ΔEst value indicates a larger distance between the HOMO and the LUMO. In the present invention, the ΔEst value calculated by the aforementioned method is preferably 0.5 eV or less, more preferably 0.2 eV or less, most preferably 0.1 eV or less.

[Lowest Excited Singlet Energy Level $S_1$]

In the present invention, the lowest excited singlet energy level $S_1$ of the π-conjugated compound may be determined by a common technique. In detail, a target compound is vapor-deposited onto a quartz substrate to prepare a sample, and an absorption spectrum of the sample is measured at ambient temperature (300 K) (vertical axis: absorbance, horizontal axis: wavelength). A tangential line is drawn at the rising point of the absorption spectrum on the longer wavelength side, and the lowest excited singlet energy level is calculated by a specific conversion expression on the basis of the wavelength at the point of intersection of the tangential line with the horizontal axis.

If the π-conjugated compound used in the present invention is likely to cause molecular cohesion, a thin film prepared from the compound may cause a measurement error due to molecular cohesion. In the present invention, the lowest excited singlet energy level $S_1$ is determined from, as an approximation, the peak wavelength of emission of a solution of the π-conjugated compound at room temperature (25° C.) in consideration of a relatively small Stokes shift of the π-conjugated compound and a small change in structure of the compound between the excited state and the ground state.

This determination process may involve the use of a solvent that is less likely to affect the molecular cohesion of the π-conjugated compound; for example, a non-polar solvent, such as cyclohexane or toluene.

[Lowest Excited Triplet Energy Level $T_1$]

In the present invention, the lowest excited triplet energy level ($T_1$) of the π-conjugated compound is determined on the basis of the photoluminescent (PL) properties of a solution or thin film of the compound. For example, a thin film is prepared from a dilute dispersion of the π-conjugated compound, and the transient PL properties of the thin film are determined with a streak camera for separation of a fluorescent component and a phosphorescent component, to determine the energy level difference ΔEst between these components. The lowest excited triplet energy level of the π-conjugated compound can be calculated on the basis of the lowest excited singlet energy level.

For determination of the lowest excited triplet energy level, the absolute PL quantum yield was determined with an absolute PL quantum yield measuring apparatus C9920-02 (manufactured by Hamamatsu Photonics K.K.). The emission lifetime was determined with a streak camera C4334 (manufactured by Hamamatsu Photonics K.K.) under excitation of the sample with a laser beam.

<<Organic EL Device>>

The organic EL device of the present invention includes an anode, a cathode, and an organic layer including at least one luminous layer, the organic layer being disposed between the anode and the cathode. At least one of the at least one luminous layer includes a π-conjugated compound exhibiting no overlap between the electron density distributions of the HOMO and the LUMO in the molecule, such that electron transition between the HOMO and the LUMO occurs by a through-space interaction in the molecule. The π-conjugated compound has a π-conjugated aromatic ring at a moiety on which at least one of the HOMO and the LUMO is localized. The HOMO and the LUMO of the π-conjugated compound can be determined through molecular orbital calculation using B3LYP (functional) and 6-31G(d) (basis function).

The organic EL device of the present invention will be described in detail below.

<<Layer Configuration of Organic EL Device>>

Typical examples of the configuration of the organic EL device of the present invention include, but are not limited to, the following configurations.

(1) Anode/luminous layer/cathode
(2) Anode/luminous layer/electron transporting layer/cathode
(3) Anode/hole transporting layer/luminous layer/cathode
(4) Anode/hole transporting layer/luminous layer/electron transporting layer/cathode
(5) Anode/hole transporting layer/luminous layer/electron transporting layer/electron injecting layer/cathode
(6) Anode/hole injecting layer/hole transporting layer/luminous layer/electron transporting layer/cathode
(7) Anode/hole injecting layer/hole transporting layer/(electron blocking layer)/luminous layer/(hole blocking layer)/electron transporting layer/electron injecting layer/cathode Among the aforementioned configurations, configuration (7) is preferred, but any other configuration may be used.

The luminous layer according to the present invention is composed of a single layer or a plurality of sublayers. A luminous layer composed of a plurality of luminous sublayers may include a non-luminous intermediate sublayer between the luminous sublayers.

A hole blocking layer (also referred to as "hole barrier layer") or an electron injecting layer (also referred to as "cathode buffer layer") may optionally be disposed between the luminous layer and the cathode. An electron blocking layer (also referred to as "electron barrier layer") or a hole injecting layer (also referred to as "anode buffer layer") may be disposed between the luminous layer and the anode.

The electron transporting layer according to the present invention, which has a function of transporting electrons, encompasses the electron injecting layer and the hole blocking layer in a broad sense. The electron transporting layer may be composed of a plurality of sublayers.

The hole transporting layer according to the present invention, which has a function of transporting holes, encompasses the hole injecting layer and the electron blocking layer in a broad sense. The hole transporting layer may be composed of a plurality of sublayers.

In the typical configurations described above, any of the layers other than the anode and the cathode may also be referred to as "organic layer."

(Tandem Structure)

The organic EL device of the present invention may have a tandem structure including a plurality of luminous units each including at least one luminous layer.

A typical tandem structure of the organic EL device is as follows:

Anode/first luminous unit/intermediate layer/second luminous unit/intermediate layer/third luminous unit/cathode In this structure, the first, second, and third luminous units may be identical to or different from one another. Any two of the luminous units may be identical to each other, and may be different from the remaining one unit.

Two luminous units may be bonded directly to each other, or an intermediate layer may be disposed therebetween. The intermediate layer is generally also called "intermediate electrode," "intermediate conductive layer," "charge generating layer," "electron extraction layer," "connection layer," or "intermediate insulating layer." Any known material can be used for forming an intermediate layer capable of supplying electrons to the adjacent layer toward the anode and supplying holes to the adjacent layer toward the cathode.

Examples of the material used for the intermediate layer include, but are not limited to, conductive inorganic compounds, such as indium tin oxide (ITO), indium zinc oxide (IZO), $ZnO_2$, TiN, ZrN, HfN, $TiO_x$, $VO_x$, CuI, InN, GaN, $CuAlO_2$, $CuGaO_2$, $SrCu_2O_2$, $LaB_6$, $RuO_2$, and Al; two-layer films, such as $Au/Bi_2O_3$; multi-layer films, such as $SnO_2$/$Ag/SnO_2$, ZnO/Ag/ZnO, $Bi_2O_3/Au/Bi_2O_3$, $TiO_2$/TiN/$TiO_2$, and $TiO_2$/ZrN/$TiO_2$; fullerene compounds, such as $C_{60}$; conductive organic substances, such as oligothiophenes; and conductive organic compounds, such as metal phthalocyanines, metal-free phthalocyanines, metal porphyrins, and metal-free porphyrins.

Examples of preferred luminous units include, but are not limited to, the aforementioned typical device configurations (1) to (7) (exclusive of the anode and the cathode).

Specific examples of tandem organic EL devices include, but are not limited to, device configurations and constituent materials disclosed in U.S. Pat. Nos. 6,337,492, 7,420,203, 7,473,923, 6,872,472, 6,107,734, and 6,337,492, International Patent Publication WO2005/009087, Japanese Unexamined Patent Application Publication Nos. 2006-228712, 2006-24791, 2006-49393, 2006-49394, 2006-49396, 2011-96679, and 2005-340187, Japanese Patent Nos. 4711424, 3496681, 3884564, and 4213169, Japanese Unexamined Patent Application Publication Nos. 2010-192719, 2009-076929, 2008-078414, 2007-059848, 2003-272860, and 2003-045676, and International Patent Publication WO2005/094130.

Now will be described individual layers forming the organic EL device of the present invention.

<<Luminous Layer>>

The luminous layer according to the present invention provides a site for recombination of electrons and holes injected from the electrodes or adjacent layers to emit light through generation of excitons. A luminous portion may be located within the luminous layer or at the interface between the luminous layer and the layer adjacent thereto. The luminous layer may have any configuration satisfying the requirements of the present invention.

The luminous layer may have any total thickness. The luminous layer has a total thickness of preferably 2 nm to 5 μm, more preferably 2 to 500 nm, still more preferably 5 to 200 nm, in view of the homogeneity of the layer, inhibition of application of unnecessarily high voltage upon light emission, and an improvement in stability of the color of emitted light against driving current.

The sublayers forming the luminous layer each have a thickness of preferably 2 nm to 1 μm, more preferably 2 to 200 nm, still more preferably 3 to 150 nm.

The luminous layer preferably contains the π-conjugated compound according to the present invention and a luminous dopant (also referred to as "luminous compound," "luminous dopant compound," "dopant compound," or "dopant") and the below-described host compound (also referred to as "matrix material," "luminous host compound," or "host").

(1) Luminous Dopant

The luminous dopant is preferably a fluorescent dopant (also referred to as "fluorescent compound"), a delayed fluorescent dopant, or a phosphorescent dopant (also referred to as "phosphorescent compound").

In the present invention, the luminous layer contains the π-conjugated compound according to the present invention as a fluorescent compound or an assist dopant in an amount of preferably 5 to 40 mass %, particularly preferably 10 to 30 mass %.

The concentration of the π-conjugated compound in the luminous layer may be appropriately determined depending on the type of the π-conjugated compound used and the requirements for the device. The luminous layer may contain the π-conjugated compound at a uniform concentration across the thickness, or may have any concentration profile of the π-conjugated compound.

In the present invention, two or more π-conjugated compounds may be used in combination. In detail, fluorescent compounds having different structures may be used in combination, or a fluorescent compound may be used in combination with a phosphorescent compound. Thus, the organic EL device can emit light of any color.

The π-conjugated compound according to the present invention may be used for assisting the emission of light from a different fluorescent or phosphorescent compound. In such a case, the luminous layer preferably contains a host compound in an amount of 100% or more by mass relative to the π-conjugated compound according to the present invention, and a different fluorescent or phosphorescent compound in an amount of 0.1 to 50% by mass relative to the π-conjugated compound according to the present invention.

In the case where the π-conjugated compound according to the present invention is used for assisting the emission of light from a different fluorescent or phosphorescent compound, the luminous layer preferably contains three or more components (including the host compound).

In view of high emission efficiency, the luminous layer preferably contains the π-conjugated compound according to the present invention exhibiting an absolute value of the difference between the lowest excited singlet energy level and the lowest excited triplet energy level of 0.5 eV or less in combination with at least one of a fluorescent compound and a phosphorescent compound. The luminous layer does not necessarily contain a host compound, but preferably contains one or more host compounds. The luminous layer may contain two or more π-conjugated compounds and two or more luminous compounds. More preferably, the luminous layer contains one π-conjugated compound, one luminous compound, and one host compound.

Figure 6A:
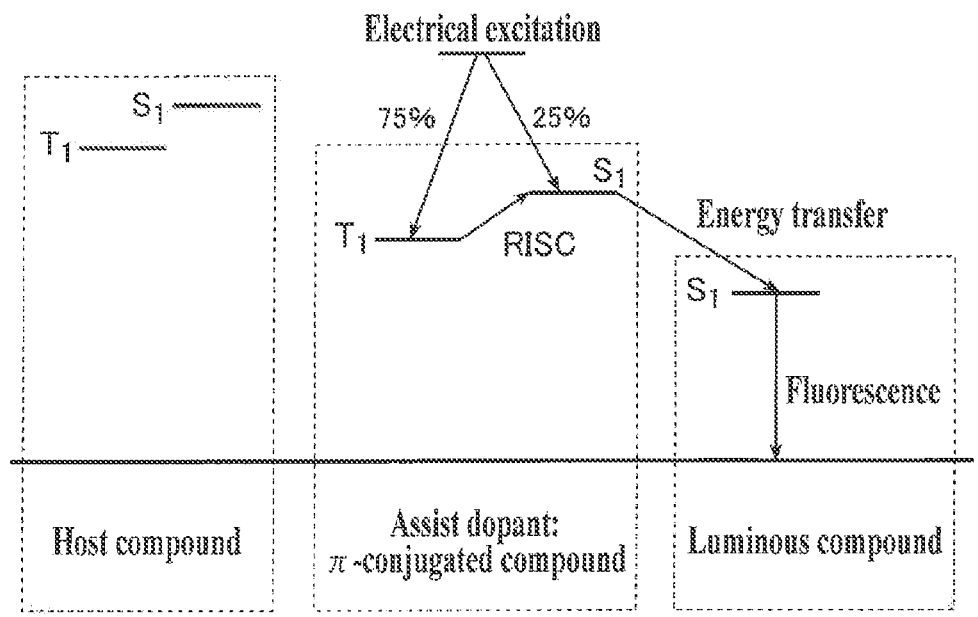
FIG. 6A is a schematic illustration of the case where a π-conjugated compound serves as an assist dopant.
Figure 6B:
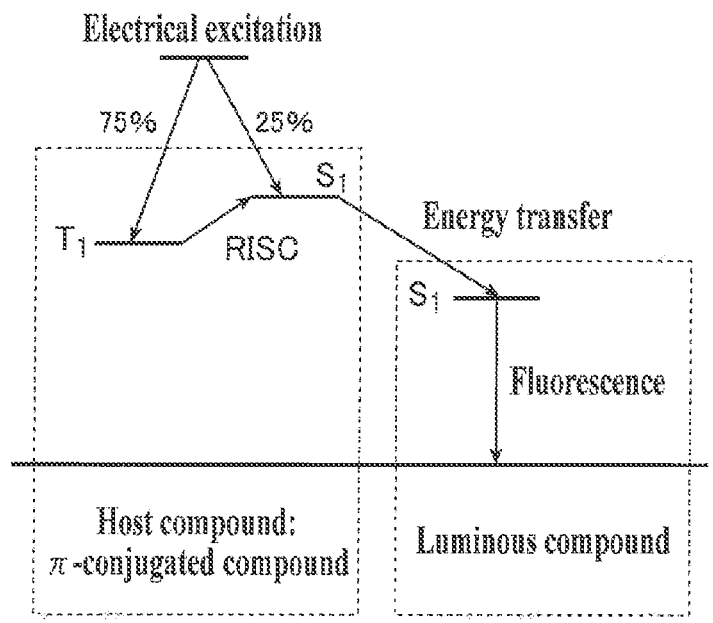
FIG. 6B is a schematic illustration of the case where a π-conjugated compound serves as a host compound.

In the case of the presence of a host compound in the luminous layer containing a luminous compound and the π-conjugated compound according to the present invention exhibiting an absolute value of the difference between the lowest excited singlet energy level and the lowest excited triplet energy level of 0.5 eV or less, the π-conjugated compound serves as an assist dopant. In the case of the absence of a host compound in the luminous layer, the π-conjugated compound serves as a host compound. In both cases, the π-conjugated compound exhibits its effects through a mechanism by which triplet excitons generated on the π-conjugated compound are converted into singlet excitons by reverse intersystem crossing (RISC). In theory, the energy of all the excitons generated on the π-conjugated compound can be transferred to the luminous compound, resulting in high emission efficiency. FIG. 6A schematically illustrates the case where the π-conjugated compound according to the present invention serves as an assist dopant, and FIG. 6B schematically illustrates the case where the π-conjugated compound serves as a host compound. Although FIGS. 6A and 6B illustrate the case where electric excitation generates triplet excitons in the π-conjugated compound, the excitons may be generated through energy or electron transition in the luminous layer or from the interface between the luminous layer and a layer adjacent thereto. Although FIGS. 6A and 6B illustrate the case where the luminous material is a fluorescent compound, the luminous material may be a phosphorescent compound or a combination of a fluorescent compound and a phosphorescent compound.

In the case where the π-conjugated compound according to the present invention exhibiting an absolute value of the difference between the lowest excited singlet energy level and the lowest excited triplet energy level of 0.5 eV or less is used as an assist dopant, the luminous layer preferably contains a host compound in an amount of 100% or more by mass relative to the π-conjugated compound, and a fluorescent and/or phosphorescent compound in an amount of 0.1 to 50% by mass relative to the π-conjugated compound. The energy levels $S_1$ and $T_1$ of the π-conjugated compound are preferably lower than the energy levels $S_1$ and $T_1$ of the host compound and higher than the energy levels $S_1$ and $T_1$ of the luminous compound.

In the case where the π-conjugated compound according to the present invention exhibiting an absolute value of the difference between the lowest excited singlet energy level and the lowest excited triplet energy level of 0.5 eV or less is used as a host compound, the luminous layer preferably contains a fluorescent and/or phosphorescent compound in an amount of 0.1 to 50% by mass relative to the π-conjugated compound. The energy levels $S_1$ and $T_1$ of the compound according to the present invention are preferably higher than the energy levels $S_1$ and $T_1$ of the luminous compound.

In the case where the π-conjugated compound according to the present invention exhibiting an absolute value of the difference between the lowest excited singlet energy level and the lowest excited triplet energy level of 0.5 eV or less is used as an assist dopant or a host compound, the emission spectrum of the π-conjugated compound preferably overlaps with the absorption spectrum of the luminous compound.

Figure 3:
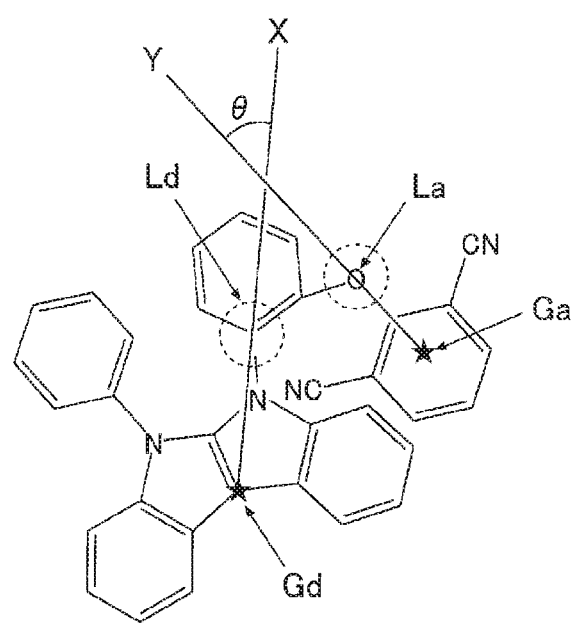
FIG. 3 is a schematic illustration of the definition of angle $\theta_{DA}$ in a π-conjugated compound having a structure represented by General formula (A).

The color of light emitted from the organic EL device or compound according to the present invention is determined by applying values obtained with a spectroradiometer CS-1000 (manufactured by Konica Minolta, Inc.) to the CIE chromaticity coordinate shown in FIG. 3.16 on page 108 of "*Shinpen Shikisai Kagaku Handobukku* (Handbook of Color Science)" (edited by the Color Science Association of Japan, published from University of Tokyo Press, 1985).

In the present invention, one or more luminous layers preferably contain a plurality of luminous dopants that emit light of different colors for emission of white light.

The luminous layers may contain any combination of luminous dopants that emit white light; for example, a combination of blue and orange light-emitting dopants, or a combination of blue, green, and red light-emitting dopants.

For emission of white light from the organic EL device of the present invention, the chromaticity in the CIE 1931

Color Specification System at 1,000 cd/m² preferably falls within a region of x=0.39±0.09 and y=0.38±0.08 during determination of front luminance (viewing angle: 2°) by the aforementioned process.

(1.1) π-Conjugated Compound

In the organic EL device of the present invention, the luminous layer includes a π-conjugated compound exhibiting no overlap between the electron density distributions of the HOMO and the LUMO in the molecule, such that electron transition between the HOMO and the LUMO occurs by a through-space interaction in the molecule. The π-conjugated compound has a π-conjugated aromatic ring at a moiety on which at least one of the HOMO and the LUMO is localized. The HOMO and the LUMO of the luminous material can be determined through molecular orbital calculation using B3LYP (functional) and 6-31G(d) (basis function).

[Compound Represented by General Formula (A)]

In the organic EL device of the present invention, at least one luminous layer preferably includes a luminous material; i.e., a compound having a structure represented by General formula (A).

[Chem 11]

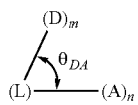

General formula (A)

In General formula (A), D represents an electron-donating moiety, and A represents an electron-accepting group. The HOMO is localized on the moiety D, and the LUMO is localized on the moiety A.

In General formula (A), L represents a linkage moiety that connects the electron-donating moiety D and the electron-accepting moiety A. The linkage moiety L exhibits a HOMO electron density of less than 10% and a LUMO electron density of less than 10%.

The compound having a structure represented by General formula (A) exhibits an angle $\theta_{DA}$ of less than 90° in a stable ground state, the angle $\theta_{DA}$ being formed by a straight line connecting the centroid of the HOMO localized on the electron-donating moiety D and the centroid of the atom of the linkage moiety L adjacent to the electron-donating moiety D and a straight line connecting the centroid of the LUMO localized on the electron-accepting moiety A and the centroid of the atom of the linkage moiety L adjacent to the electron-accepting moiety A.

In General formula (A), L represents a linkage moiety that connects the electron-donating moiety D and the electron-accepting moiety A. The angle $\theta_{DA}$ formed by (the centroid of the HOMO on the electron-donating moiety D)-L-(the centroid of the LUMO on the electron-accepting moiety A) is less than 90°, and the distance r between the centroid of the HOMO on the electron-donating moiety D and the centroid of the LUMO on the electron-accepting moiety A is more than 0 nm and 0.6 nm or less, preferably 0.5 nm or less.

In General formula (A), L represents a linkage moiety that exhibits a HOMO electron density of less than 10% and a LUMO electron density of less than 10%, and connects the electron-donating moiety D and the electron-accepting moiety A. The angle $\theta_{DA}$ formed by (the centroid of the HOMO on the electron-donating moiety D)-L-(the centroid of the LUMO on the electron-accepting moiety A) is less than 90°, and the probability of electron transition from the electron-donating moiety D to the electron-accepting moiety A is 80% or more, preferably 90% or more.

In General formula (A), the linkage moiety L, which connects the electron-donating moiety D and the electron-accepting moiety A, may be any group that does not inhibit the function of the compound represented by General formula (A). The linkage moiety L is preferably a group composed of carbon, nitrogen, oxygen, and sulfur atoms, more preferably an aromatic hydrocarbon ring, an aromatic heterocyclic ring, or a combination thereof.

Specific examples of the group contained in the electron-donating moiety D and the electron-accepting moiety A in General formula (A) include groups described above. The moieties D and A may be linked by a moiety other than the moiety L.

The compound having a structure represented by Formula (A) is preferably represented by General formulae (1) to (4) described below.

[Compound Represented by General Formula (1)]

[Chem 12]

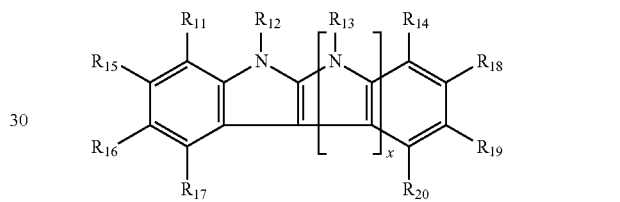

General formula (1)

In General Formula (1), $R_{11}$, $R_{12}$, $R_{13}$, $R_{14}$, $R_{15}$, $R_{16}$, $R_{17}$, $R_{18}$, $R_{19}$, and $R_{20}$ hydrogen atom or a substituent. At least one of $R_{11}$, $R_{12}$, $R_{13}$, and $R_{14}$ is represented by General formula (1-A) described below.

[Chem 13]

In General formula (1-A), $Y_{11}$ represents a divalent linkage group and $Z_1$ represents an electron-donating aromatic hydrocarbon or heteroaromatic group.

At least one of $R_{11}$, $R_{12}$, $R_{13}$, and $R_{14}$ is represented by General formula (1-B) described above. In General formula (1-B), $Y_{12}$ represents a divalent linkage group and $Z_2$ represents an electron-accepting aromatic hydrocarbon or heteroaromatic group. x, p1, and p2 each represent an integer of 0 or 1.

In General formula (1), $R_{11}$, $R_{12}$, $R_{13}$, $R_{14}$, $R_{15}$, $R_{16}$, $R_{17}$, $R_{18}$, $R_{19}$, and $R_{20}$ represent a hydrogen atom or a substituent. If $R_{11}$, $R_{12}$, $R_{13}$, $R_{14}$, $R_{15}$, $R_{16}$, $R_{17}$, $R_{18}$, $R_{19}$, and $R_{20}$ in General formula (1) represent a substituent, examples of the substituent include alkyl groups (e.g., methyl, ethyl, propyl, isopropyl, tert-butyl, pentyl, hexyl, octyl, dodecyl, tridecyl, tetradecyl, and pentadecyl), cycloalkyl groups (e.g., cyclopentyl and cyclohexyl), alkenyl groups (e.g., vinyl and allyl), alkynyl groups (e.g., ethynyl and propargyl), aromatic hydrocarbon groups (also referred to as aromatic hydrocarbon ring groups, aromatic carbocyclic groups, or aryl groups, such as phenyl, p-chlorophenyl, mesityl, tolyl, xylyl, naphthyl, anthryl, azulenyl, acenaphthenyl, fluorenyl, phenanthryl, indenyl, pyrenyl, and biphenylyl), aromatic heterocyclic groups (e.g., pyridyl, pyrimidinyl, furyl, pyrrolyl, imidazolyl, benzimidazolyl, pyrazolyl, pyrazinyl, triazolyl (e.g., 1,2,4-triazol-1-yl or 1,2,3-triazol-1-yl), oxazolyl, benzoxazolyl, thiazolyl, isoxazolyl, isothiazolyl, furazanyl, thienyl, quinolyl, benzofuryl, dibenzofuryl, benzothienyl, dibenzothienyl, indolyl, carbazolyl, carbolinyl, diazacarbazolyl (i.e., a group prepared through replacement of one of the carbon atoms of the carboline ring of the carbolinyl group with a nitrogen atom), quinoxalinyl, pyridazinyl, triazinyl, quinazolinyl, and phthalazinyl), heterocyclic groups (e.g., pyrrolidyl, imidazolidinyl, morpholyl, and oxazolidyl), alkoxy groups (e.g., methoxy, ethoxy, propyloxy, pentyloxy, hexyloxy, octyloxy, and dodecyloxy), cycloalkoxy groups (e.g., cyclopentyloxy and cyclohexyloxy), aryloxy groups (e.g., phenoxy and naphthyloxy), alkylthio groups (e.g., methylthio, ethylthio, propylthio, pentylthio, hexylthio, octylthio, and dodecylthio), cycloalkylthio groups (e.g., cyclopentylthio and cyclohexylthio), arylthio groups (e.g., phenylthio and naphthylthio), alkoxycarbonyl groups (e.g., methyloxycarbonyl, ethyloxycarbonyl, butyloxycarbonyl, octyloxycarbonyl, and dodecyloxycarbonyl), aryloxycarbonyl groups (e.g., phenyloxycarbonyl and naphthyloxycarbonyl), sulfamoyl groups (e.g., aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, and 2-pyridylaminosulfonyl), acyl groups (e.g., acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl), acyloxy groups (e.g., acetyloxy, ethylcarbonyloxy, butylcarbonyloxy, octylcarbonyloxy, dodecylcarbonyloxy, and phenylcarbonyloxy), amido groups (e.g., methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, and naphthylcarbonylamino), carbamoyl groups (e.g., aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, and 2-pyridylaminocarbonyl), ureido groups (e.g., methylureido, ethylureido, pentylureido, cyclohexylureido, octylureido, dodecylureido, phenylureido, naphthylureido, and 2-pyridylaminoureido), sulfinyl groups (e.g., methylsulfinyl, ethylsulfinyl, butylsulfinyl, cyclohexylsulfinyl, 2-ethylhexylsulfinyl, dodecylsulfinyl, phenylsulfinyl, naphthylsulfinyl, and 2-pyridylsulfinyl), alkylsulfonyl groups (e.g., methylsulfonyl, ethylsulfonyl, butylsulfonyl, cyclohexylsulfonyl, 2-ethylhexylsulfonyl, and dodecylsulfonyl), arylsulfonyl and heteroarylsulfonyl groups (e.g., phenylsulfonyl, naphthylsulfonyl, and 2-pyridylsulfonyl), amino groups (e.g., amino, ethylamino, dimethylamino, diphenylamino, butylamino, cyclopentylamino, 2-ethylhexylamino, dodecylamino, aniline, naphthylamino, and 2-pyridylamino), halogen atoms (e.g., fluorine, chlorine, and bromine), fluorohydrocarbon groups (e.g., fluoromethyl, trifluoromethyl, pentafluoroethyl, and pentafluorophenyl), cyano groups, nitro groups, hydroxy groups, mercapto groups, and silyl groups (e.g., trimethylsilyl, triisopropylsilyl, triphenylsilyl, and phenyldiethylsilyl), and a phosphono group. Preferred are alkyl groups, aromatic hydrocarbon groups, aromatic heterocyclic groups, alkoxy groups, amino groups, and cyano groups.

Any of these substituents may further be substituted by the substituent described above. These substituents may be bonded together to form a ring.

If $R_b$, $R_c$, $R_d$, $R_{21}$, $R_{22}$, $R_{23}$, $R_{24}$, $R_{25}$, $R_{26}$, $R_{31}$, $R_{32}$, $R_{33}$, $R_{34}$, $R_{35}$, $R_{36}$, $R_{37}$, $R_{38}$, $R_e$, $R_{41}$, $R_{51}$, $R_{52}$, $R_{53}$, $R_{54}$, $R_{55}$, or $R_5$ in General formulae (2) to (5) described below represent a substituent, examples of the substituent include the aforementioned substituents which has been exemplified as a substituent for $R_{11}$, $R_{12}$, $R_{13}$, $R_{14}$, $R_{15}$, $R_{16}$, $R_{17}$, $R_{18}$, $R_{19}$, and $R_{20}$.

[Compound Represented by General Formula (2)]

The structure represented by General formula (A) described above is preferably represented by General formula (2) described below.

[Chem 14]

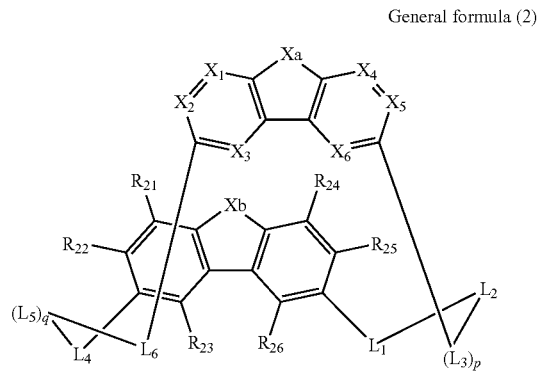

General formula (2)

In General formula (2), $X_a$ and $X_b$ each independently represent an oxygen atom, a sulfur atom, or $NR_c$. $X_1$, $X_2$, $X_3$, $X_4$, $X_5$, and $X_6$ each independently represent a nitrogen atom or $CR_d$ and at least one of $X_1$, $X_2$, $X_3$, $X_4$, $X_5$, and $X_6$ is a nitrogen atom. $R_c$, $R_d$, $R_{21}$, $R_{22}$, $R_{23}$, $R_{24}$, $R_{25}$, and $R_{26}$ each independently represent a hydrogen atom or a substituent. $L_1$, $L_2$, $L_3$, $L_4$, $L_5$, and $L_6$ each represent a divalent linkage group. p and q each represent an integer of 0 or 1.

If $X_a$ and $X_b$ each represent $NR_c$, they may be bonded together to form a ring.

[Compound Represented by General Formula (3)]

The structure represented by General formula (A) described above is preferably represented by General formula (3) described below.

[Chem 15]

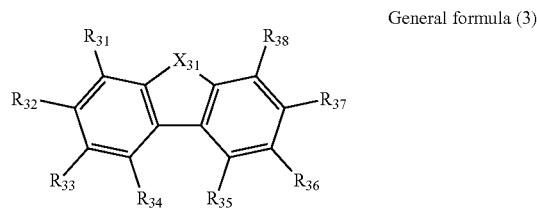

General formula (3)

In General formula (3), $X_{31}$ represents $PR_b(\!=\!O)$, $SO_2$, or SO. $R_b$, $R_{31}$, $R_{32}$, $R_{33}$, $R_{34}$, $R_{35}$, $R_{36}$, $R_{37}$, and $R_{38}$ each independently represent a hydrogen atom or a substituent. At least one of $R_{31}$, $R_{33}$, $R_{36}$, and $R_{38}$ is represented by General formula (3-A) described below.

[Chem 16]

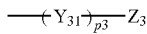

General formula (3-A)

In General formula (3-A), $Y_{31}$ represents a divalent linkage group, $Z_3$ represents an electron-donating aromatic hydrocarbon or heteroaromatic group. p3 represents an integer of 0 or 1.

[Compound Represented by General Formula (4)]

The structure represented by General formula (A) described above is preferably represented by General formula (4) described below.

[Chem 17]

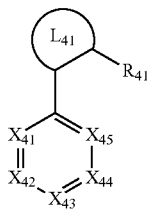

General formula (4)

In General formula (4), $X_{41}$, $X_{42}$, $X_{43}$, $X_{44}$, and $X_{45}$ each independently represent a nitrogen atom or $CR_e$. $R_e$ represents a hydrogen atom or a substituent. $L_{41}$ represents an aromatic hydrocarbon group or a heteroaromatic group. At least one of $R_{41}$ is represented by General formula (4-A) described below.

[Chem 18]

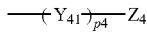

General formula (4-A)

In General formula (4-A), $Y_{41}$ represents a divalent linkage group, $Z_4$ represents an electron-donating aromatic hydrocarbon or heteroaromatic group, and p4 represents an integer of 0 or 1.

The structure represented by General formula (A) described above is preferably represented by General formula (5) described below. In General formula (5), $R_{51}$, $R_{52}$, $R_{53}$, $R_{54}$, $R_{55}$, and $R_{56}$ each independently represent a hydrogen atom or a substituent. In General formula (5), $Z_{51}$ and $Z_{52}$ each independently represent an electron-donating aromatic hydrocarbon or heteroaromatic group or an electron-accepting aromatic hydrocarbon or heteroaromatic group, with the proviso that both $Z_{51}$ and $Z_{52}$ are not an electron-donating aromatic hydrocarbon or heteroaromatic group and that both $Z_{51}$ and $Z_{52}$ are not an electron-accepting aromatic hydrocarbon or heteroaromatic group.

[Chem 19]

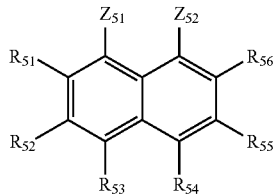

General formula (5)

The substituent, aromatic hydrocarbon group, and heteroaromatic group in General formulae (2) to (5) have the same definition as those in General formula (1).

In General formula (1-A), (1-B), (2), (3-A), and (4-A), examples of the divalent linkage group represented by $Y_{11}$, $Y_{12}$, $L_1$, $L_2$, $L_3$, $L_4$, $L_5$, $L_6$, $Y_{31}$, and $Y_{41}$ include a chalcogen atom such as oxygen or sulfur, an dialkylsilyl group, an alkylene group (for example, an ethylene group, a trimethylene group, a tetramethylene group, a propylene group, an ethylethylene group, a pentamethylene group, a hexamethylene group, a 2,2,4-trimethylhexamethylene group, a heptamethylene group, an octamethylene group, nonamethylene group, a decamethylene group, an undecamethylene group, a dodecamethylene group, a cyclohexylene group (for example, a 1,6-cyclohexanediyl group) and a cyclopenthylene group (for example, a 1,5-cyclopentanediyl group)); an alkenylene group (for example, a vinylene group, a propenylene group, a butenylene group, a pentenylene group, a 1-methylvinylene group, a 1-methylpropenylene group, a 2-methylpropenylene group, a 1-methylpentenylene group, a 3-methylpentenylene group, a 1-ethylvinylene group, a 1-ethylpropenylene group, a 1-ethylbutenylene group and a 3-ethylbutenylene group); an alkynylene group (for example, an ethynylene group, a 1-propynylene group, a 1-butynylene group, a 1-pentynylene group, a 1-hexynylene group, a 2-butynylene group, a 2-pentynylene group, a 1-methylethynylene group, a 3-methyl-1-propynylene group and a 3-methyl-1-butynylene group); an arylene group (for example, an o-phenylene group, a p-phenylene group, a naphthalenediyl group, an anthracenediyl group, a naphthacenediyl group, a pyrenediyl group, a naphthylnaphthalenediyl group, a biphenyldiyl group (for example, a [1,1'-biphenyl]-4,4'-diyl group, a 3,3'-biphenyldiyl group and a 3,6-biphenyldiyl group), a terphenyldiyl group, a quaterphenyldiyl group, a quinquephenyldiyl group, a sexiphenyldiyl group, a septiphenyldiyl group, an octiphenyldiyl group, a nobiphenyldiyl group and a deciphenyldiyl group); a heteroarylene group (for example, a divalent group derived from a group consisting of a carbazole group, a carboline ring, a diazacarbazole ring (also called a monoazacarboline group, indicating a ring formed in such a manner that one of carbon atoms constituting a carboline ring is substituted by a nitrogen atom), a triazole ring, a pyrrole ring, a pyridine ring, a pyrazine ring, a quinoxaline ring, a thiophene ring, an oxadiazole ring, a dibenzofuran ring, a dibenzothiophene ring and an indole ring), and and a group derived from a condensed aromatic heterocycle formed in such a manner that three or more rings are condensed (the condensed aromatic heterocycle formed in such a manner that three or more rings are condensed preferably contains a hetero atom selected from N, O and S as an element constituting a condensed ring; for example, an acridine ring, a benzoquinoline ring, a carbazole ring, a phenazine ring, a phenanthridine ring, a phenanthroline ring, a carboline ring, a cycladine ring, a quindoline ring, a thebenidine ring, a quinindoline ring, a triphenodithiazine ring, a triphenodioxazine ring, a phenanthrazine ring, an anthrazine ring, a perimizine ring, a diazacarbazole ring (indicating a ring formed in such a manner that one of carbon atoms constituting a carboline ring is substituted by a nitrogen atom), a phenanthroline ring, a dibenzofuran ring, a dibenzothiophene ring, a naphthofuran ring, a naphthothiophene ring, a benzodifuran ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring and a thiophanthrene ring (naphthothiophene ring)).

The molecular weight of π-conjugated compounds described above is preferably 2000 or less, in view of easy formation of a film. Specific examples of π-conjugated compounds described above include compounds described below.

<Exemplary Compound>

[Chem 20]

1

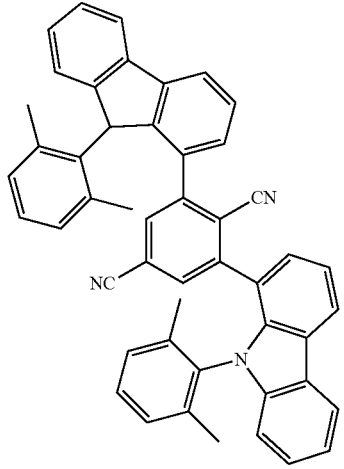

2

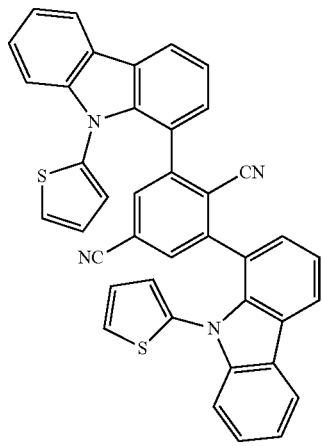

3

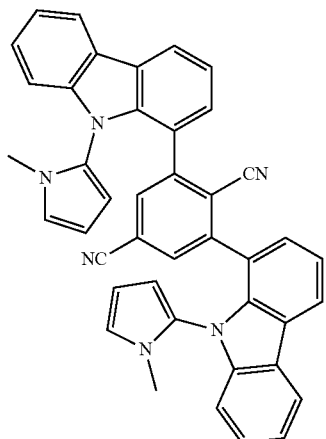

4

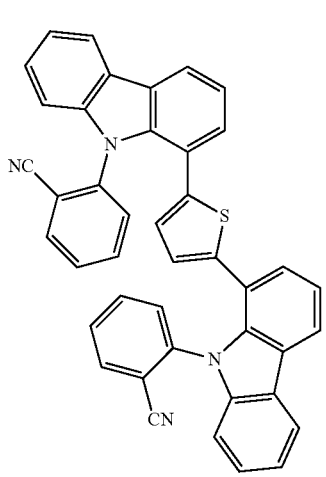

5

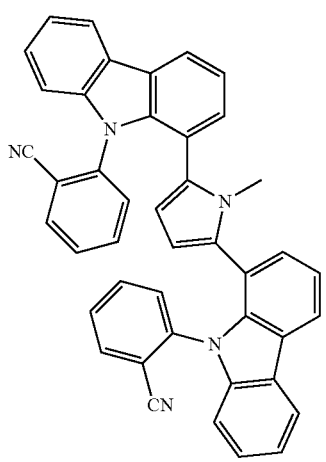

6

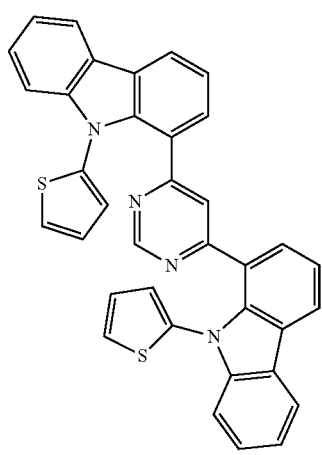

-continued
7
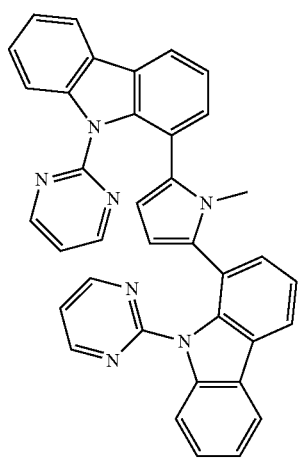
8
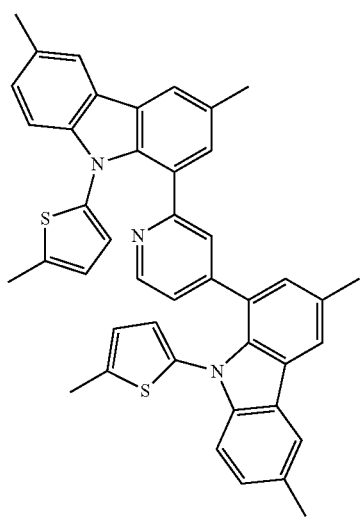
9
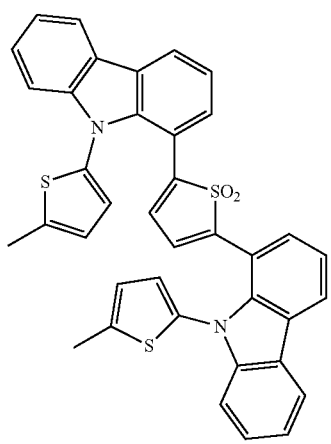
[Chem 21]
10
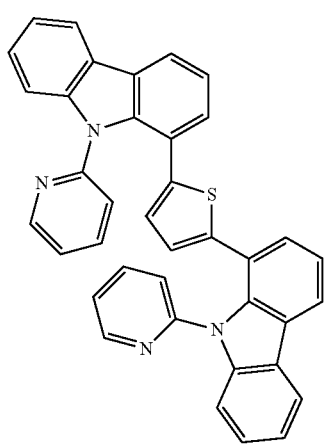
11
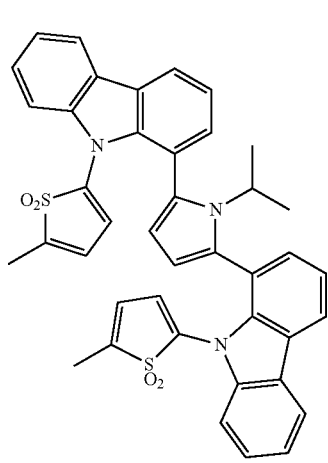

-continued
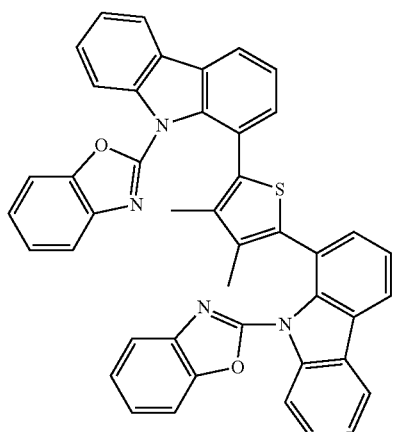
12
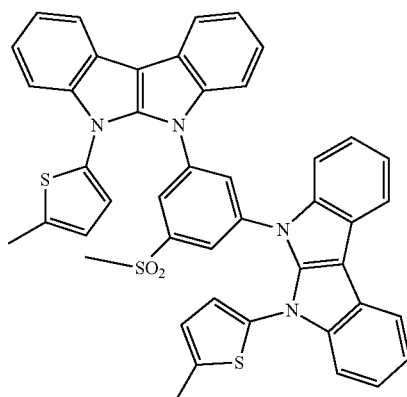
13
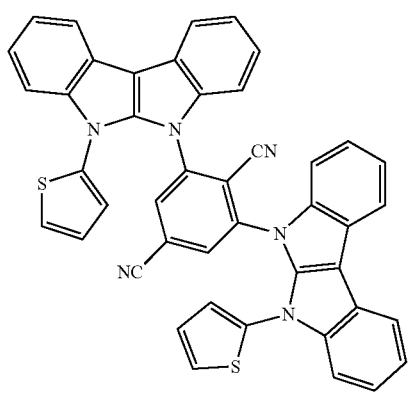
14
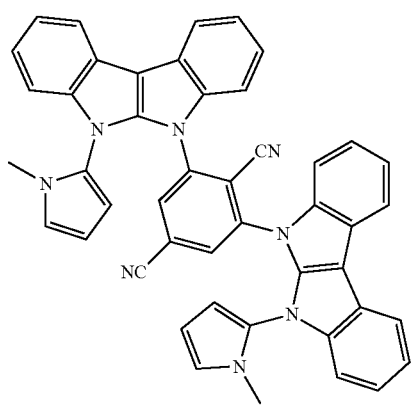
15
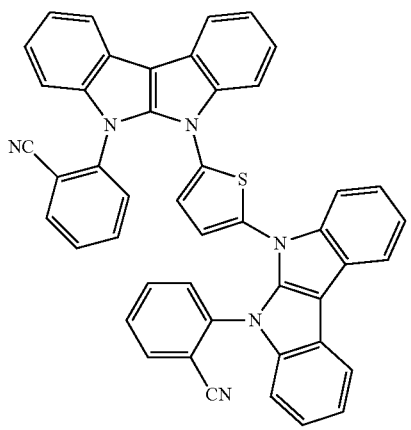
16
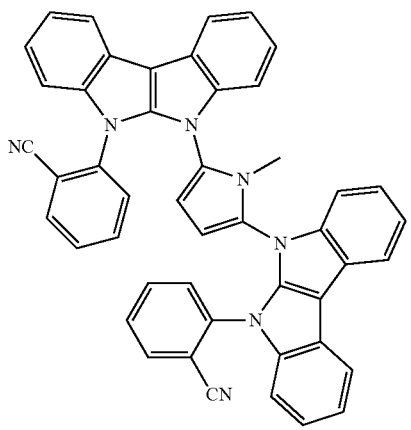
17
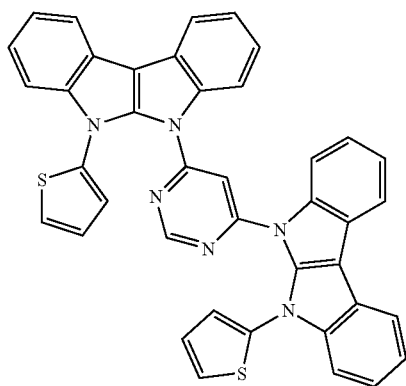
18

[Chem 22]
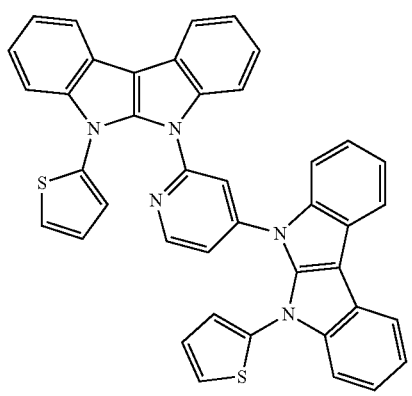
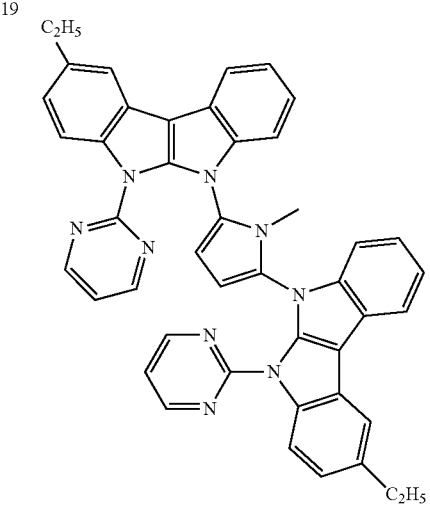
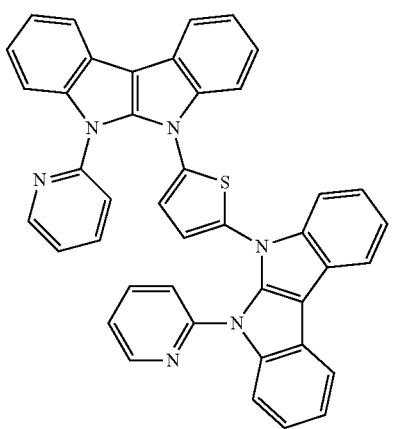
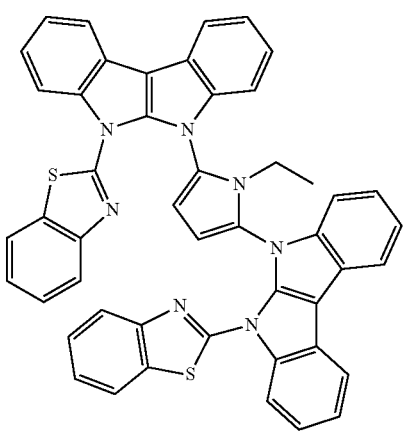

-continued
[Chem 23]
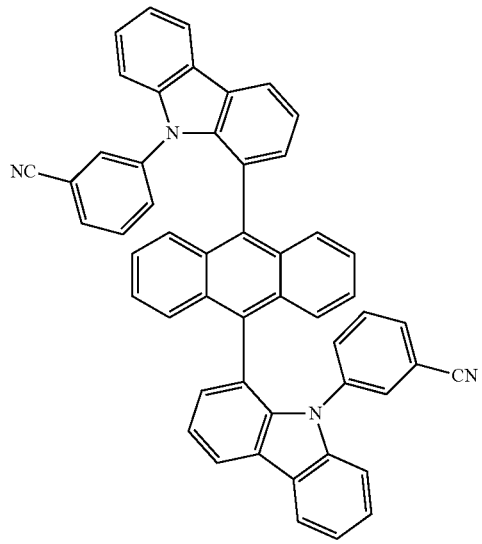
25
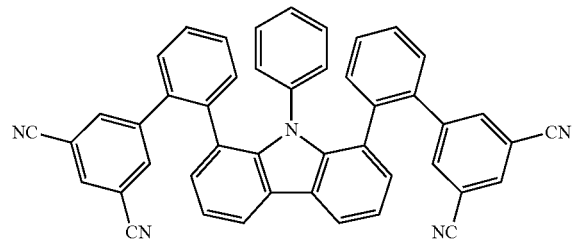
26
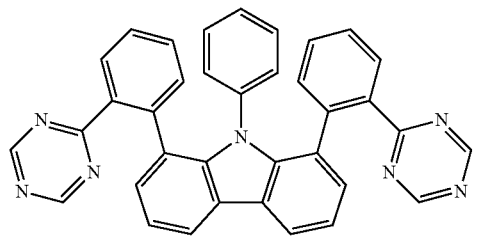
27
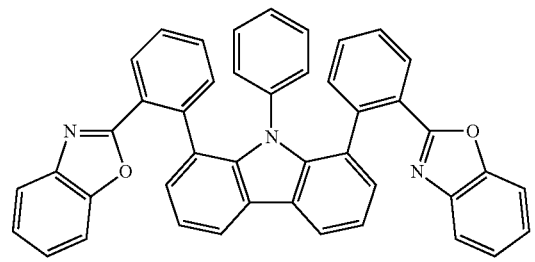
28
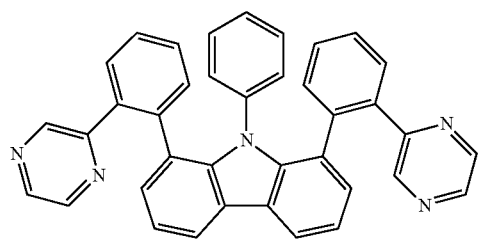
29
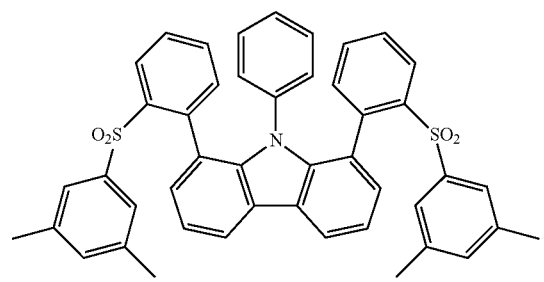
30
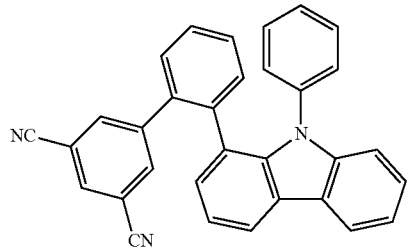
31
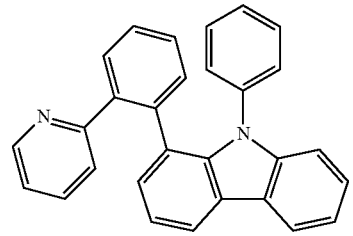
32

-continued
33
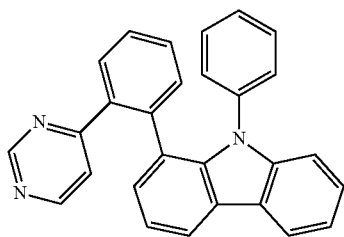
34
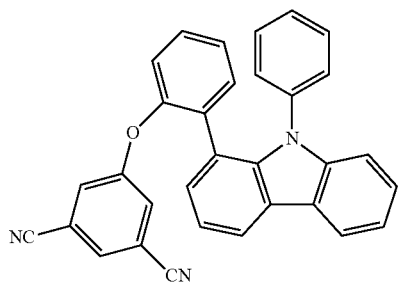
35
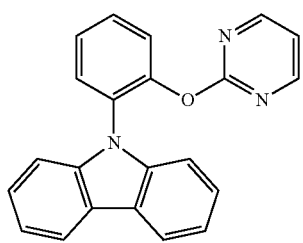
36
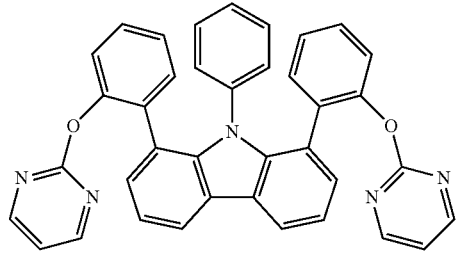
[Chem 24]
37
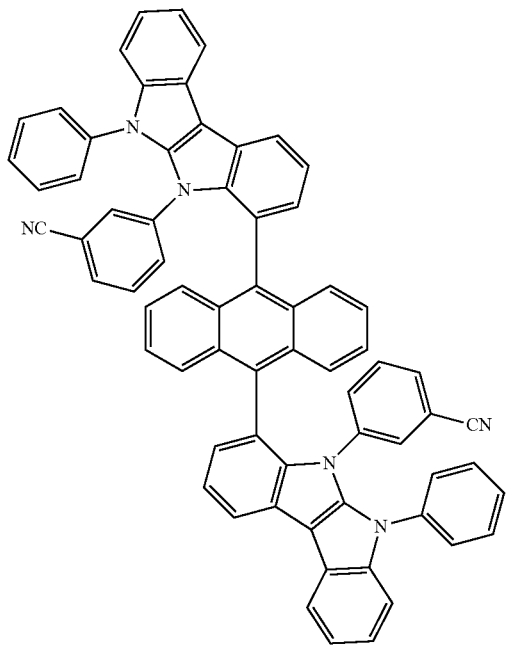
38
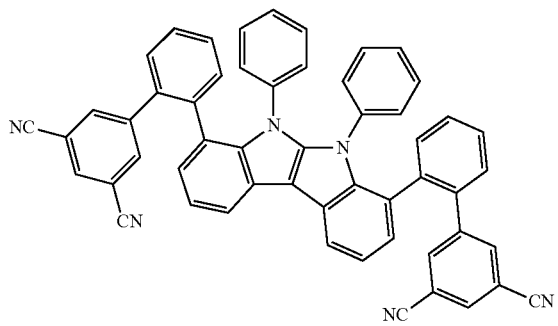

-continued
39
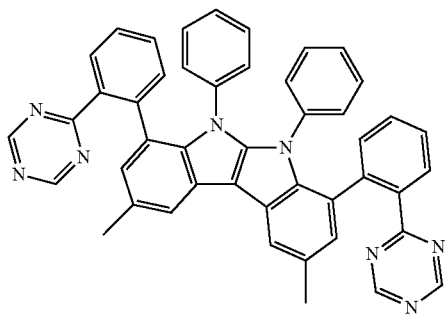
40
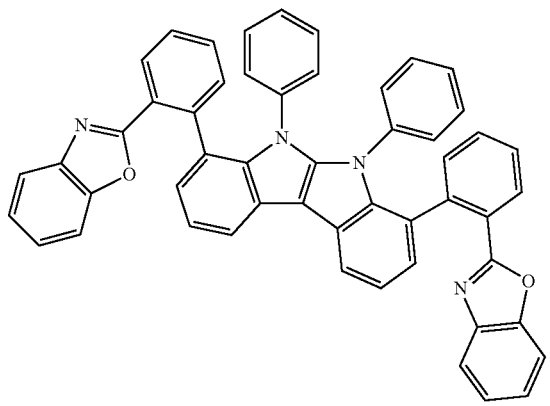
41
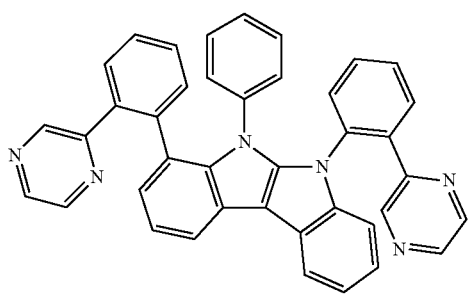
42
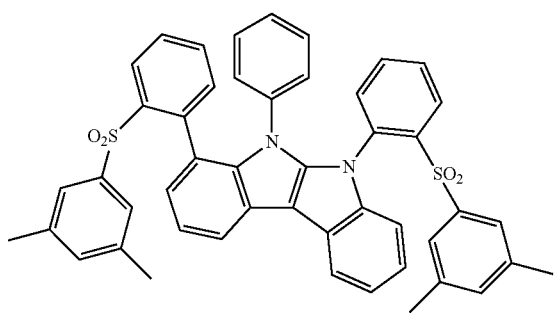
44
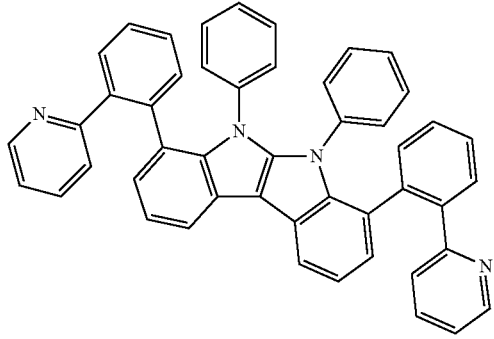
45
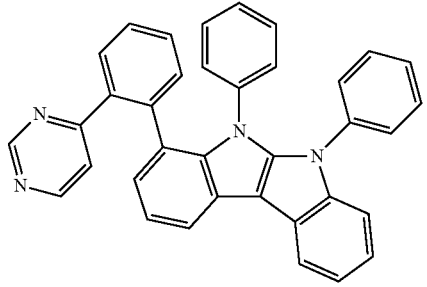
[Chem 25]
46
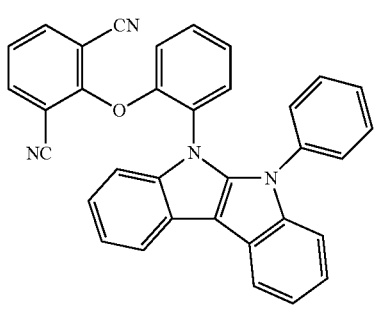
47
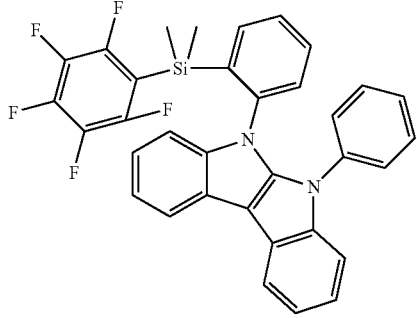

-continued
48
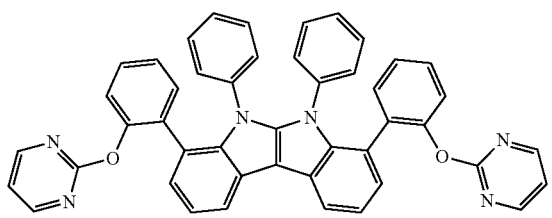
49
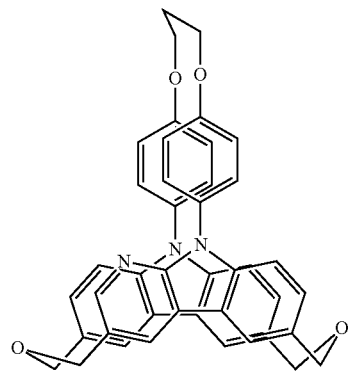
50
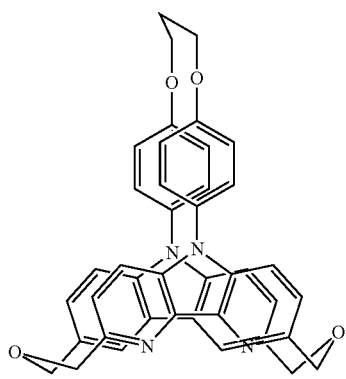
51
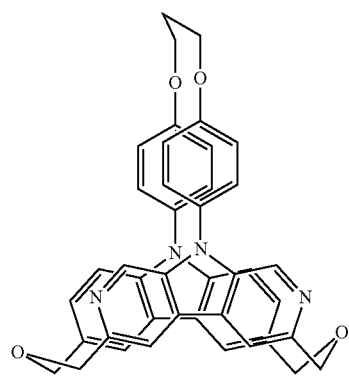
52
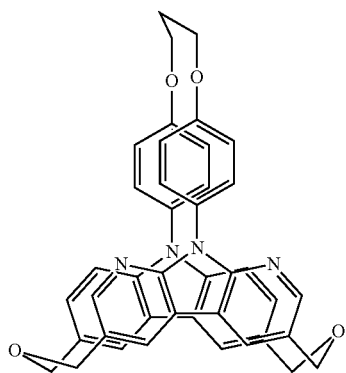
53
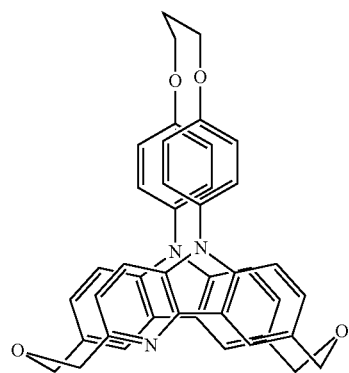
54
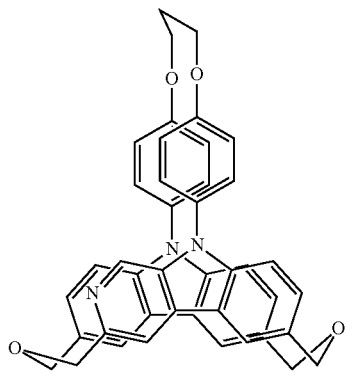
55
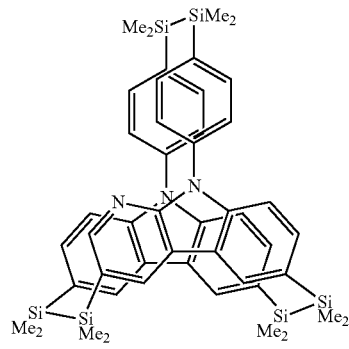

-continued
56 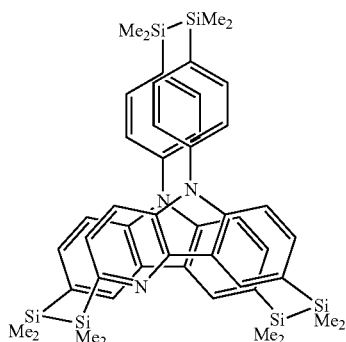
57 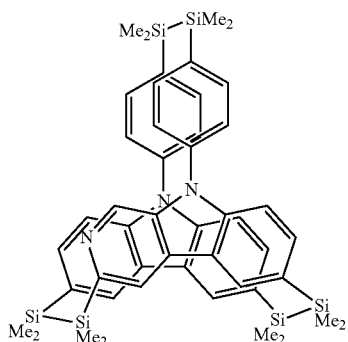
[Chem 26]
58 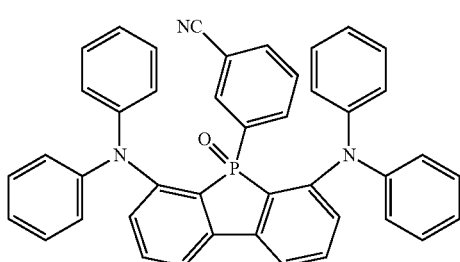
59 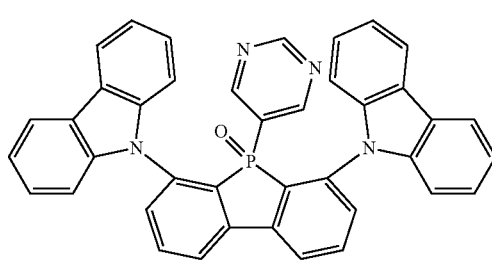
60 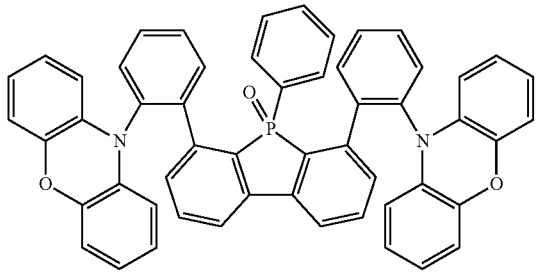
61 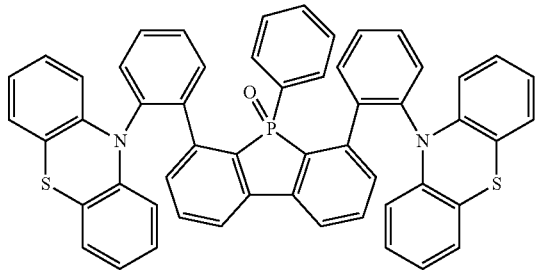
62 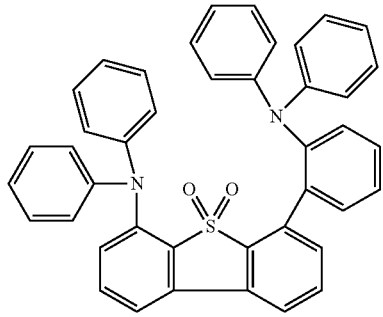
63 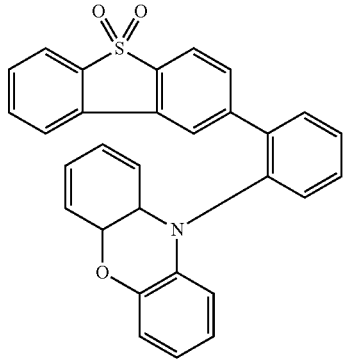
64 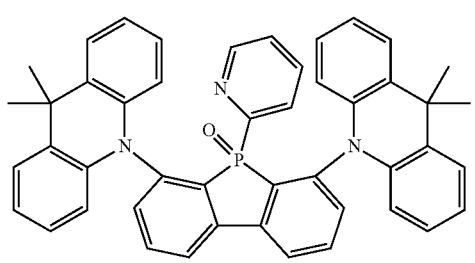
65 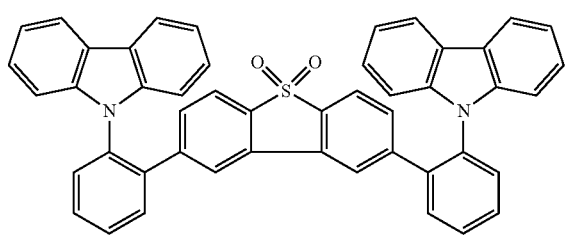

-continued
66
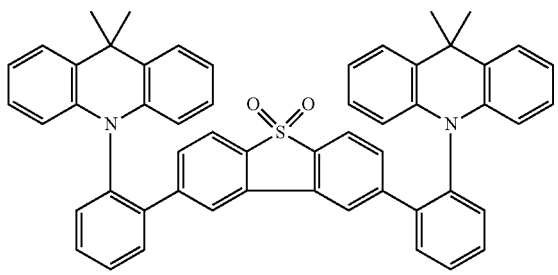
67
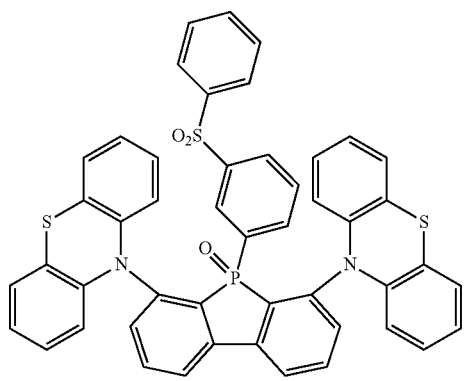
[Chem 27]
68
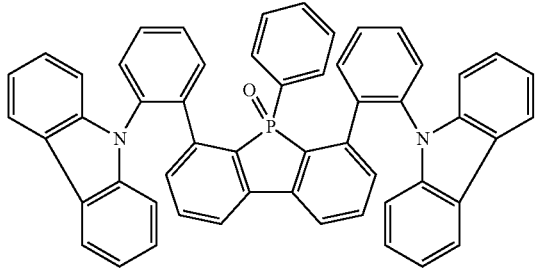
69
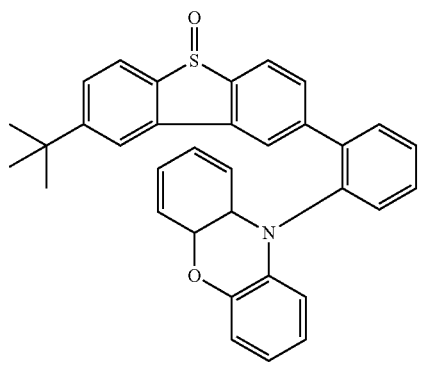
70
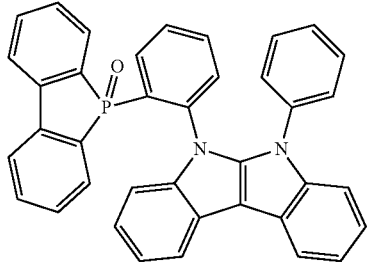
71
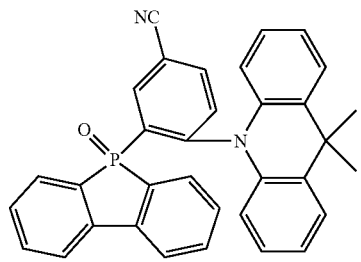
72
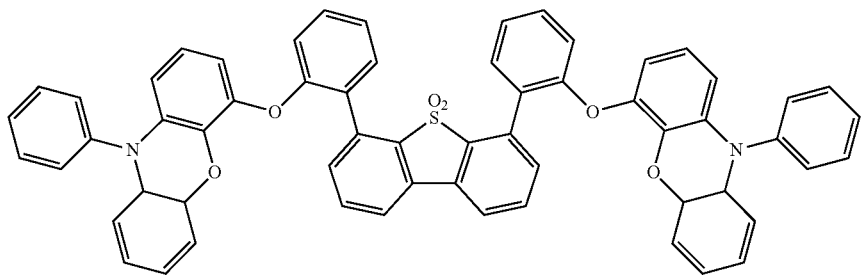

73
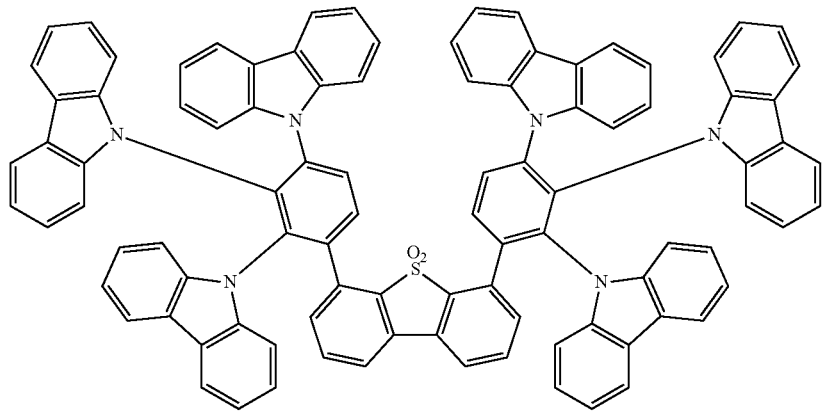
74
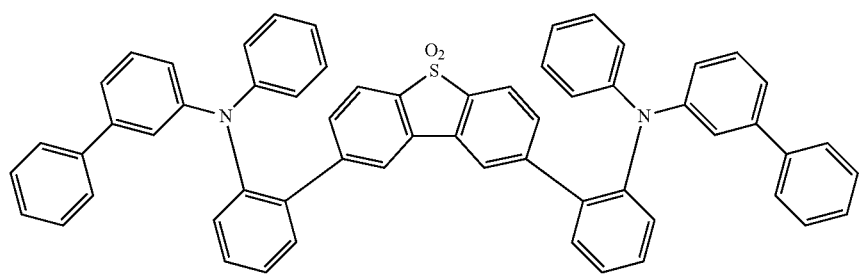
[Chem 28]
75
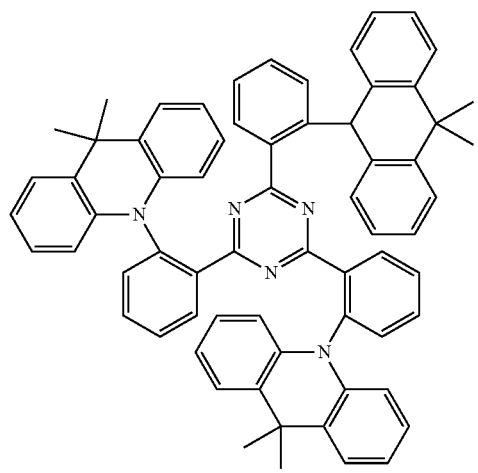
76
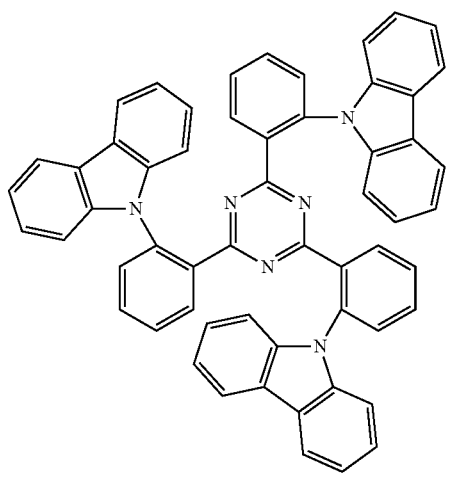
77
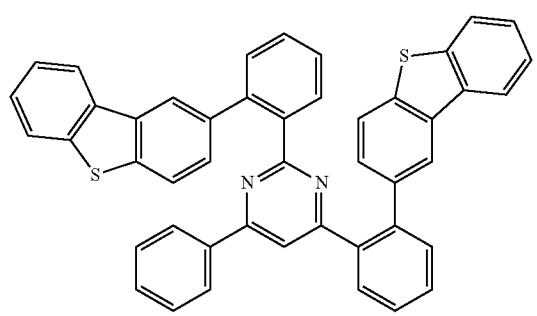
78
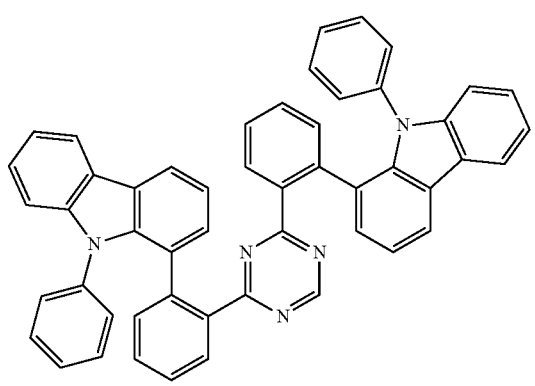

-continued
79
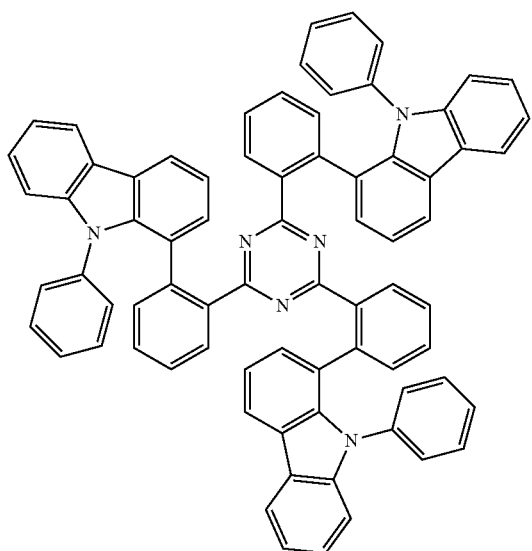
80
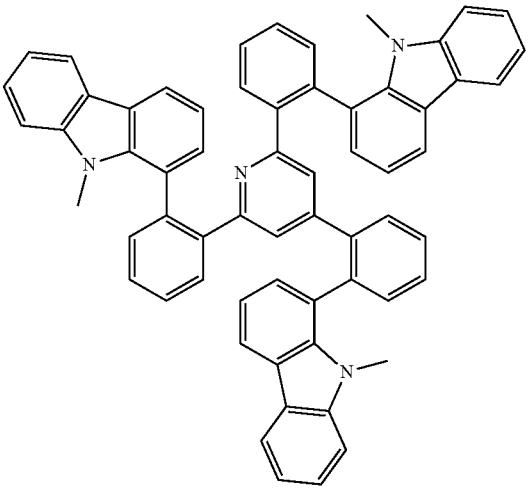
81
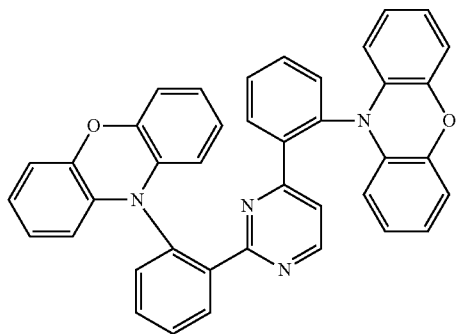
[Chem 29]
82
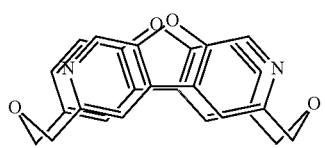
83
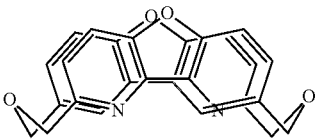
84
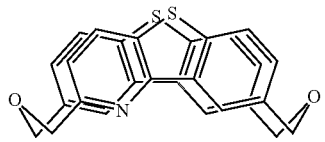
85
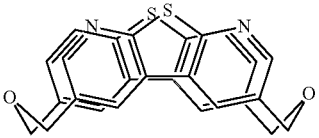
86
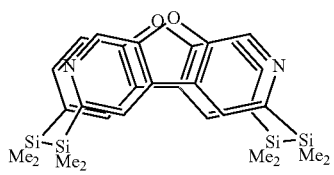
87
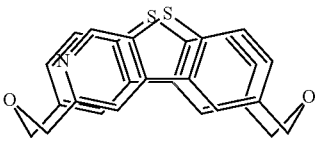
88
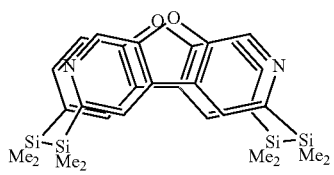
89
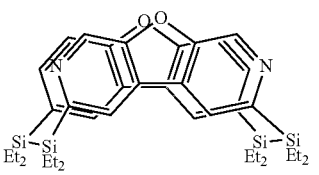

-continued
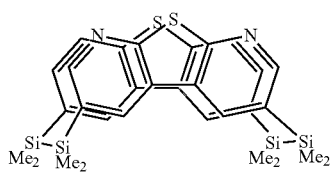
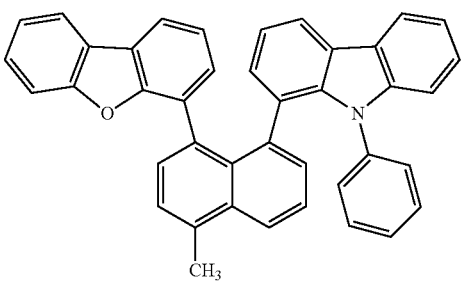
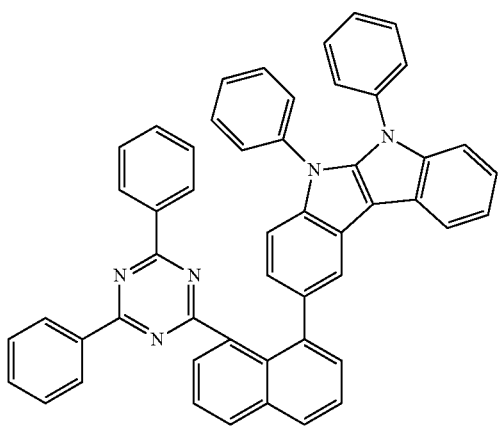
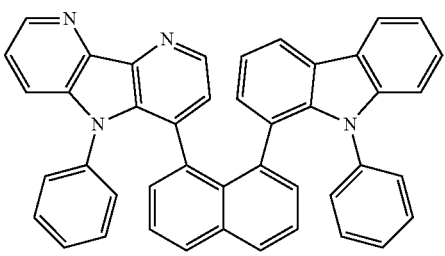
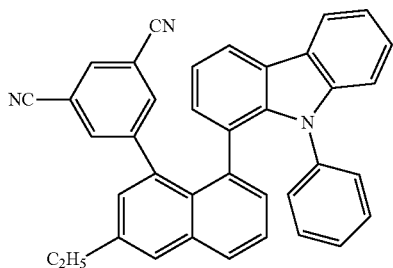
[Chem 30]
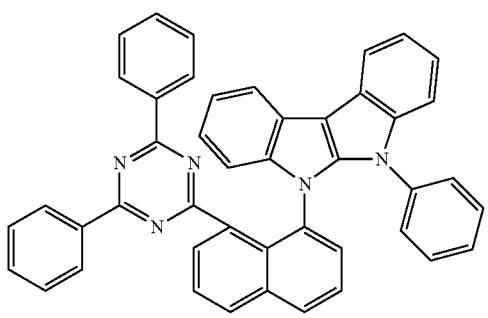

96

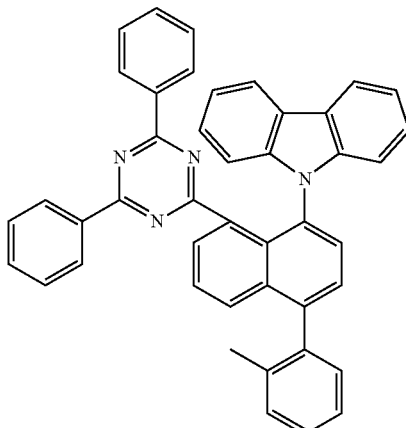

97

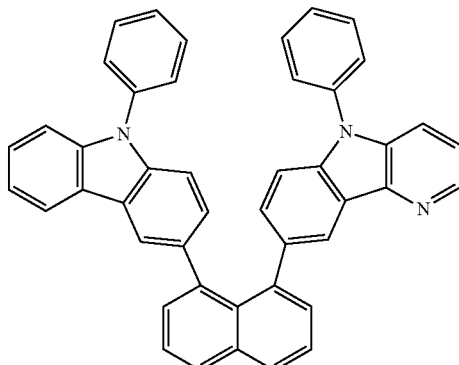

98

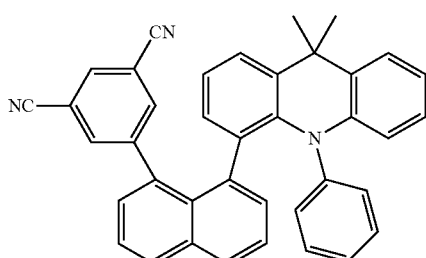

99

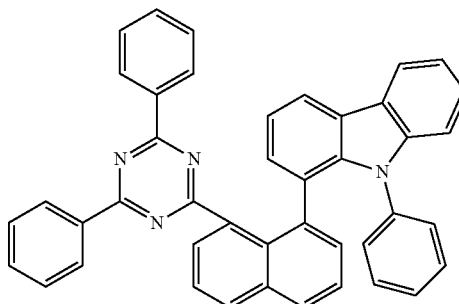

100

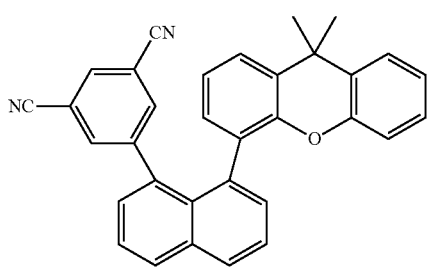

101

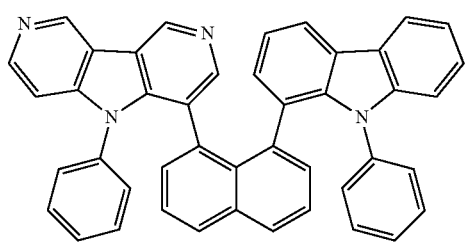

<Method of Synthesization>

The π-conjugated compound described above can be synthesized by referring to the method described in the following documents or in the documents cited in the following documents.
(1) S. Riedmuller and Boris J Nachtsheim., Beilstein J. Org. Chem. 2013, 9, 1202-1209
(2) Wako Organic Square No. 27 (2009)
(3) N. M. Moazzam et al., Appl. Organomet. Chem., 2012, 26, 7, 330-334
(4) H. Kawai, et al., Chemical Communication, 2008, 12, 1464-1466
(5) S. Oi, et al., Tetrahedron, 2008, 64, 26, 6051-6059
(6) S. Oi, et al., Organic Letters, 2008, 10, 9, 1832-1826
(7) H. Uoyama, et al., Nature, 2012, 492, 234-238 (NPL 2 described above)
(8) Y. Nakamura, et al., Bull. Chem. Soc. Jpn., 2009, 82, 2743.

(Determination of Percent Electron Density)

The linkage moiety L exhibits a HOMO electron density of less than 10%. This indicates that the electron density of the HOMO localized on the atoms of the moiety L is less than 10% relative to the total HOMO electron density (taken as 100%) obtained through molecular orbital calculation. The expression "moiety L exhibits an electron density of less than 10%" indicates almost no electron density distribution on the moiety.

The percent electron density was determined as described below. The structure of a target molecule in a stable ground state was determined through calculation by Gaussian 09 using DFT (B3LYP/6-31G*) (keywords: # p and pop=regular), to output molecular orbitals (HOMO and LUMO). The electron density is determined through analysis of the electron density distribution of the HOMO. In detail, the percentages of carbon atoms and heteroatoms corresponding to the moiety L were calculated on the basis of the sum of the squares of the coefficients of all the atoms corresponding to the HOMO.

The LUMO can be analyzed as in the HOMO. The moiety L also exhibits a LUMO electron density of less than 10%. This indicates that the electron density of the LUMO localized on carbon atoms and heteroatoms of the moiety L is less than 10% relative to the total LUMO electron density (taken as 100%) obtained through molecular orbital calculation.

(Determination of the Distance r Between the Centroids of Orbitals)

As used herein, the "distance r" is defined as the spatial distance between the centroids of different two molecular orbitals. In the present invention, the distance r between the centroids of the HOMO and the LUMO of a molecule was determined as described below. The structure of a target molecule in a stable ground state was determined through calculation by Gaussian 09 using DFT (B3LYP/6-31G*). The coordinates of the centroid of the HOMO or the LUMO are determined on the basis of the dipole moment matrix and the HOMO or LUMO vector obtained through the calculation for the molecular structure. The dipole moment matrix was determined in the ground state through single-point energy calculation using DFT (B3LYP/6-31G*) (keyword: iop(3/33=1)). The difference in centroid coordinates between the HOMO and the LUMO ($\Delta x$, $\Delta y$, $\Delta z$) and the value ($r=(\Delta x+\Delta y+\Delta z)^{1/2}$) were calculated to determine the distance r between the centroids of these orbitals. If two or more moieties D or A are present, the distance r is determined between the centroids of the HOMO having the maximum electron density and the LUMO having the maximum electron density.

(Determination of the Probability of Electron Transition)

The probability of electron transition from the HOMO to the LUMO was determined through TDDFT calculation using Gaussian 09 as described below in detail. The structure of a target molecule in a stable ground state was determined through calculation by Gaussian 09 using DFT (B3LYP/6-31G*). The structure was subjected to TDDFT calculation using the same functional and basis function (keyword: TD(nstates=3, TD=50-50)) to determine the probability of electron transition. The probability of electron transition in the lowest singlet excited state was determined by squaring the output coefficient corresponding to electron transition from the HOMO to the LUMO and doubling the squared value.

(Determination of Angle $\theta_{DA}$)

FIG. 3 schematically illustrates an angle $\theta_{DA}$ in a π-conjugated compound having a structure represented by General formula (A).

In General formula (A), D represents an electron-donating moiety on which the HOMO is localized, A represents an electron-accepting moiety on which the LUMO is localized, and L represents a linkage moiety that connects the moieties D and A.

The angle $\theta_{DA}$ of exemplary compound 46 will now be described with reference to FIG. 3. In this case, the angle $\theta_{DA}$ is defined as an angle θ formed by straight line X connecting the centroid (★) Gd of the HOMO on the electron-donating moiety D and the centroid Ld of the atom of the linkage moiety L adjacent to the electron-donating moiety D (i.e., the carbon atom of the benzene ring) and straight line Y connecting the centroid (★) Ga of the LUMO on the electron-accepting moiety A and the centroid La of the atom of the linkage moiety L adjacent to the electron-accepting moiety A (i.e., the oxygen atom of the substituent on the benzene ring) in the most stable ground state.

In the present invention, the angle $\theta_{DA}$ is determined as described below.

The inner product of X and Y (=X·Y) and the absolute values of X and Y (|X| and |Y|) were determined, and the angle $\theta_{DA}$ was calculated by the following expression:

$$\cos \theta_{DA}=(X \cdot Y)/(|X| \times |Y|)$$

where X and Y represent the vectors of straight lines X and Y, respectively.

Figure 4:
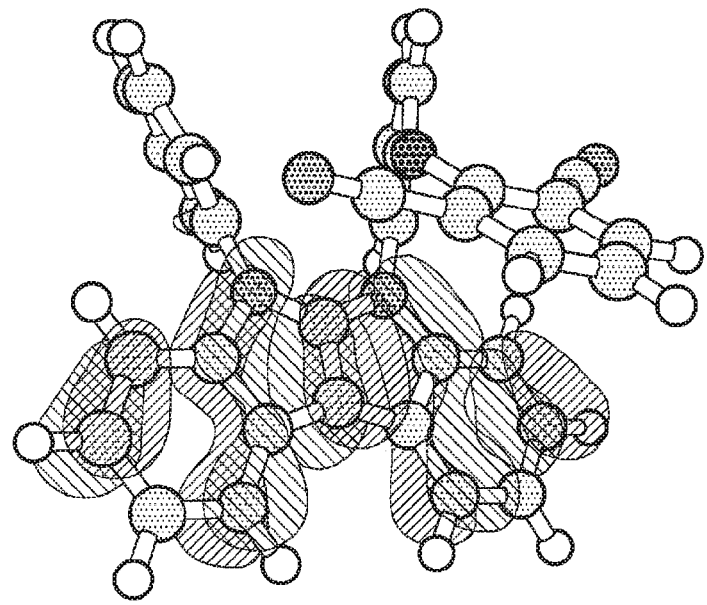
FIG. 4 is an illustration of the electron densities of the HOMO on an electron-donating moiety D and the LUMO on an electron-accepting moiety A.
Figure 4:
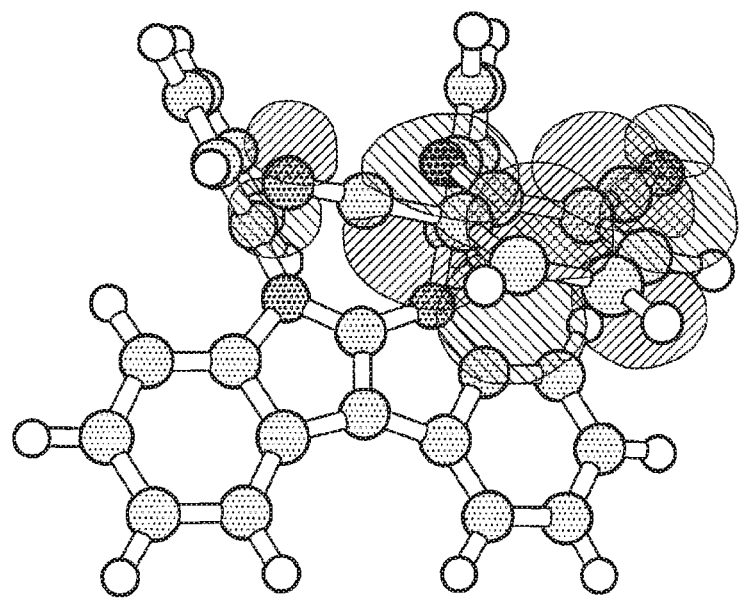

FIG. 4 is a schematic illustration of the electron density distribution of the HOMO on an electron-donating moiety D of exemplary compound 46 (FIG. 4a) and the electron density distribution of the LUMO on an electron-accepting moiety A of the compound (FIG. 4b). FIG. 4 illustrates no overlap (i.e., separation) of these electron density distributions.

Figure 5:
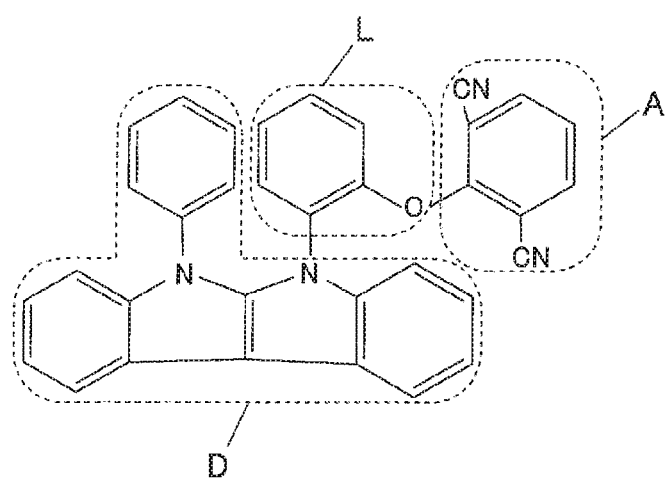
FIG. 5 is an illustration of an electron-donating moiety D, an electron-accepting moiety A, and a linkage moiety L of exemplary compound 46.

FIG. 5 is a schematic illustration of an electron-donating moiety D, an electron-accepting moiety A, and a linkage moiety L of exemplary compound 46, which are respectively enclosed by broken lines.

(1.2) Fluorescent Compound

The luminous material used in the present invention may be any known fluorescent compound. The fluorescent compound may be the π-conjugated compound according to the present invention.

Examples of the known fluorescent compound include compounds exhibiting high fluorescence quantum yield, such as coumarin dyes, pyran dyes, cyanine dyes, croconium dyes, squarylium dyes, oxobenzanthracene dyes, fluorescein dyes, rhodamine dyes, pyrylium dyes, perylene dyes, stilbene dyes, polythiophene dyes, fluorescent rare earth complexes, and laser dyes.

(1.3) Phosphorescent Dopant

The phosphorescent dopant used in the present invention emits light from the excited triplet state. In detail, the phosphorescent dopant is defined as a compound that emits phosphorescent light at room temperature (25° C.) and has a phosphorescent quantum yield of 0.01 or more at 25° C. The preferred phosphorescent quantum yield is 0.1 or more.

The phosphorescent quantum yield is determined by the method described in page 398 of *Bunko II of Jikken Kagaku Koza* 7 (Spectroscopy II, Experimental Chemistry 7) (4th Edition, 1992, published by Maruzen Company, Limited). The phosphorescent quantum yield in a solution can be determined with any appropriate solvent. The phosphorescent dopant used in the present invention has a phosphorescent quantum yield of 0.01 or more determined with any appropriate solvent.

The phosphorescent dopant may be appropriately selected from known ones used for the luminous layer of an organic EL element. Specific examples of known phosphorescent dopants usable in the present invention include those described in the following publications.

Nature, 395, 151 (1998), Appl. Phys. Lett., 78, 1622 (2001), Adv. Mater. 19, 739 (2007), Chem. Mater., 17, 3532 (2005), Adv. Mater., 17, 1059 (2005), International Patent Publication WO2009/100991, WO2008/101842, and WO2003/040257, U.S. Patent Application Publication Nos. 2006/835469, 2006/0202194, 2007/0087321, and 2005/0244673, Inorg. Chem., 40, 1704 (2001), Chem. Mater., 16, 2480 (2004), Adv. Mater., 16, 2003 (2004), Angew. Chem. Int. Ed., 2006, 45, 7800, Appl. Phys. Lett., 86, 153505 (2005), Chem. Lett., 34, 592 (2005), Chem. Commun., 2906 (2005), Inorg. Chem., 42, 1248 (2003), International Patent Publication WO2009/050290, WO2002/015645, and WO2009/000673, U.S. Patent Application Publication No. 2002/0034656, U.S. Pat. No. 7,332,232, U.S. Patent Application Publication Nos. 2009/0108737 and 2009/0039776, U.S. Pat. Nos. 6,921,915 and 6,687,266, U.S. Patent Application Publication Nos. 2007/0190359, 2006/0008670, 2009/0165846, and 2008/0015355, U.S. Pat. Nos. 7,250,226 and 7,396,598, U.S. Patent Application Publication Nos. 2006/0263635, 2003/0138657, and 2003/0152802, U.S. Pat. No. 7,090,928, Angew. Chem. Int. Ed., 47, 1 (2008), Chem. Mater., 18, 5119 (2006), Inorg. Chem., 46, 4308 (2007), Organometallics, 23, 3745 (2004), Appl. Phys. Lett., 74, 1361 (1999), International Patent Publication WO2002/002714, WO2006/009024, WO2006/056418, WO2005/019373, WO2005/123873, WO2005/123873, WO2007/004380, and WO2006/082742, U.S. Patent Application Publication Nos. 2006/0251923 and 2005/0260441, U.S. Pat. Nos. 7,393,599, 7,534,505, and 7,445,855, U.S. Patent Application Publication Nos. 2007/0190359 and 2008/0297033, U.S. Pat. No. 7,338,722, U.S. Patent Application Publication No. 2002/0134984, U.S. Pat. No. 7,279,704, U.S. Patent Application Publication Nos. 2006/098120 and 2006/103874, International Patent Publication WO2005/076380, WO2010/032663, WO2008/140115, WO2007/052431, WO2011/134013, WO2011/157339, WO2010/086089, WO2009/113646, WO2012/020327, WO2011/051404, WO2011/004639, and WO2011/073149, U.S. Patent Application Publication Nos. 2012/228583 and 2012/212126, Japanese Unexamined Patent Application Publication No. 2012-069737, Japanese Patent Application No. 2011-181303, and Japanese Unexamined Patent Application Publication Nos. 2009-114086, 2003-81988, 2002-302671, and 2002-363552.

The phosphorescent dopant is preferably an organometallic complex containing Ir as a central metal, more preferably a complex containing at least one coordination mode of metal-carbon bond, metal-nitrogen bond, metal-oxygen bond, and metal-sulfur bond.

(2) Host Compound

In the present invention, the host compound is used for injection and transportation of carriers in the luminous layer. The host compound emits substantially no light in the organic EL element.

The host compound is preferably contained in the luminous layer in an amount of 20 mass % or more.

Host compounds may be used alone or in combination. The combined use of host compounds leads to control of electric charge transfer, resulting in high emission efficiency of the organic EL element.

Now will be described host compounds preferably used in the present invention.

Any host compound may be used in combination with the π-conjugated compound according to the present invention. In view of reverse energy transfer, the host compound preferably has an excited singlet energy level higher than that of the π-conjugated compound according to the present invention, and more preferably, the host compound has an excited triplet energy level higher than that of the π-conjugated compound according to the present invention.

In the luminous layer, the host compound transports carriers and generates excitons. Preferably, the host compound is stable in the state of any active chemical species (i.e., cationic radical state, anionic radical state, and excited state) and does not undergo any chemical change (e.g., decomposition or addition reaction). More preferably, molecules of the host compound do not migrate in the luminous layer on the order of angstrom during energization.

If the luminous dopant used in combination with the host compound exhibits TADF emission, the TADF compound is present in the triplet excited state for a long period of time, and thus appropriate molecular design is required for the host compound for preventing a reduction in $T_1$. Requirements for the molecular design include an increase in energy level $T_1$ of the host compound, prevention of low energy level $T_1$ of associated molecules of the host compound, no exciplex formation between the TADF compound and the host compound, and no electromer formation from the host compound by electric excitation.

In order to satisfy such requirements, the host compound needs to exhibit high electron hopping mobility and high hole hopping mobility, and to undergo a small change in structure in the triplet excited state. The host compound satisfying such requirements is preferably a compound partially having an extended π-conjugated structure (14-π-electron system) exhibiting high energy level $T_1$, such as a structure of carbazole, azacarbazole, dibenzofuran, dibenzothiophene, or azadibenzofuran. In particular, incorporation of a carbazole derivative into the luminous layer is preferred for appropriate promotion of carrier hopping and dispersion of the luminous material in the luminous layer, resulting in improved emission efficiency of the device and enhanced stability of the thin film.

Typical examples of the host compound include compounds having a biaryl and/or a multi-aryl ring structure. As used herein, the term "aryl" refers to both an aromatic hydrocarbon ring and an aromatic heterocyclic ring.

The host compound is more preferably a compound prepared by direct bonding between a carbazole structure and an aromatic heterocyclic compound having a 14-π-electron system and having a molecular structure different from the carbazole structure, still more preferably a carbazole derivative having, in the molecule, two or more aromatic heterocyclic rings having a 14-π-electron system. In particular, the carbazole derivative is preferably a compound having two or more conjugated structures each having 14 or more π-electrons for further enhancing the advantageous effects of the present invention.

The host compound used in the present invention is also preferably a compound represented by General formula (I) because the compound represented by General formula (I) has a condensed ring structure (i.e., extending π-electron clouds), high carrier transportability, and high glass transition temperature (Tg). Although a condensed aromatic ring generally has a low excited triplet energy level ($T_1$), a compound represented by General formula (I) has a high $T_1$ and is suitable for use in the luminous material having a short emission wavelength (i.e., high $T_1$ and $S_1$).

[Chem 31]

General formula (I)

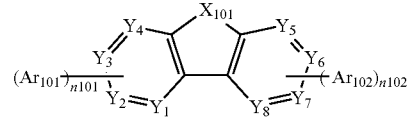

In General formula (I) described above, $X_{101}$ represents $NR_{101}$, an oxygen atom, a sulfur atom, $CR_{102}R_{103}$, or $SiR_{102}R_{103}$, and $y_1$ to $y_8$ each represent $CR_{104}$ or a nitrogen atom.

$R_{101}$ to $R_{104}$ each represent a hydrogen atom or a substituent and may be bonded together to form a ring.

$Ar_{101}$ and $Ar_{102}$ each represent an aromatic ring and may be identical to or different from each other.

In General formula (I), n101 and n102 each represent an integer of 0 to 4. If $R_{101}$ is a hydrogen atom, n101 is 1 to 4.

In General formula (I), $R_{101}$ to $R_{104}$ each represent a hydrogen atom or a substituent. The host compound used in the present invention may have any substituent that does not impede the function of the host compound. For example, the present invention encompasses a compound into which such a substituent is introduced through a synthetic scheme and which exhibits the advantageous effects of the present invention.

Examples of the substituent represented by $R_{101}$ to $R_{104}$ include linear or branched alkyl groups (e.g., methyl, ethyl, propyl, isopropyl, t-butyl, pentyl, hexyl, octyl, dodecyl, tridecyl, tetradecyl, and pentadecyl); alkenyl groups (e.g., vinyl and allyl); alkynyl groups (e.g., ethynyl and propargyl); aromatic hydrocarbon groups (also referred to as aromatic carbocyclic groups or aryl groups, such as groups derived from rings of benzene, biphenyl, naphthalene, azulene, anthracene, phenanthrene, pyrene, chrysene, naphthacene, triphenylene, o-terphenyl, m-terphenyl, p-terphenyl, acenaphthene, coronene, indene, fluorene, fluoranthrene, naphthacene, pentacene, perylene, pentaphene, picene, pyrene, pyranthrene, anthranthrene, and tetralin); aromatic heterocyclic groups (e.g., groups derived from rings of furan, dibenzofuran, thiophene, dibenzothiophene, oxazole, pyrrole, pyridine, pyridazine, pyrimidine, pyrazine, triazine, benzimidazole, oxadiazole, triazole, imidazole, pyrazole, thiazole, indole, indazole, benzimidazole, benzothiazole, benzoxazole, quinoxaline, quinazoline, cinnoline, quinoline, isoquinoline, phthalazine, naphthyridine, carbazole, carboline, and diazacarbazole (one of the carbon atoms forming the carboline ring is replaced with a nitrogen atom in the ring; a carboline ring and a diazacarbazole ring may be collectively referred to as "azacarbazole ring"); non-aromatic hydrocarbon ring groups (e.g., cyclopentyl and cyclohexyl); non-aromatic heterocyclic groups (e.g., pyrrolidyl, imidazolidyl, morpholyl, and oxazolidyl); alkoxy groups (e.g., methoxy, ethoxy, propyloxy, pentyloxy, hexyloxy, octyloxy, and dodecyloxy); cycloalkoxy groups (e.g., cyclopentyloxy and cyclohexyloxy); aryloxy groups (e.g., phenoxy and naphthyloxy); alkylthio groups (e.g., methylthio, ethylthio, propylthio, pentylthio, hexylthio, octylthio, and dodecylthio); cycloalkylthio groups (e.g., cyclopentylthio and cyclohexylthio); arylthio groups (e.g., phenylthio and naphthylthio); alkoxycarbonyl groups (e.g., methyloxycarbonyl, ethyloxycarbonyl, butyloxycarbonyl, octyloxycarbonyl, and dodecyloxycarbonyl); aryloxycarbonyl groups (e.g., phenyloxycarbonyl and naphthyloxycarbonyl); sulfamoyl groups (e.g., aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, and 2-pyridylaminosulfonyl); acyl groups (e.g., acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl); acyloxy groups (e.g., acetyloxy, ethylcarbonyloxy, butylcarbonyloxy, octylcarbonyloxy, dodecylcarbonyloxy, and phenylcarbonyloxy); amido groups (e.g., methylcarbonylamino, ethylcarbonylamino, dimethylcarbonylamino, propylcarbonylamino, pentylcarbonylamino, cyclohexylcarbonylamino, 2-ethyhexylcarbonylamino, octylcarbonylamino, dodecylcarbonylamino, phenylcarbonylamino, and naphthylcarbonylamino); carbamoyl groups (e.g., aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, and 2-pyridylaminocarbonyl); ureido groups (e.g., methylureido, ethylureido, pentylureido, cyclohexylureido, octylureido, dodecylureido, phenylureido, naphthylureido, and 2-pyridylaminoureido); sulfinyl groups (e.g., methylsulfinyl, ethylsulfinyl, butylsulfinyl, cyclohexylsulfinyl, 2-ethylhexylsulfinyl, dodecylsulfinyl, phenylsulfinyl, naphthylsulfinyl, and 2-pyridylsulfinyl); alkylsulfonyl groups (e.g., methylsulfonyl, ethylsulfonyl, butylsulfonyl, cyclohexylsulfonyl, 2-ethylhexylsulfonyl, and dodecylsulfonyl); arylsulfonyl and heteroarylsulfonyl groups (e.g., phenylsulfonyl, naphthylsulfonyl, and 2-pyridylsulfonyl); amino groups (e.g., amino, ethylamino, dimethylamino, butylamino, cyclopentylamino, 2-ethylhexylamino, dodecylamino, anilino, naphthylamino, and 2-pyridylamino); halogen atoms (e.g., fluorine, chlorine, and bromine); fluorohydrocarbon groups (e.g., fluoromethyl, trifluoromethyl, pentafluoromethyl, and pentafluorophenyl); cyano groups; nitro groups; hydroxy groups; thiol groups; silyl groups (e.g., trimethylsilyl, triisopropylsilyl, triphenylsilyl, and phenyldiethylsilyl); and atomic deuterium.

These substituents may further have any of the substituents described above. These substituents may be bonded together to form a ring.

In General formula (I), preferably, at least three of $y_1$ to $y_4$ or at least three of $y_5$ to $y_8$ are $CR_{102}$, and more preferably, all of $y_1$ to $y_8$ are $CR_{102}$. Such a structure exhibits high hole transportability or high electron transportability. Thus, holes and electrons injected from the anode and the cathode are efficiently recombined in the luminous layer, to emit light.

Particularly preferred is a compound represented by General formula (I) wherein $X_{101}$ is $NR_{101}$, an oxygen atom, or a sulfur atom, the compound having a low energy level of LUMO and exhibiting high electron transportability. The condensed ring formed by $X_{101}$ and $y_1$ to $y_8$ is more preferably a carbazole, azacarbazole, dibenzofuran, or azadibenzofuran ring.

The host compound preferably has rigidity. Thus, if $X_{101}$ is $NR_{101}$, $R_{101}$ is preferably an aromatic hydrocarbon group or an aromatic heterocyclic group, which has a π-conjugated structure. $R_{101}$ may further have a substituent represented by $R_{101}$ to $R_{103}$.

In General formula (I), the aromatic ring represented by $Ar_{101}$ or $Ar_{102}$ is an aromatic hydrocarbon or heterocyclic ring. The aromatic ring may be a single ring or a condensed ring. The aromatic ring may be unsubstituted or may have a substituent similar to that represented by $R_{101}$ to $R_{104}$ described above.

In General formula (I), the aromatic hydrocarbon ring represented by $Ar_{101}$ or $Ar_{102}$ may be similar to that exemplified above as a substituent represented by $R_{101}$ to $R_{104}$ described above.

In the partial structure represented by General formula (I), the aromatic heterocyclic ring represented by $Ar_{101}$ or $Ar_{102}$ may be similar to that exemplified above as a substituent represented by $R_{101}$ to $R_{104}$.

In view of the fact that the host compound represented by General formula (I) should have a high $T_1$, the aromatic ring represented by $Ar_{101}$ or $Ar_{102}$ preferably has a high $T_1$. Examples of preferred aromatic rings include rings of benzene (including polyphenylene structures composed of a plurality of linked benzene rings (e.g., biphenyl, terphenyl, and quarterphenyl)), fluorene, triphenylene, carbazole, azacarbazole, dibenzofuran, azadibenzofuran, dibenzothiophene, dibenzothiophene, pyridine, pyrazine, indoloindole, indole, benzofuran, benzothiophene, imidazole, and triazine. More preferred are rings of benzene, carbazole, azacarbazole, and dibenzofuran.

If $Ar_{101}$ or $Ar_{102}$ is a carbazole ring or an azacarbazole ring, the ring is more preferably bonded at position N (also referred to as "position 9") or position 3.

If $Ar_{101}$ or $Ar_{102}$ is a dibenzofuran ring, the ring is more preferably bonded at position 2 or 4.

In view of the use of the organic EL element in a vehicle, the host compound preferably has a high Tg under the assumption that the temperature in the vehicle increases to a high level. In a preferred embodiment, the aromatic ring represented by $Ar_{101}$ or $Ar_{102}$ is a condensed ring composed of three or more rings for increasing the Tg of the host compound represented by General formula (I).

Examples of the aromatic hydrocarbon condensed ring composed of three or more rings include rings of naphthacene, anthracene, tetracene, pentacene, hexacene, phenanthrene, pyrene, benzopyrene, benzazulene, chrysene, benzochrysene, acenaphthene, acenaphthylene, triphenylene, coronene, benzocoronene, hexabenzocoronene, fluorene, benzofluorene, fluoranthene, perylene, naphthoperylene, pentabenzoperylene, benzoperylene, pentaphene, picene, pyranthrene, coronene, naphthocoronene, ovalene, and anthranthrene. Each of these rings may further have any of the substituents described above.

Examples of the aromatic heterocyclic ring composed of three or more rings include rings of acridine, benzoquinoline, carbazole, carboline, phenazine, phenanthridine, phenanthroline, carboline, cyclazine, quindoline, tepenidine, quinindoline, triphenodithiazine, triphenodioxazine, phenanthrazine, anthrazine, perimidine, diazacarbazole (any one of the carbon atoms forming the carboline ring is replaced with a nitrogen atom in the ring), phenanthroline, dibenzofuran, dibenzothiophene, naphthofuran, naphthothiophene, benzodifuran, benzodithiophene, naphthodifuran, naphthodithiophene, anthrafuran, anthradifuran, anthrathiophene, anthradithiophene, thianthrene, phenoxathiine, and thiophanthrene (naphthothiophene). Each of these rings may further have a substituent.

In General formula (I), each of n101 and n102 is preferably an integer of 0 to 2, and n101+n102 is more preferably an integer of 1 to 3. If $R_{101}$ is a hydrogen atom and both n101 and n102 are zero, the host compound represented by General formula (I) has a low molecular weight and a low Tg. Thus, if $R_{101}$ is a hydrogen atom, n101 is an integer of 1 to 4.

The host compound having a structure represented by General formula (I) and used in the present invention is preferably a compound having a structure represented by General formula (II) because such a compound exhibits particularly high carrier transportability.

[Chem 32]

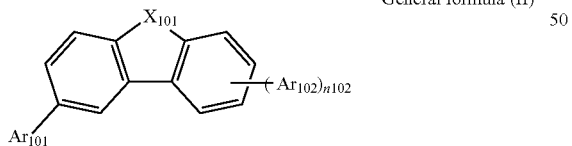

General formula (II)

In General formula (II), $X_{101}$, $Ar_{101}$, $Ar_{102}$, and n102 are the same as those defined above in General formula (I).

In General formula (II), n102 is preferably an integer of 0 to 2, more preferably 0 or 1.

In General formula (II), the condensed ring including $X_{101}$ may have any substituent that does not impede the function of the host compound used in the present invention, besides $Ar_{101}$ and $Ar_{102}$.

The compound represented by General formula (II) is preferably represented by General formula (III-1), (III-2), or (III-3).

[Chem 33]

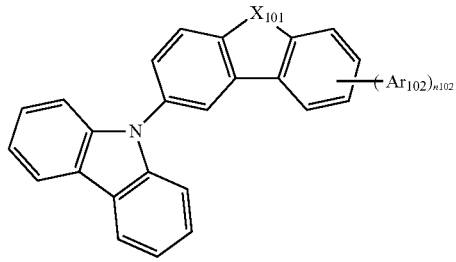

General formula (III-1)

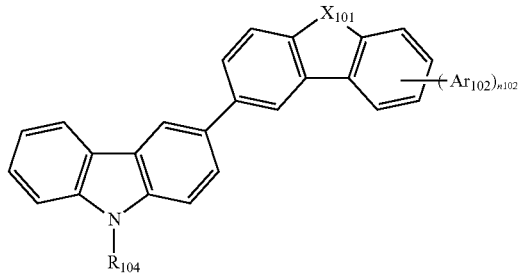

General formula (III-2)

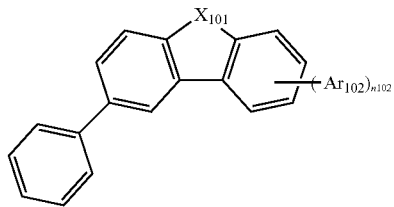

General formula (III-3)

In General formulae (III-1) to (III-3), $X_{101}$, $Ar_{102}$, and n102 are the same as $X_{101}$, $Ar_{102}$, and n102 defined above in Formula (II). In General formulae (III-2), $R_{104}$ is the same as $R_{104}$ defined above in General formula (I)

In General formulae (III-1) to (III-3), the condensed ring including $X_{101}$, the carbazole ring, or the benzene ring may further have any substituent that does not impede the function of the host compound used in the present invention.

Examples of the host compounds used in the present invention represented by General formulae (I), (II), and (III-1) to (III-3) and having other structures include, but are not limited to, the following compounds:

[Chem 34]
H-1
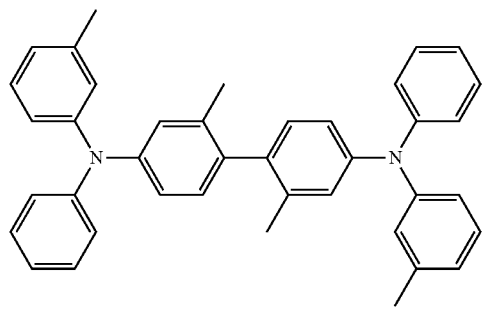
H-2
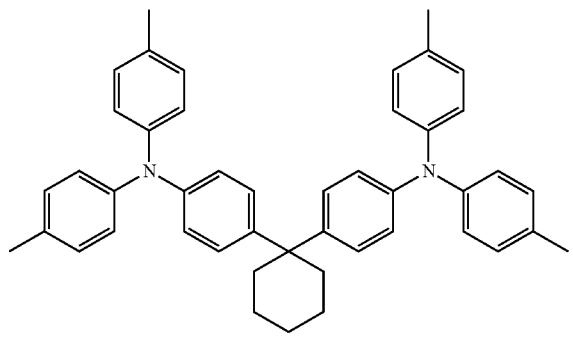
H-3
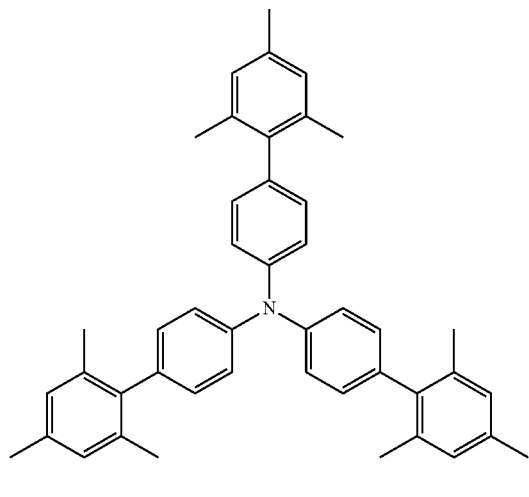
H-4
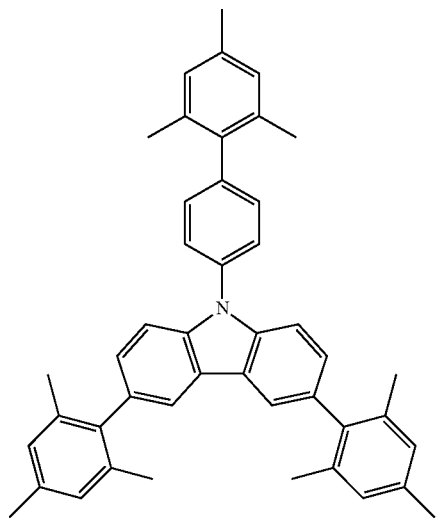
H-5
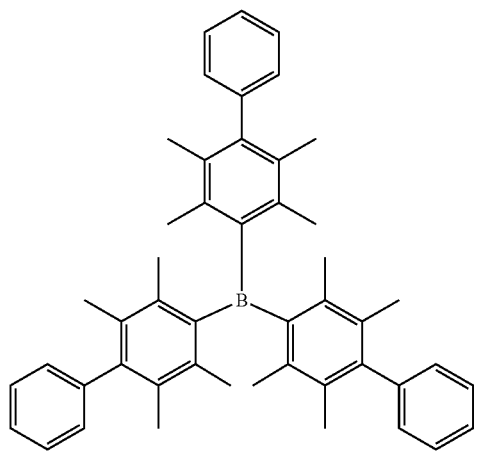
H-6
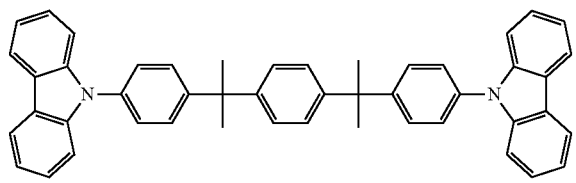

-continued
[Chem 35]
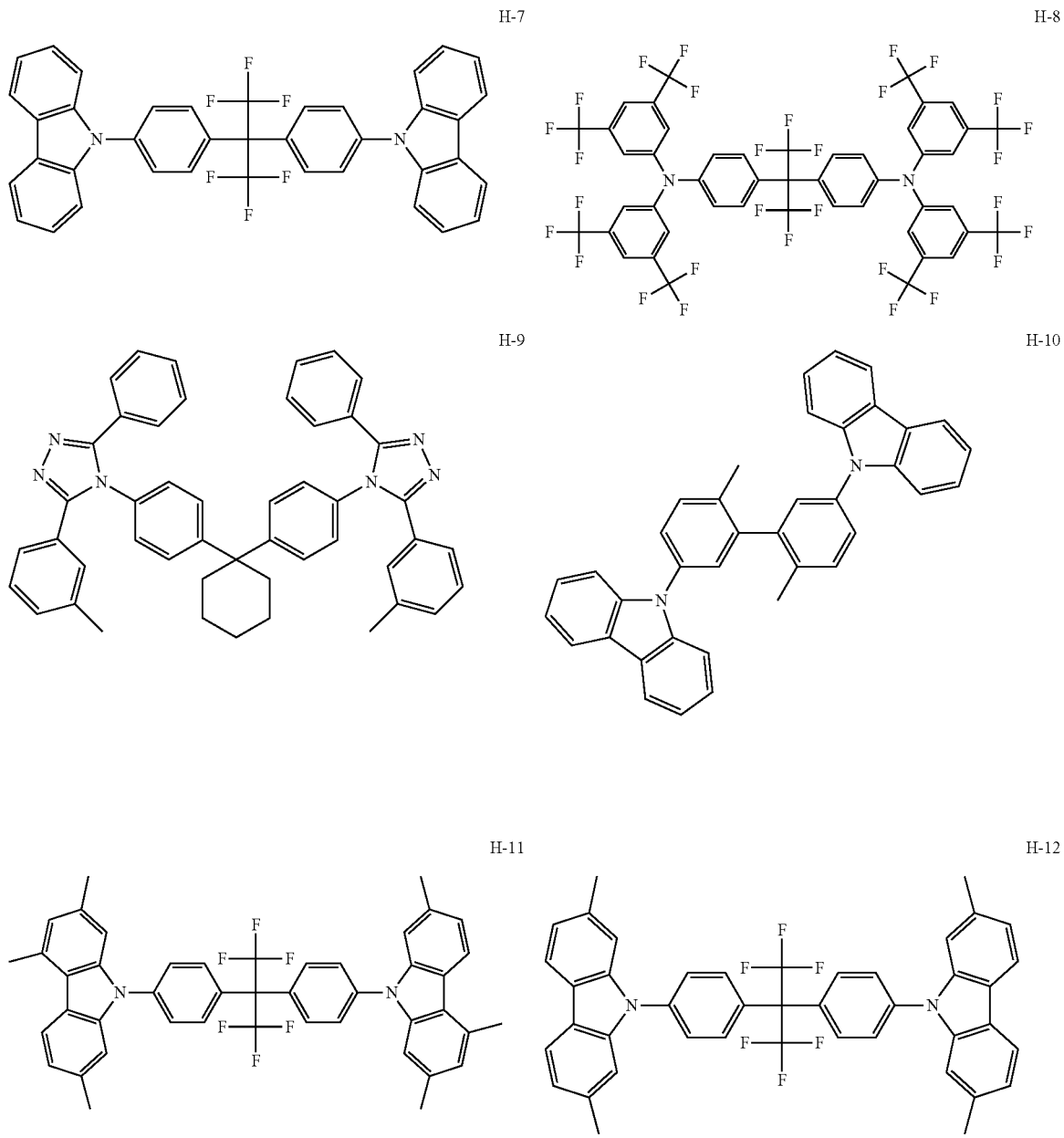
[Chem 36]
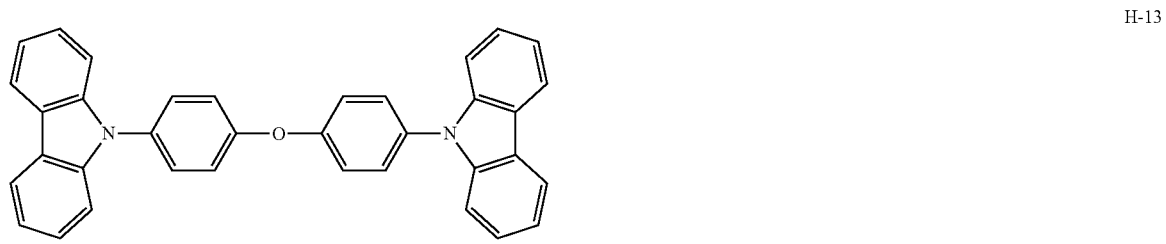

H-14
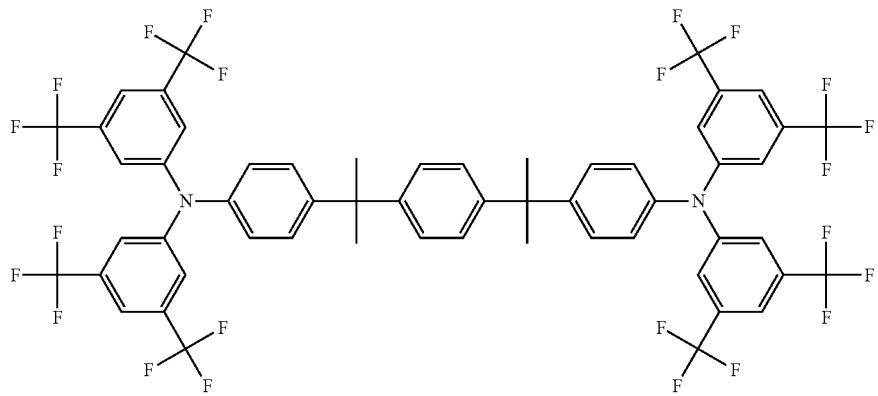
H-15
H-16
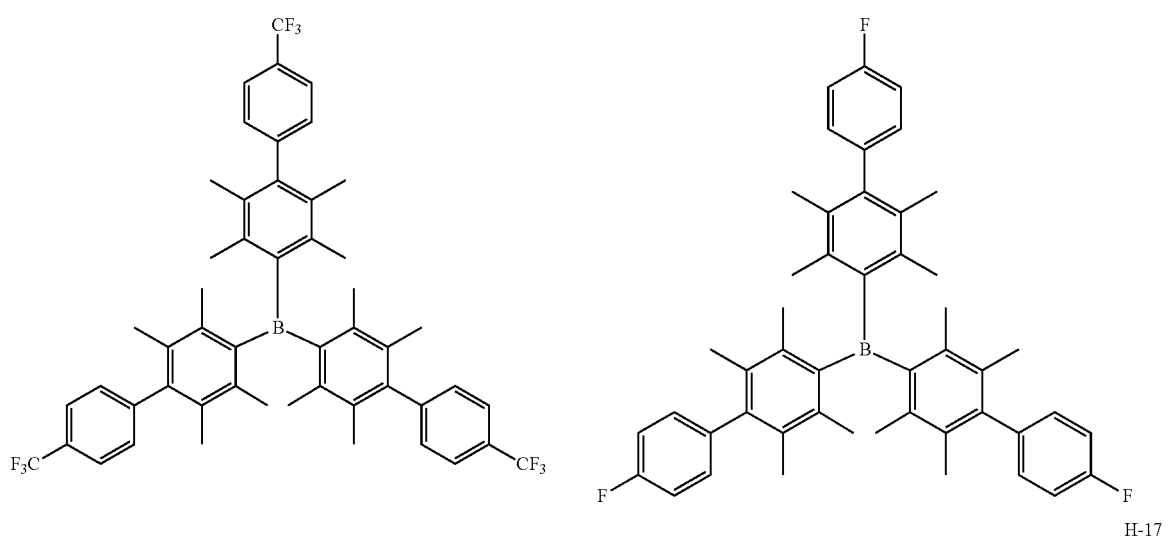
H-17
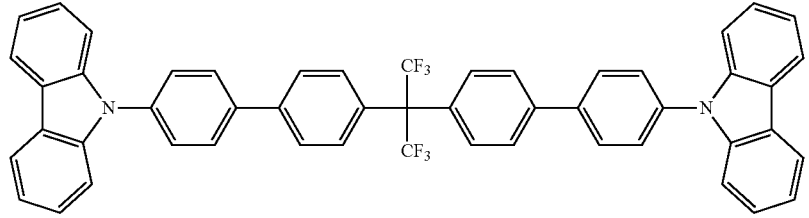
[Chem 37]
H-18
H-19
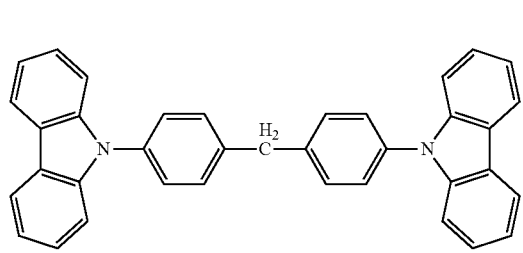
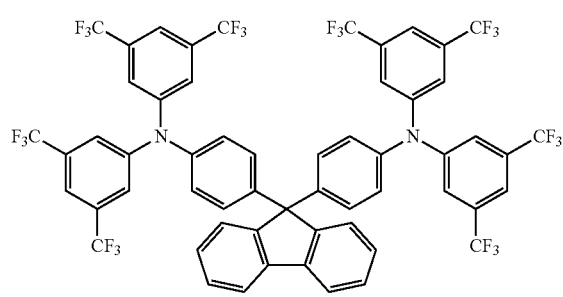

H-20
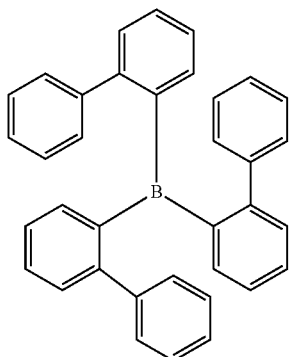
H-21
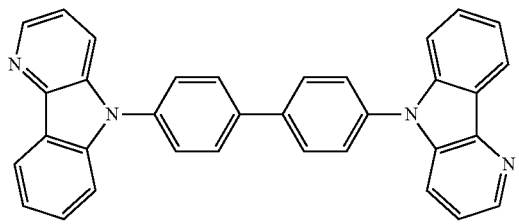
H-22
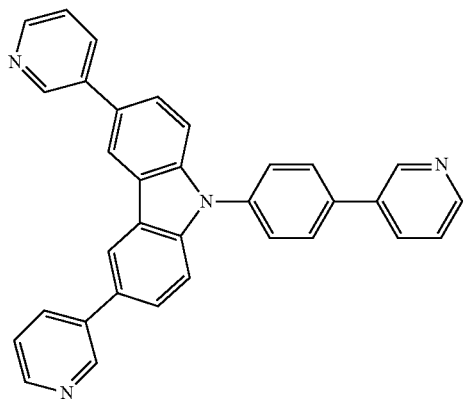
H-23
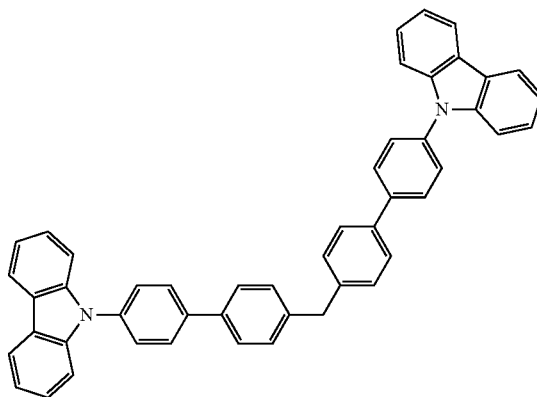
[Chem 38]
H-24
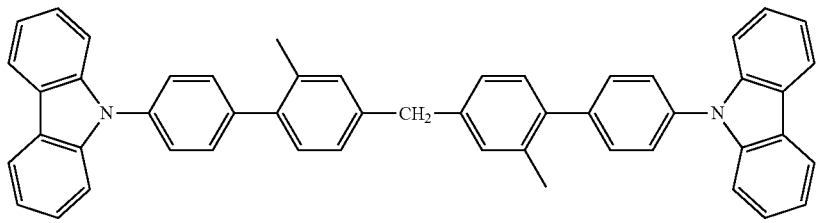
H-25
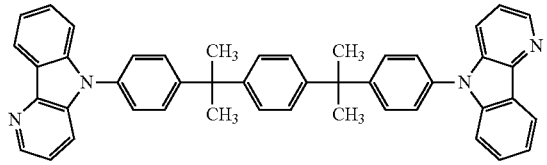
H-26
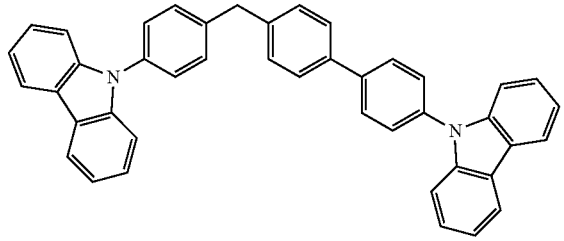
H-27
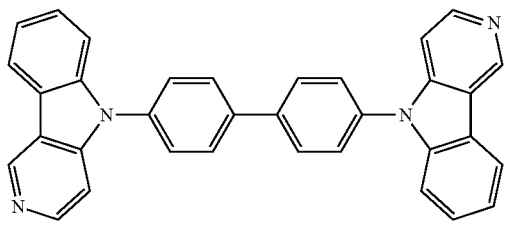
H-28
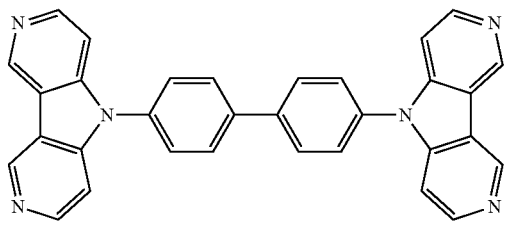

-continued
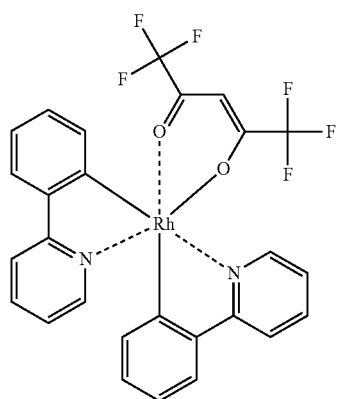
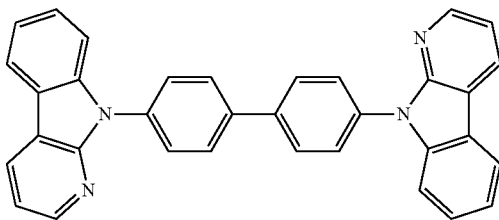
H-29
H-30
[Chem 39]
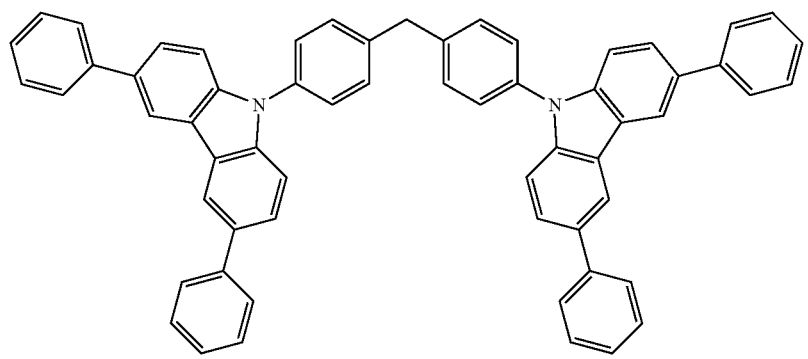
H-31
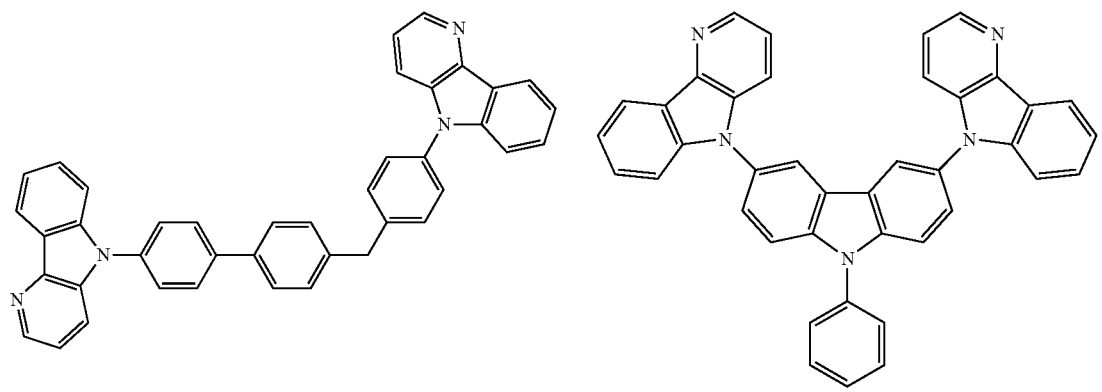
H-32
H-33

H-34
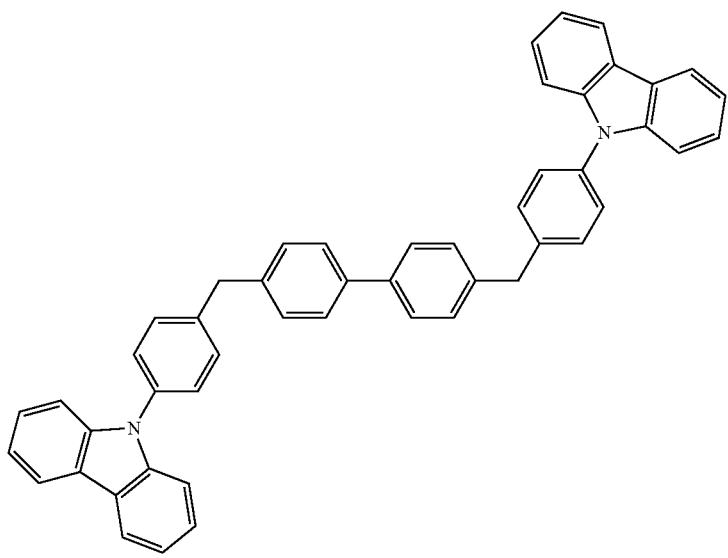
H-35
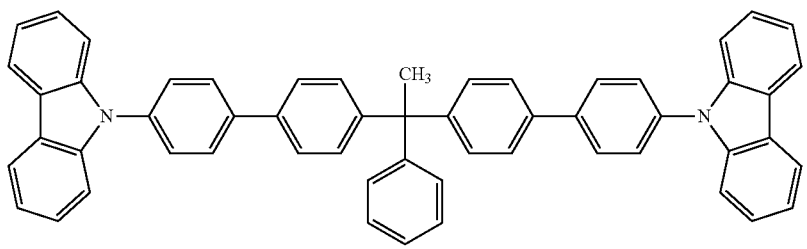
[Chem 40]
H-36
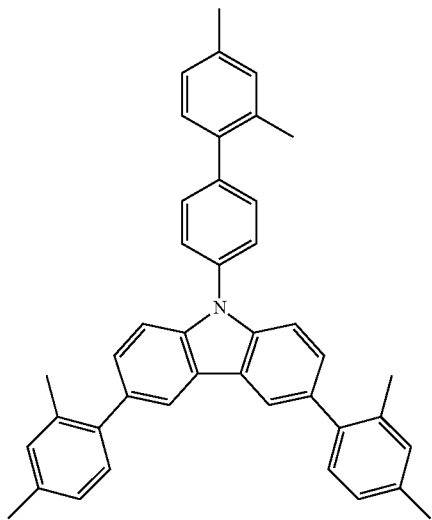
H-37
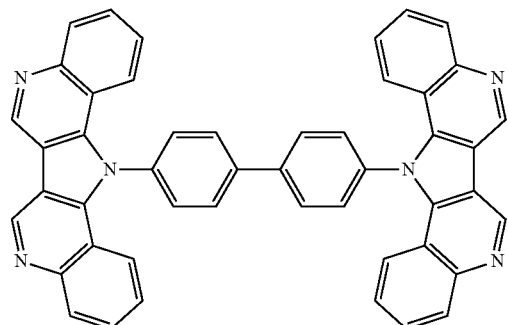
H-38
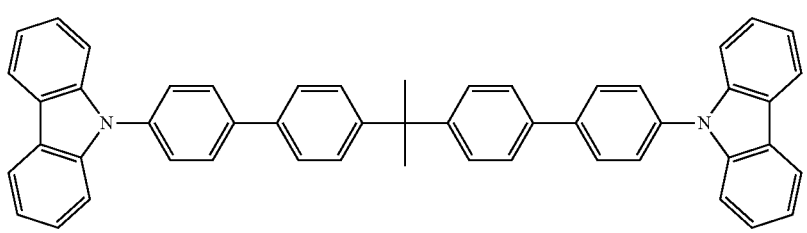

-continued
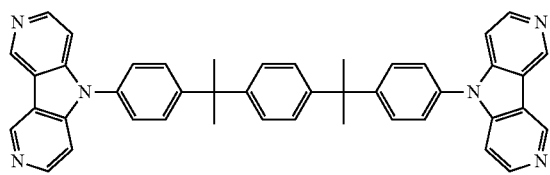
H-39
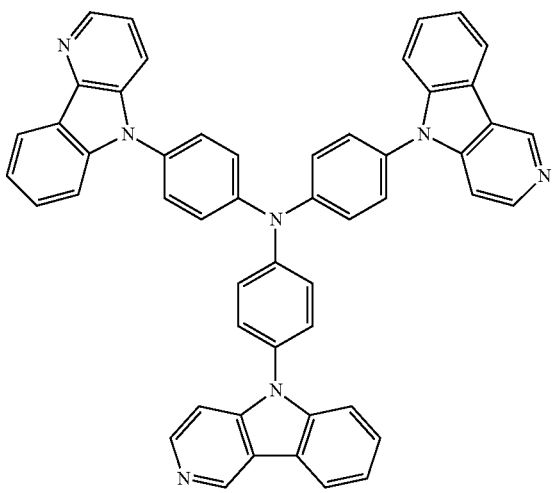
H-40
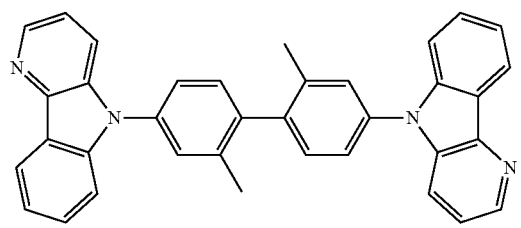
[Chem 41]
H-42
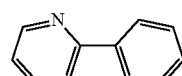
H-41
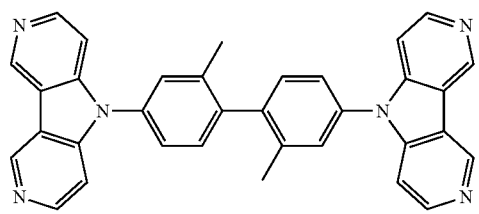
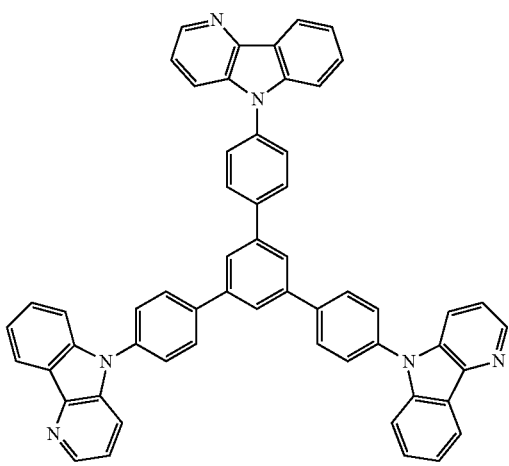
H-43
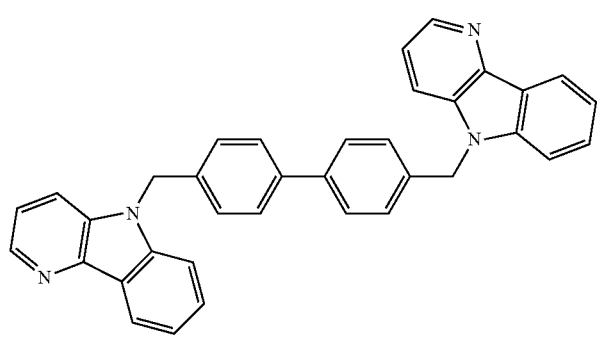
H-44

-continued
H-45
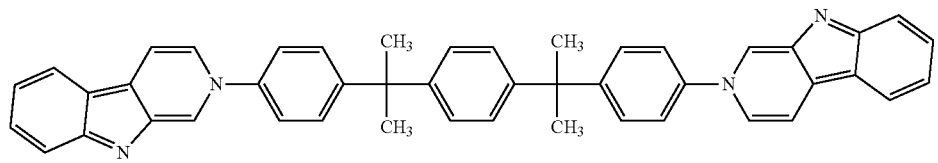
H-46
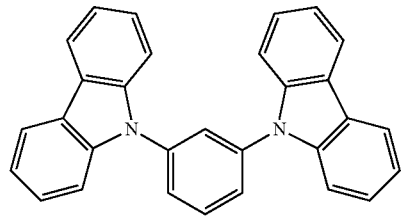
H-47
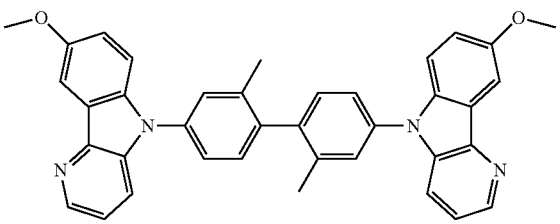
[Chem 42]
H-48
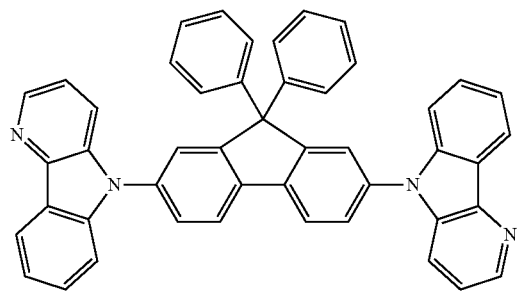
H-49
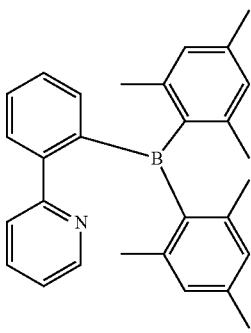
H-50
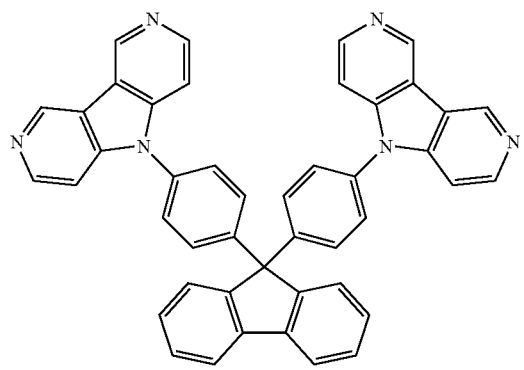
H-51
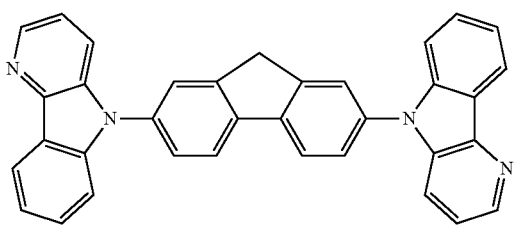
H-52
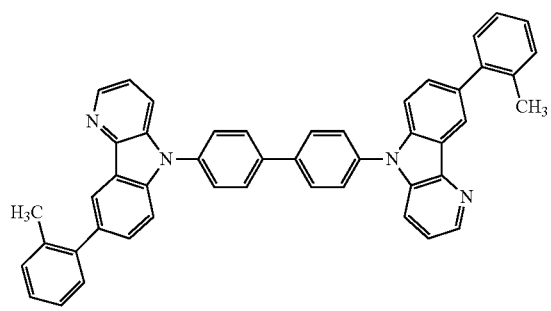
H-53
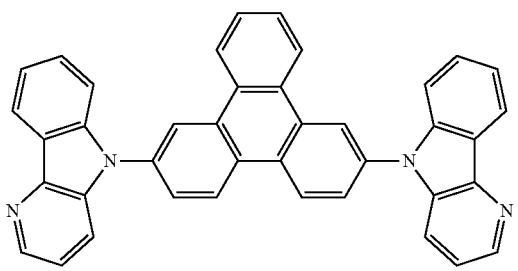

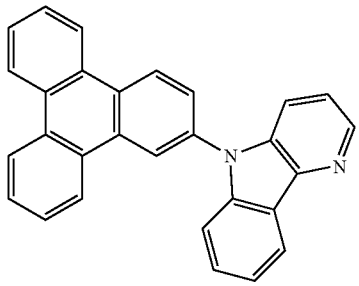
H-54
[Chem 43]
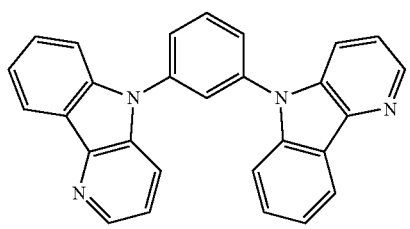
H-55
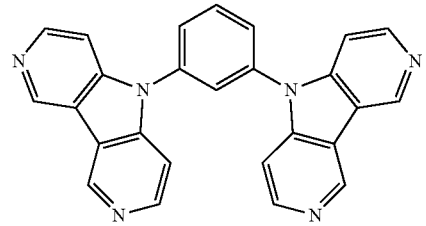
H-56
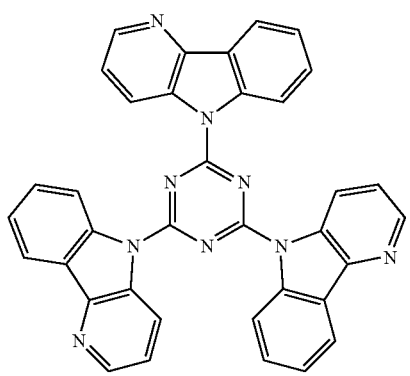
H-57
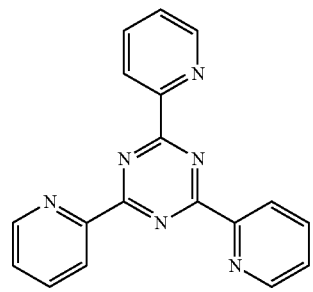
H-58
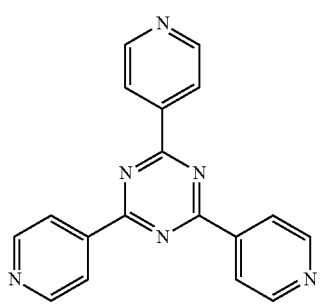
H-59
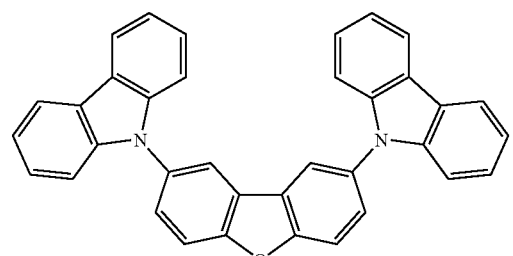
H-60

H-61
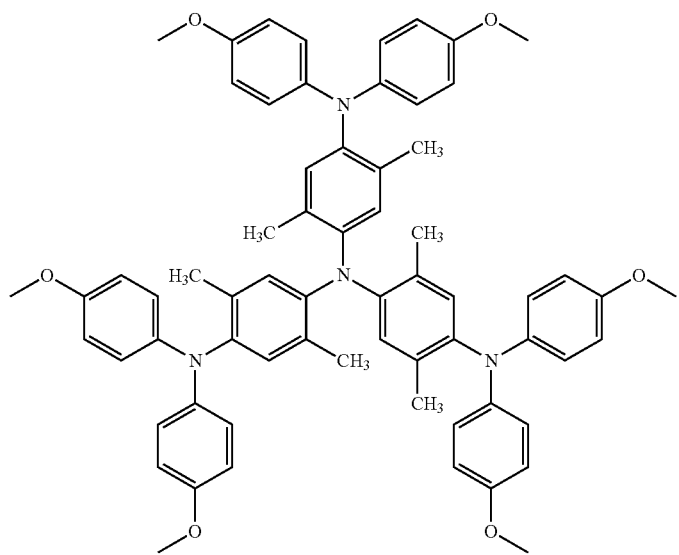
[Chem 44]
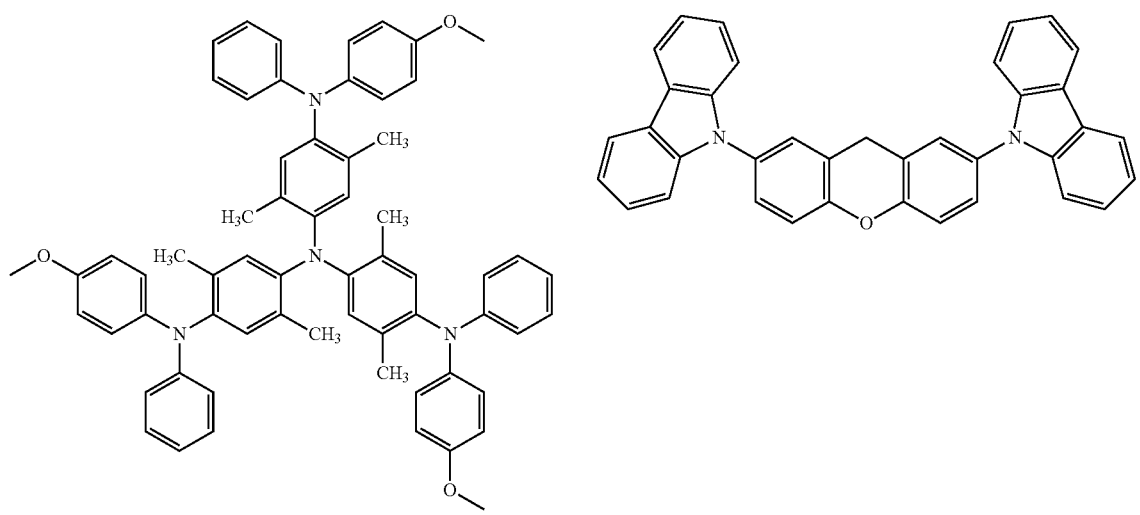
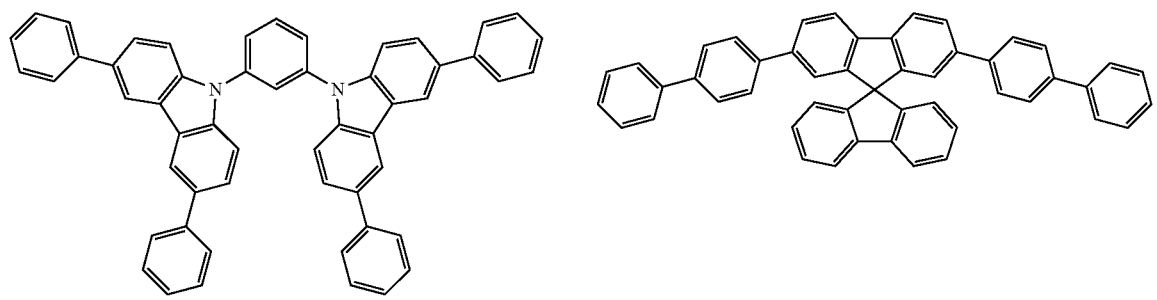

H-66
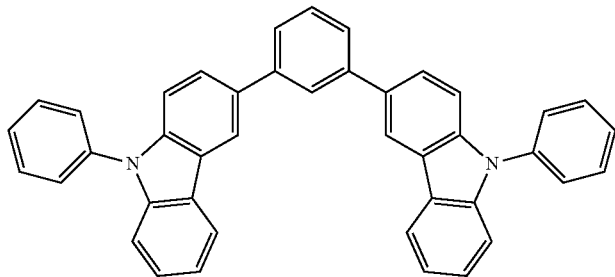
[Chem 45]
H-67
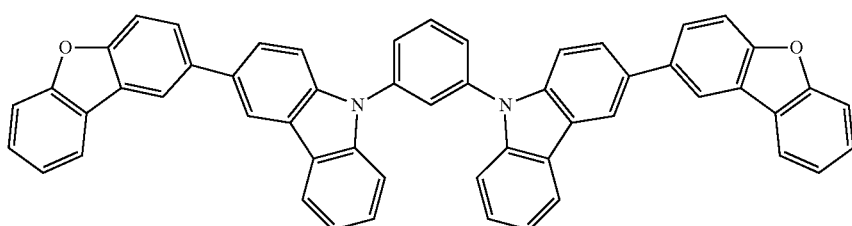
H-68
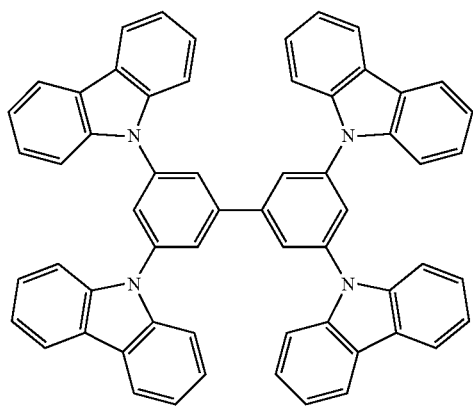
H-69
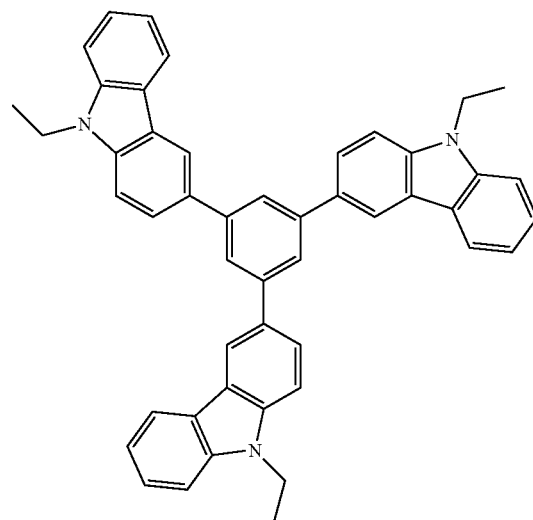
H-70
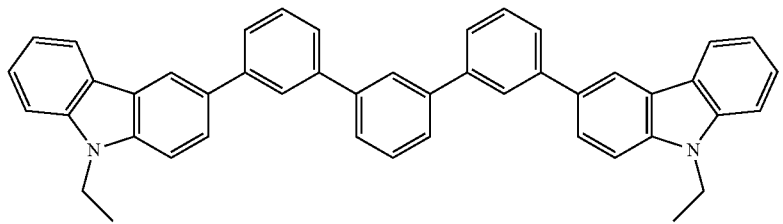
H-71
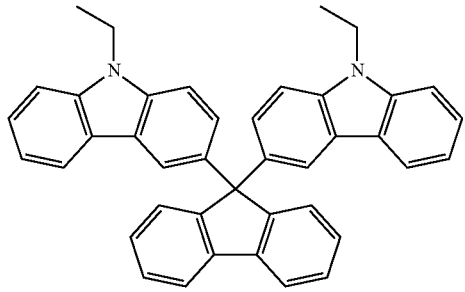
H-72
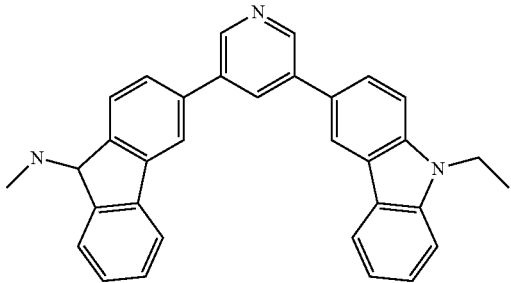

[Chem 46]
H-73
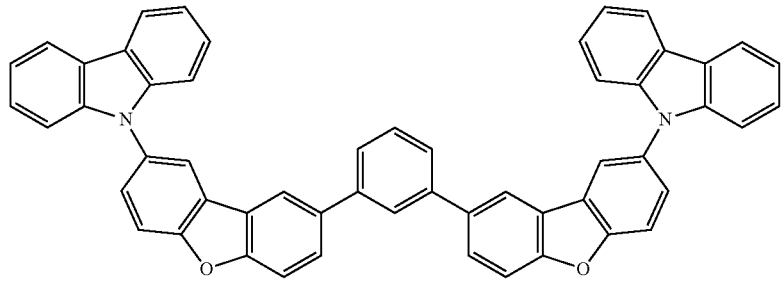
H-74
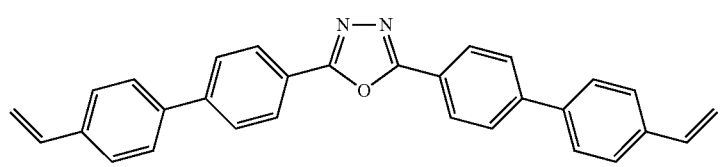
H-75
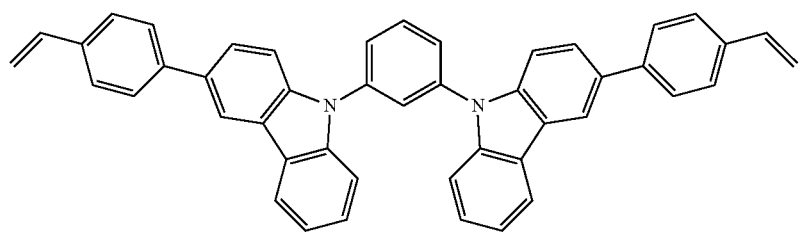
H-76
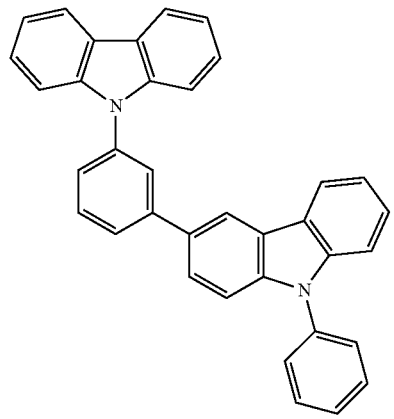
H-77
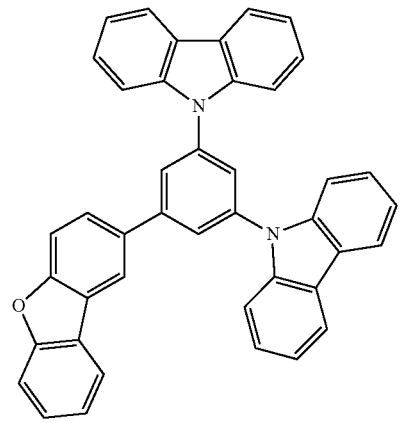
H-78
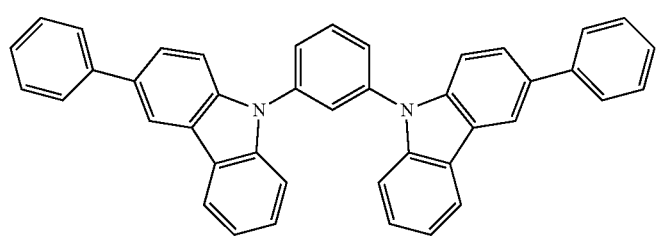

[Chem 47]
H-79
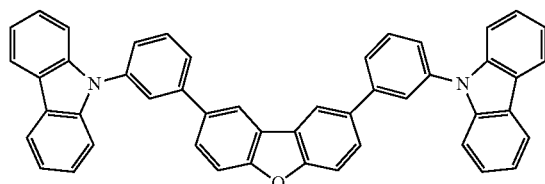
H-80
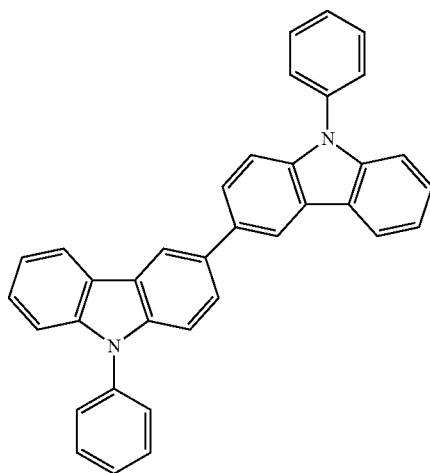
H-81
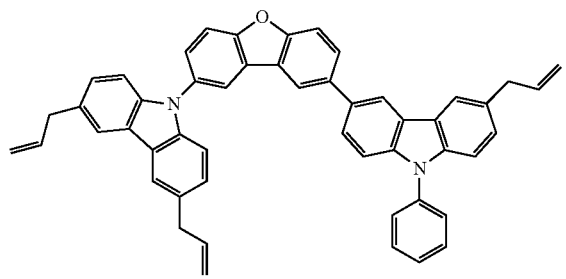
H-82
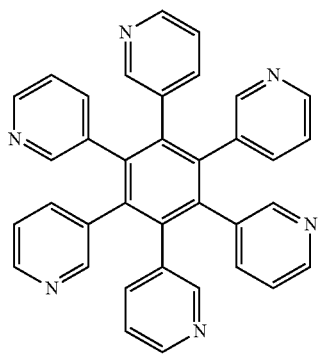
H-83
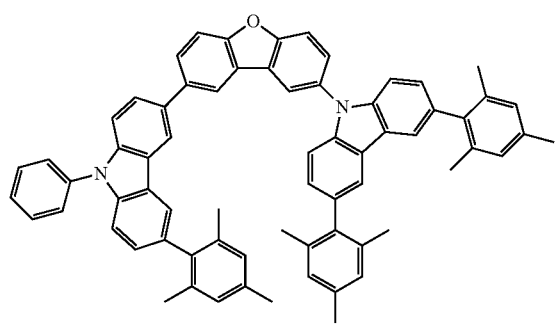
H-84
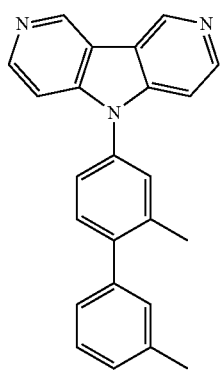

-continued
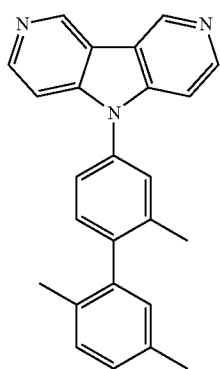
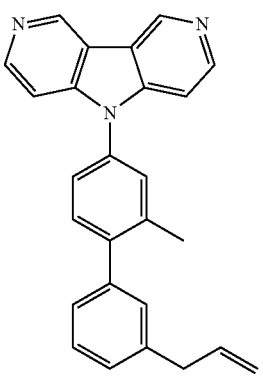
H-85
H-86
[Chem 48]
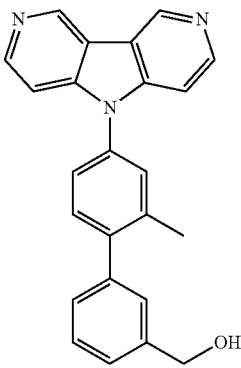
H-87
H-88
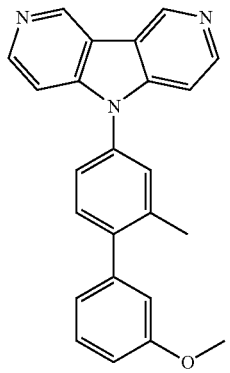
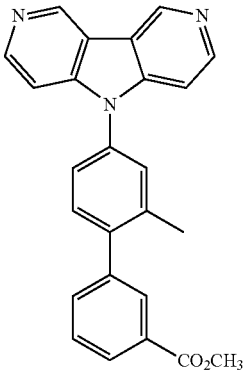
H-89
H-90
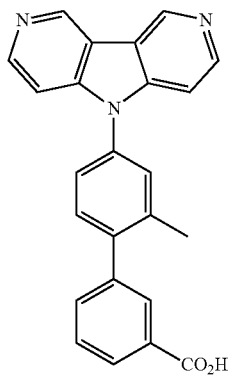
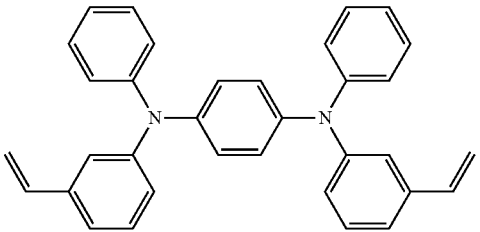
H-91
H-92

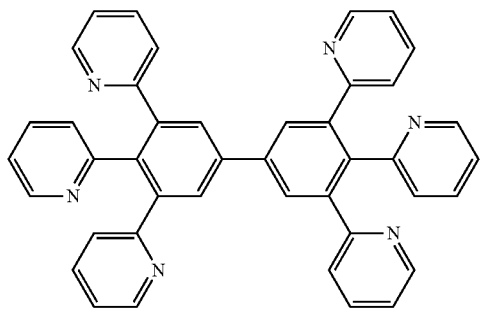
H-93
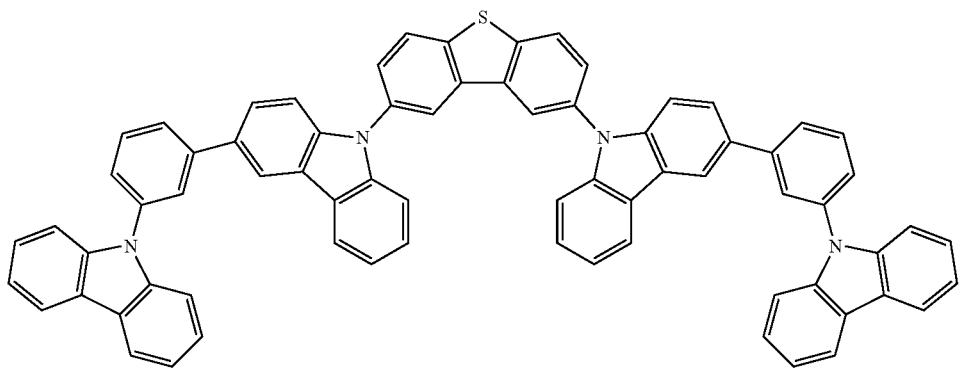
H-94
[Chem 49]
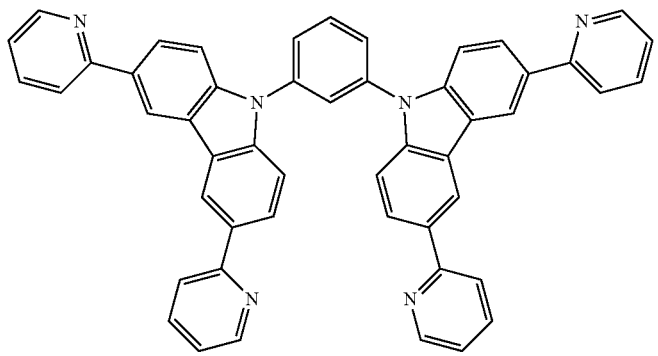
H-95
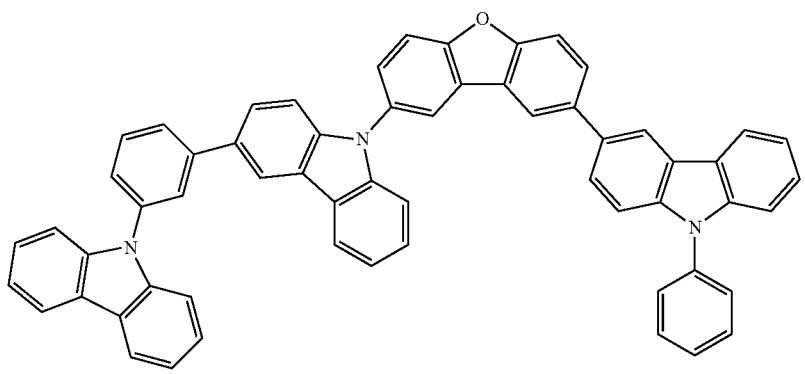
H-96

-continued
H-97
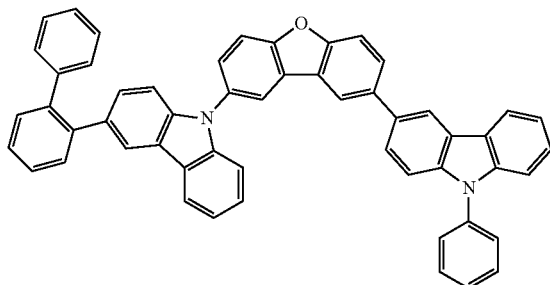
H-98
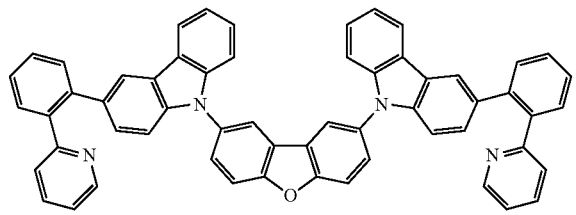
[Chem 50]
H-99
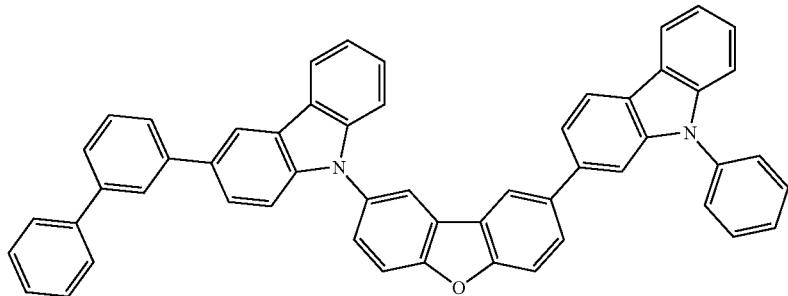
H-100
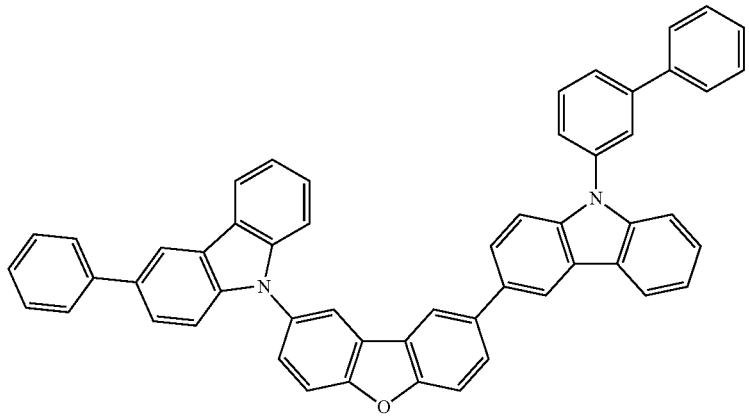
H-101
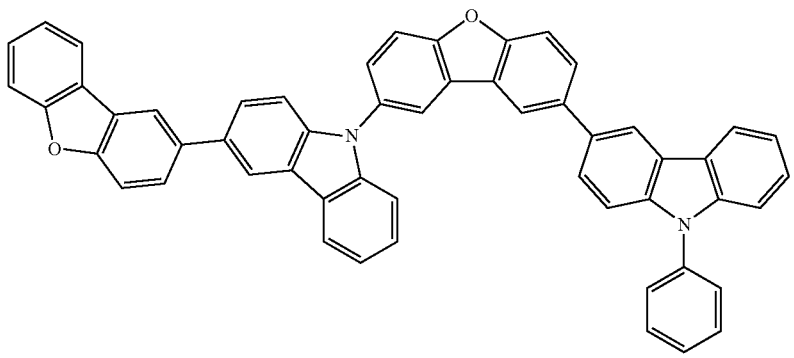

-continued
H-102
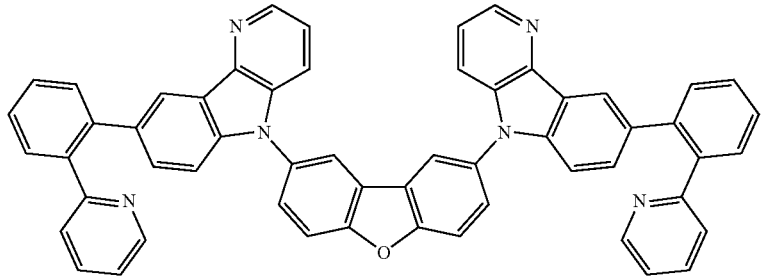
H-103
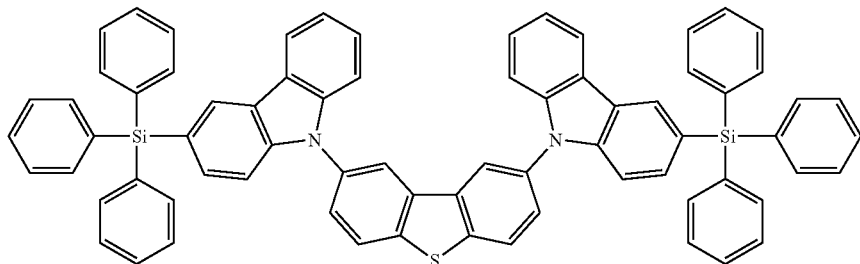
[Chem 51]
H-104
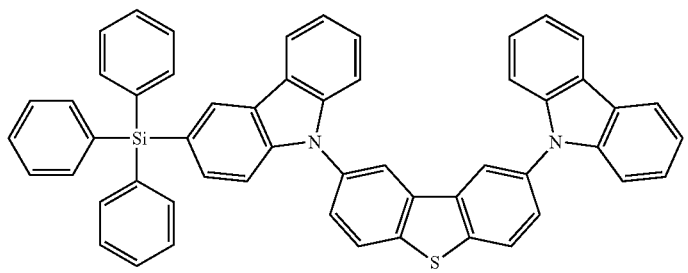
H-105
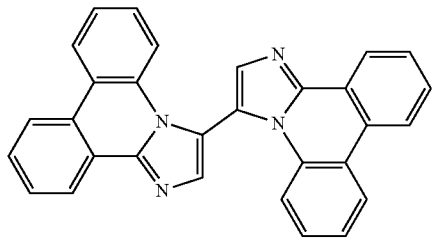
H-106
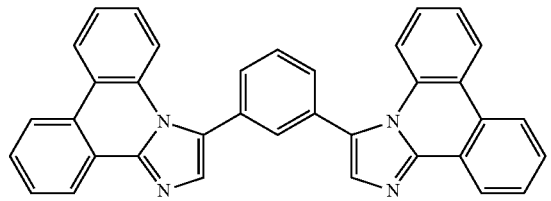
H-107
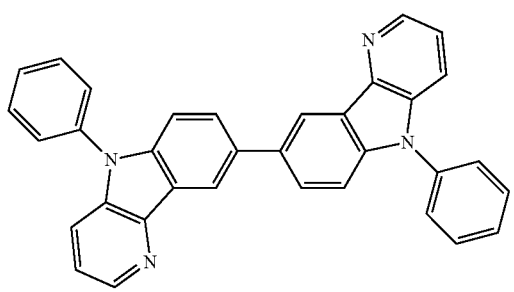
H-108
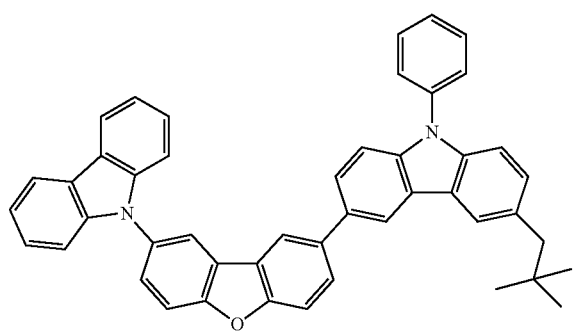

-continued
H-109
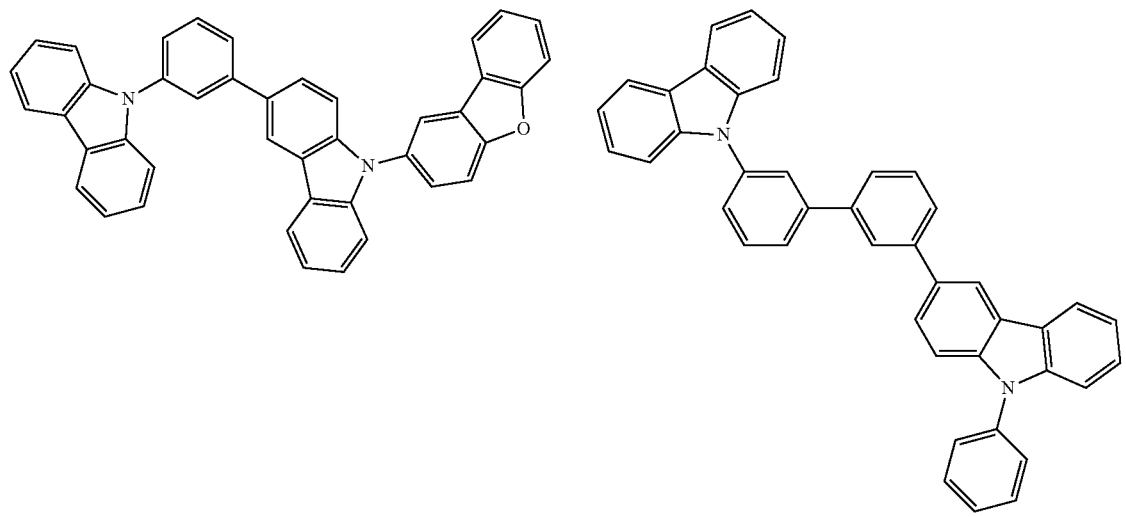
H-110
[Chem 52]
H-111
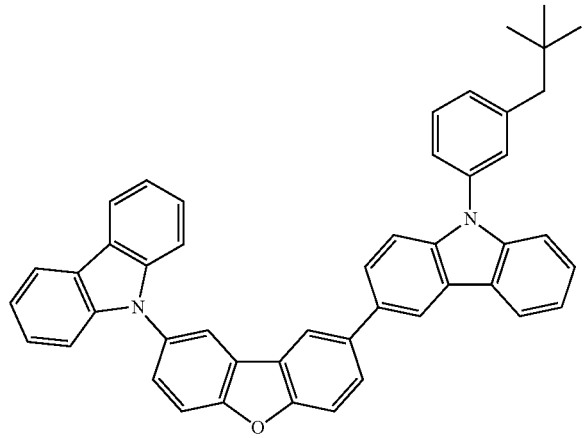
H-112
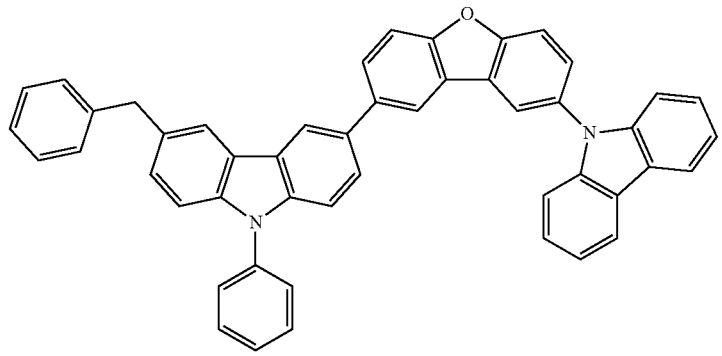
H-113
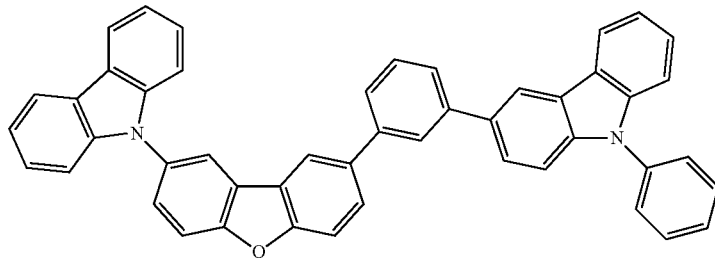

-continued
H-114
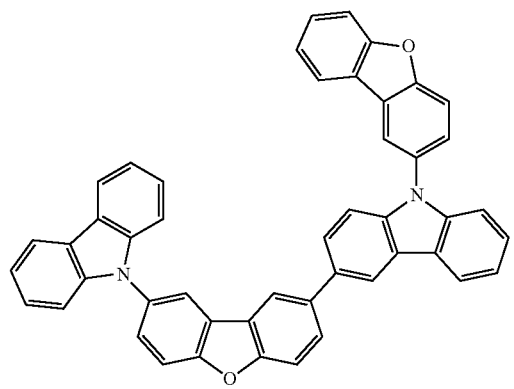
[Chem 53]
H-115
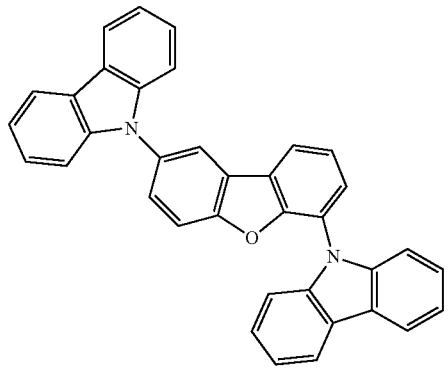
H-116
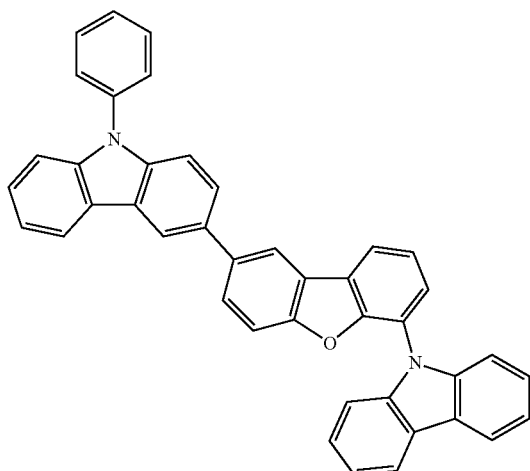
H-117
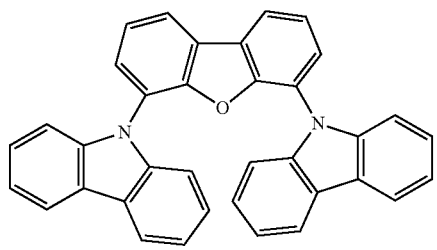
H-118
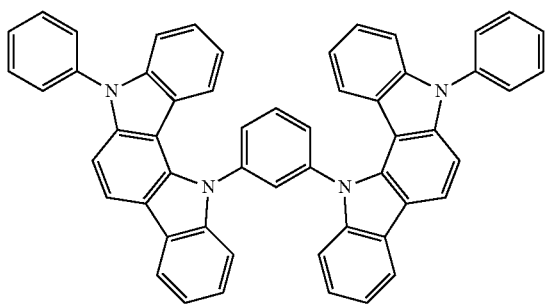
H-119
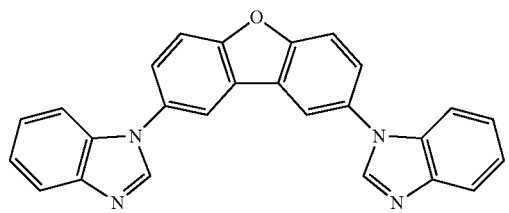
H-120
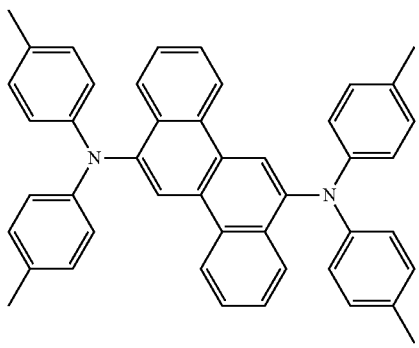
H-121
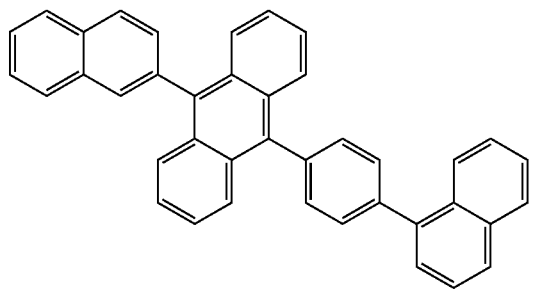

H-122
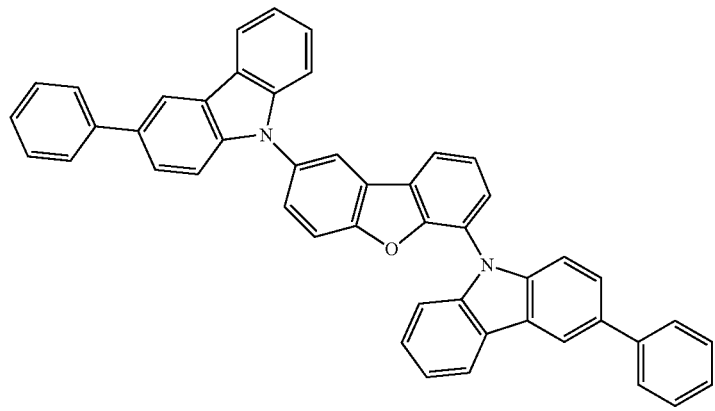
[Chem 54]
H-123
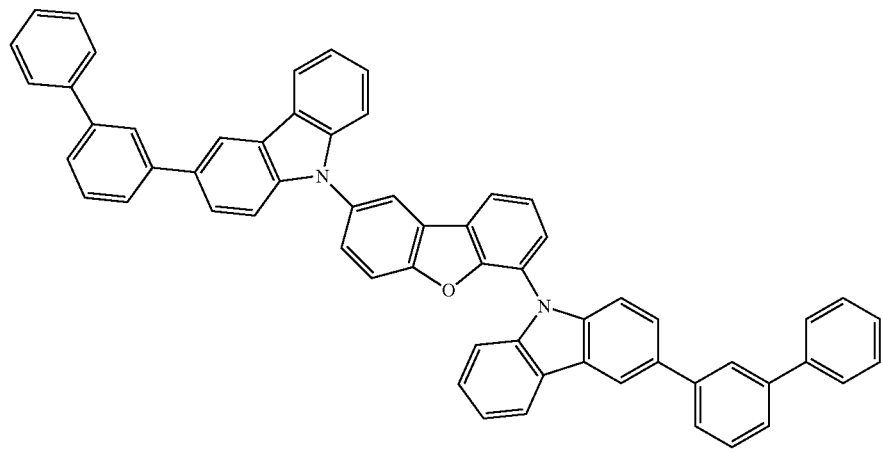
H-124
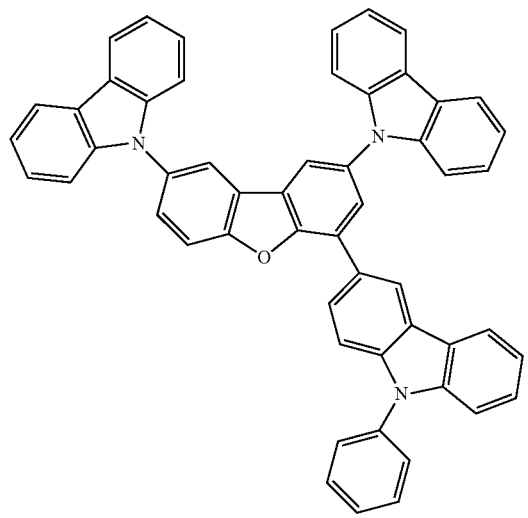
H-125
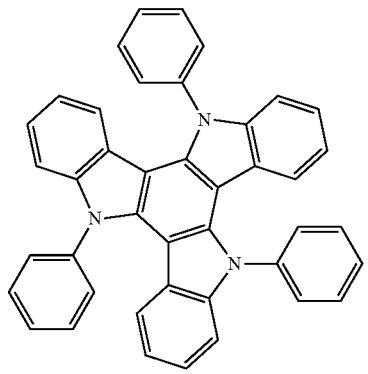

H-126
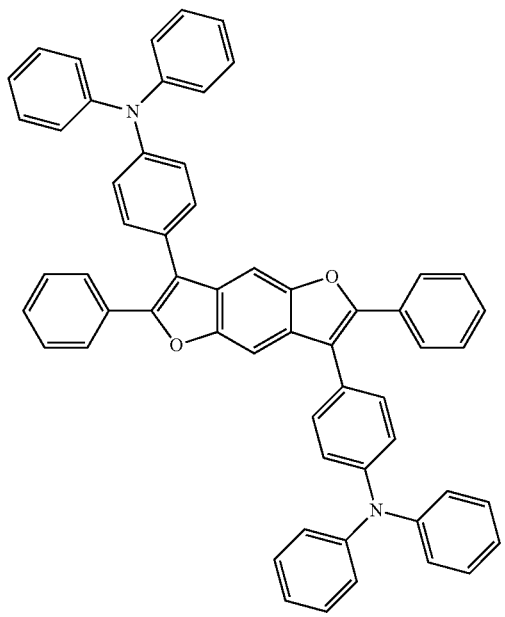
H-127
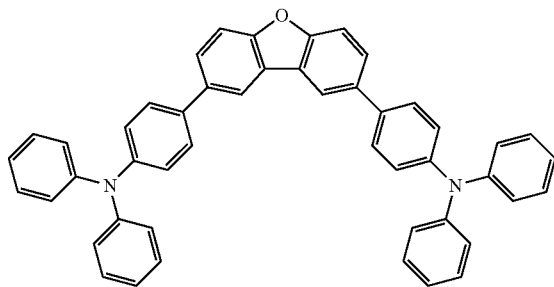
[Chem 55]
H-128
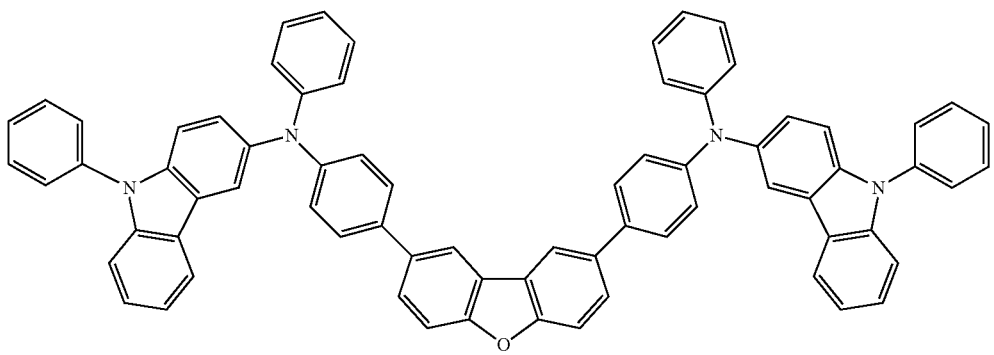
H-129
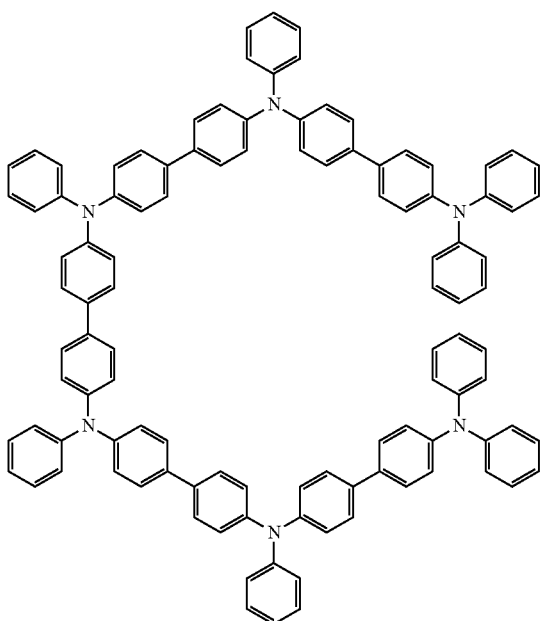
H-130
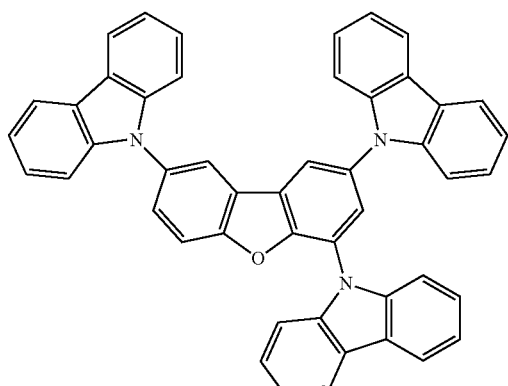

H-131
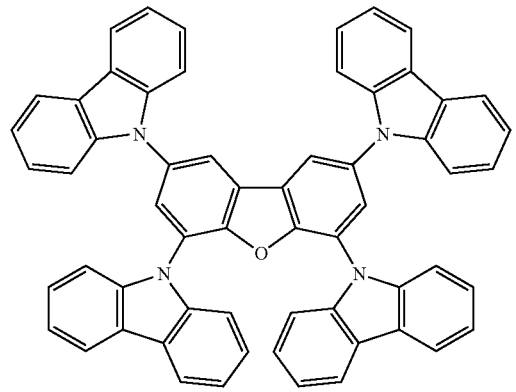
[Chem 56]
H-132
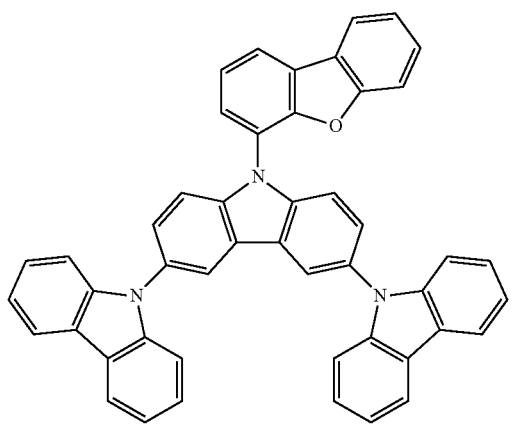
H-133
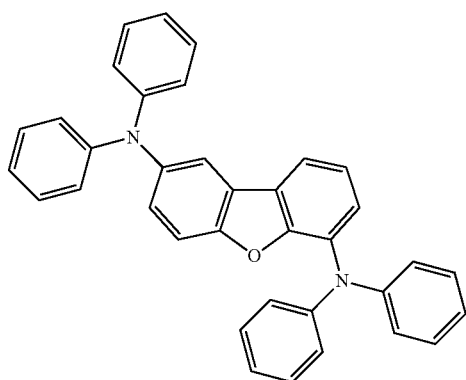
H-134
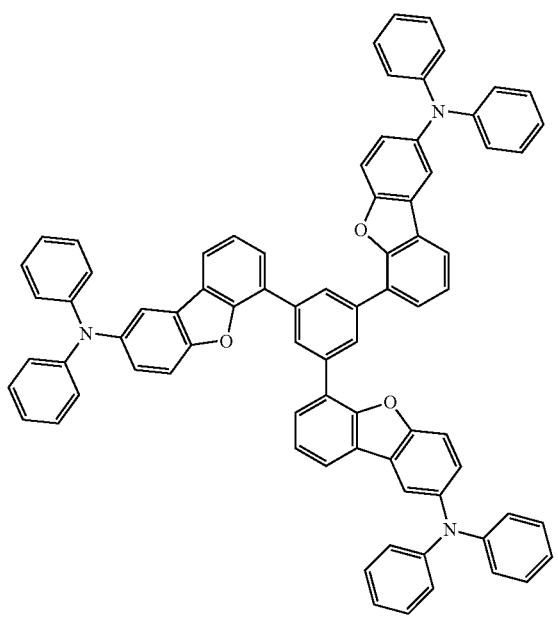
H-135
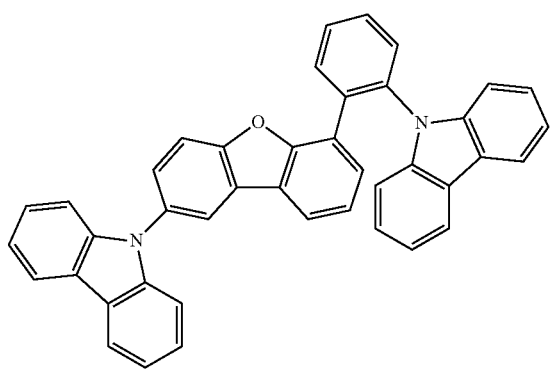

-continued
H-136
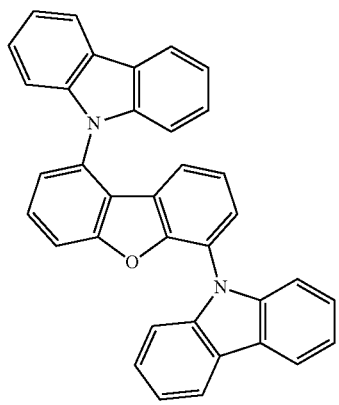
H-137
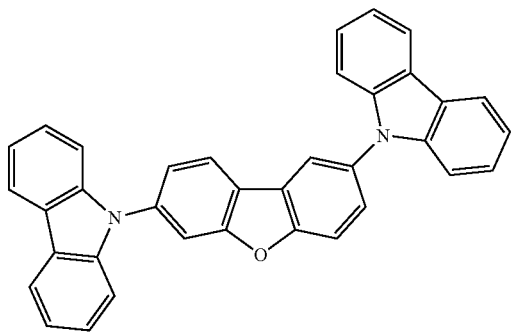
[Chem 57]
H-138
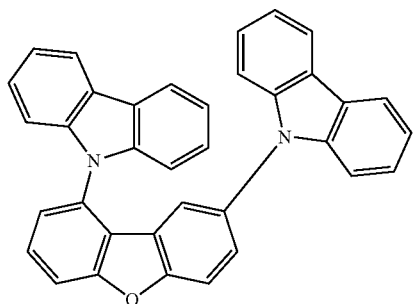
H-139
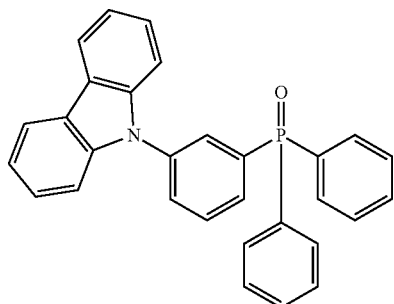
H-140
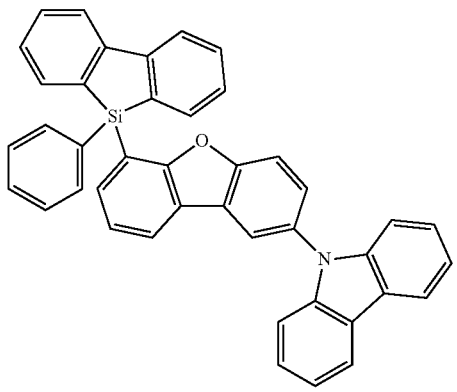
H-141
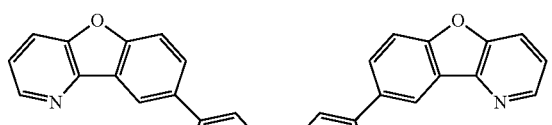
H-142
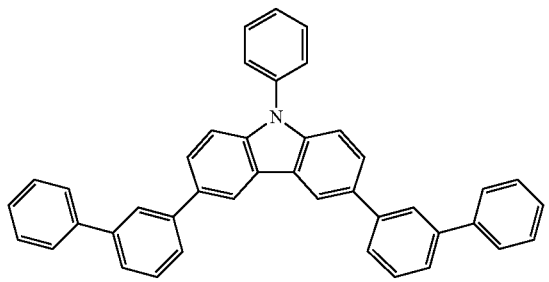
H-143
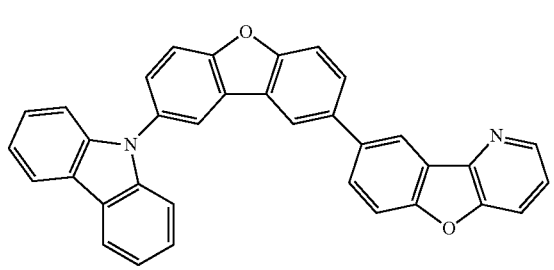

-continued
H-144
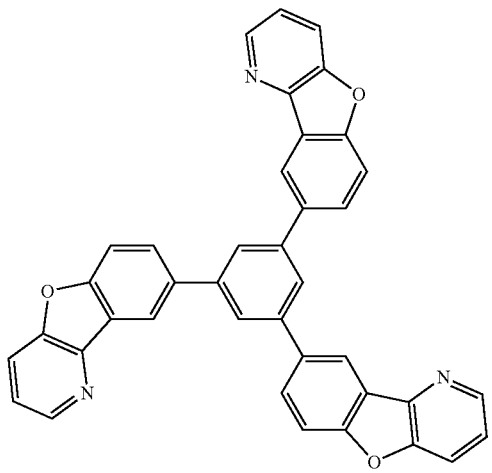
H-145
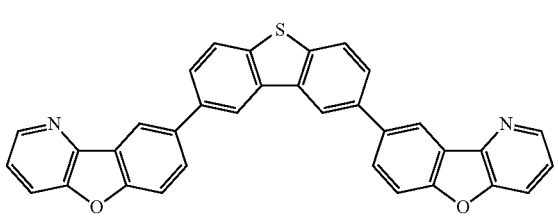
[Chem 58]
H-146
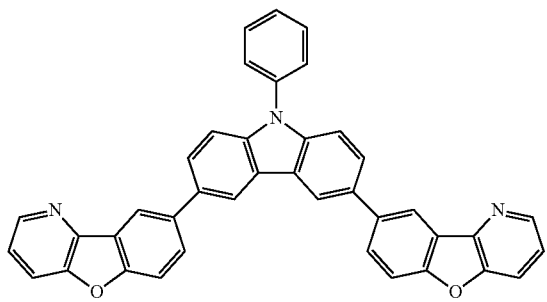
H-147
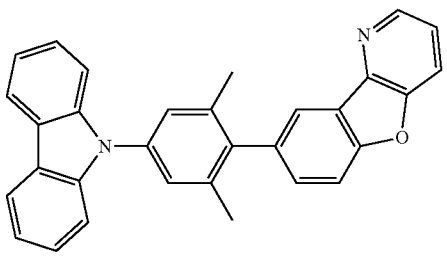
H-148
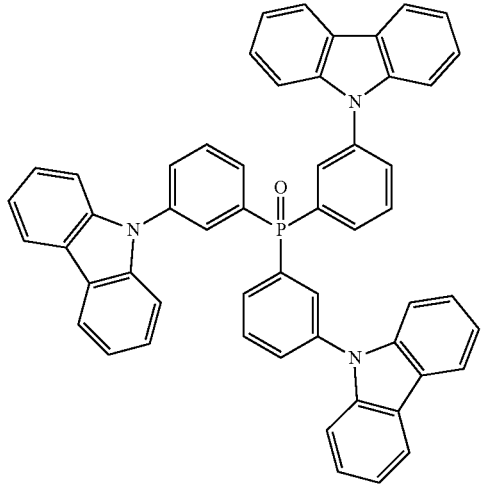
H-149
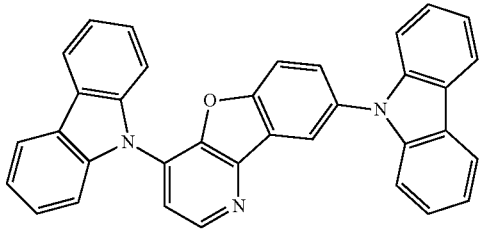

-continued
H-150
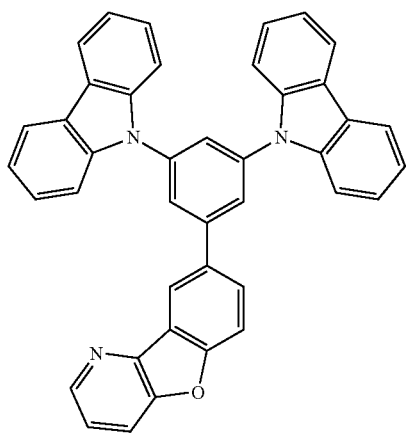
H-151
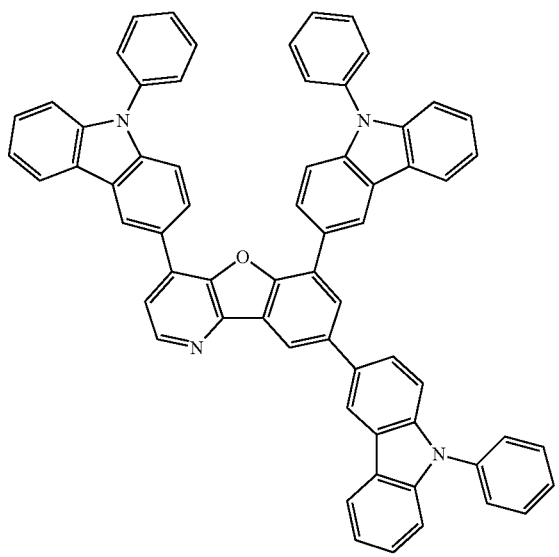
H-152
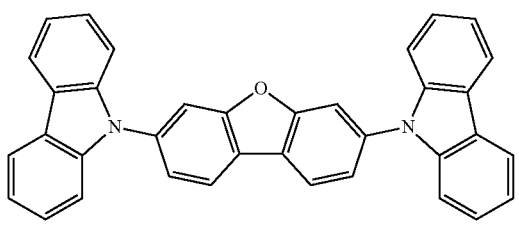
[Chem 59]
H-153
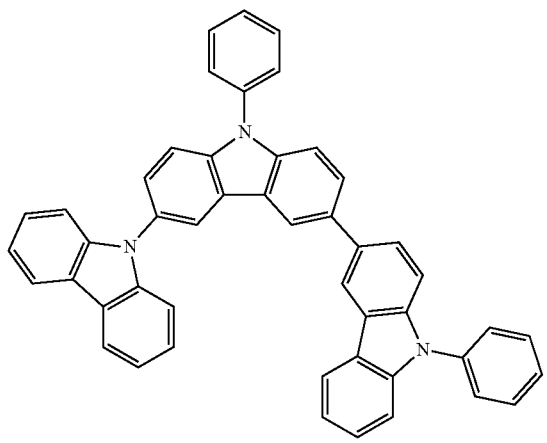
H-154
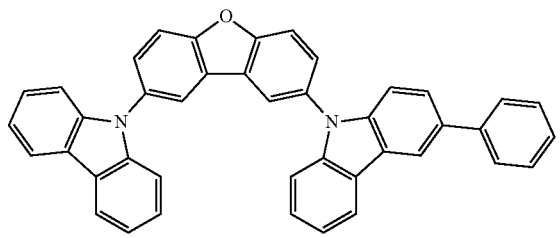
H-155
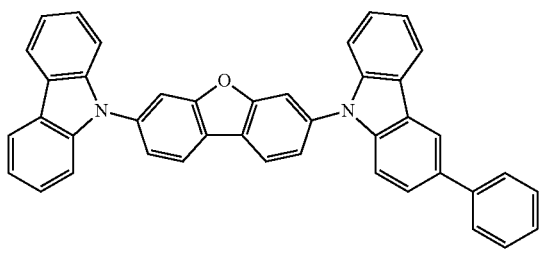
H-156
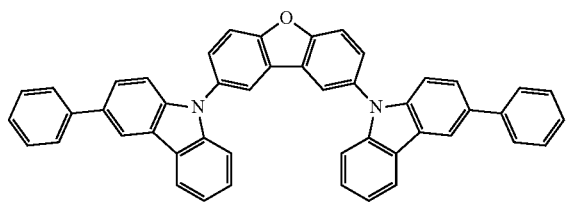

H-157
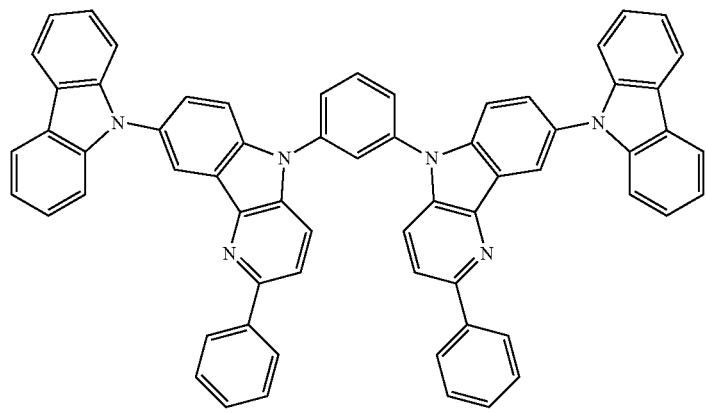
[Chem 60]
H-158
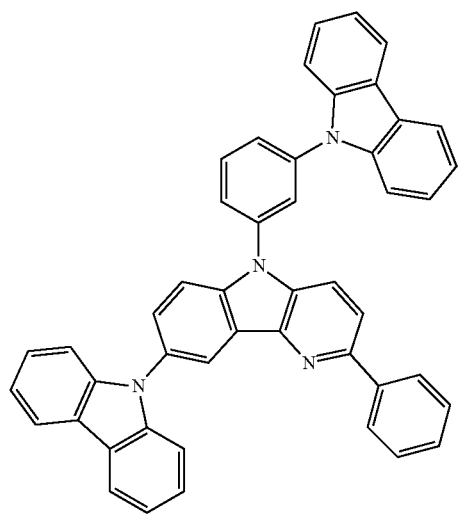
H-159
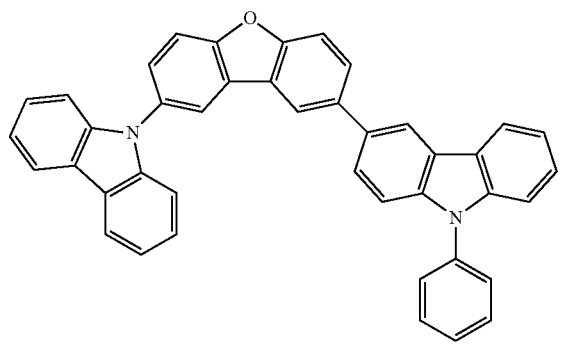
H-160
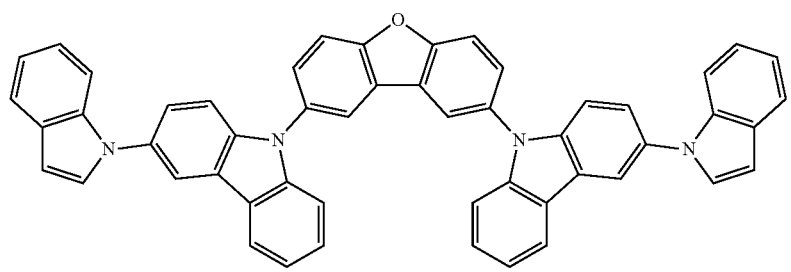

-continued
H-161
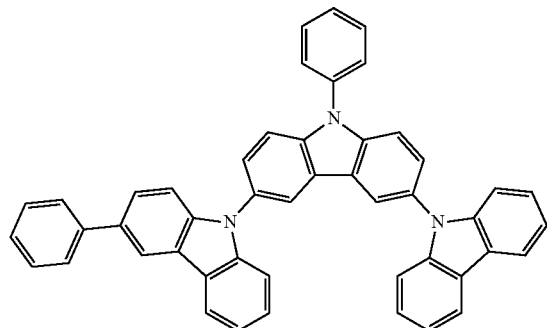
H-162
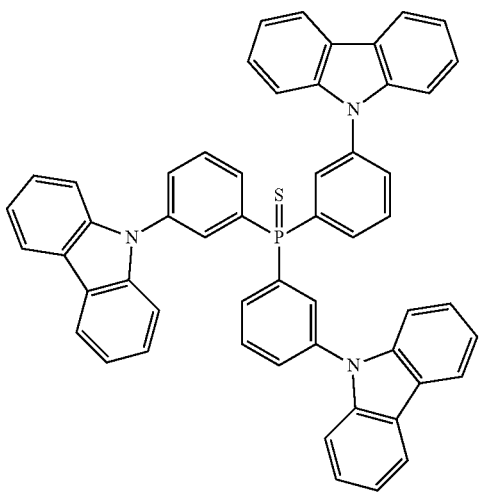
H-163
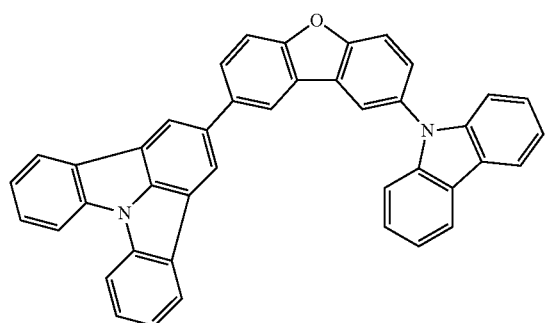
H-164
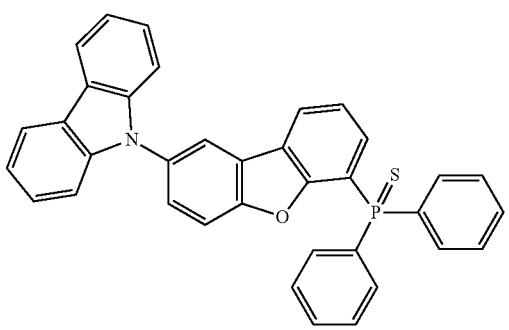
[Chem 61]
H-165
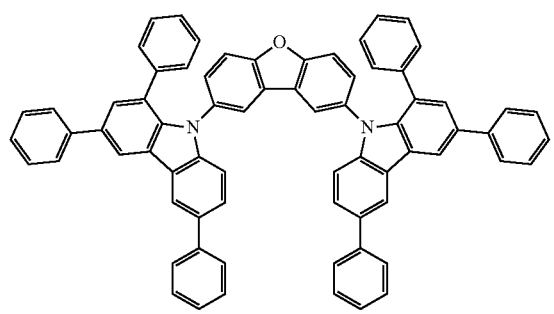
H-166
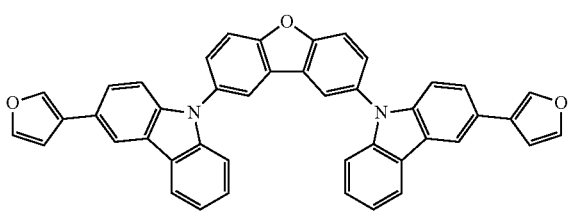

-continued
H-167
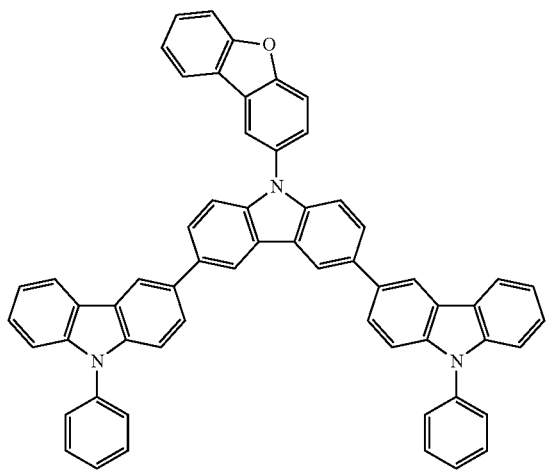
H-168
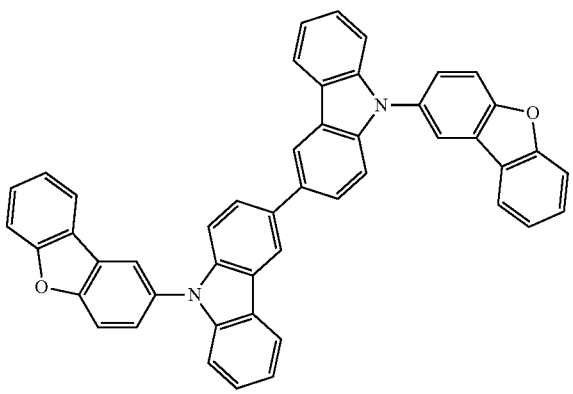
[Chem 62]
H-169
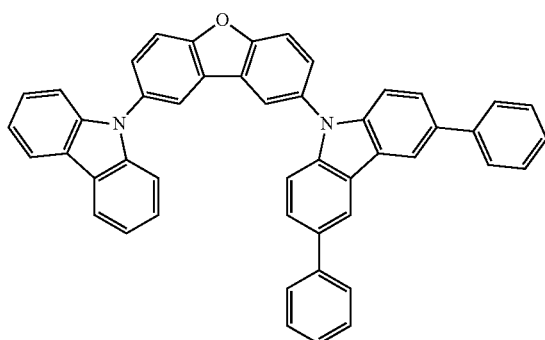
H-170
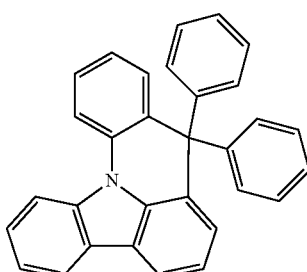
H-171
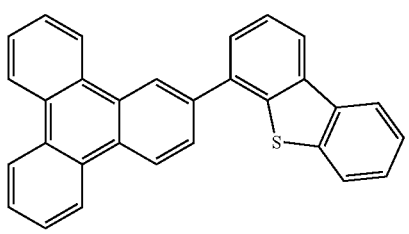
H-172
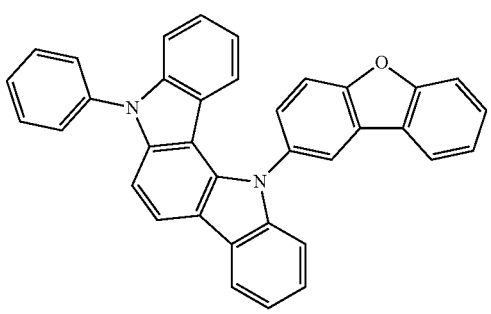

-continued
H-173
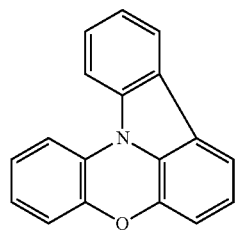
H-174
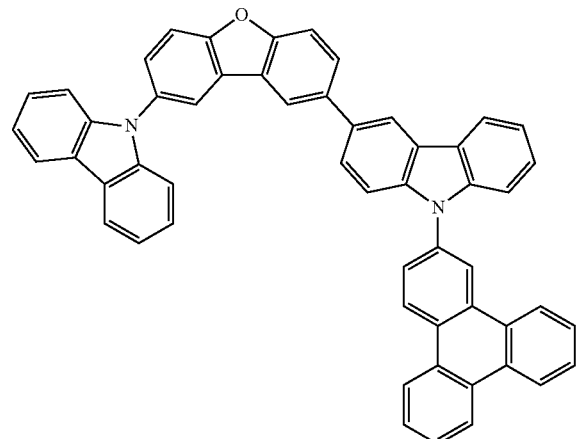
H-175
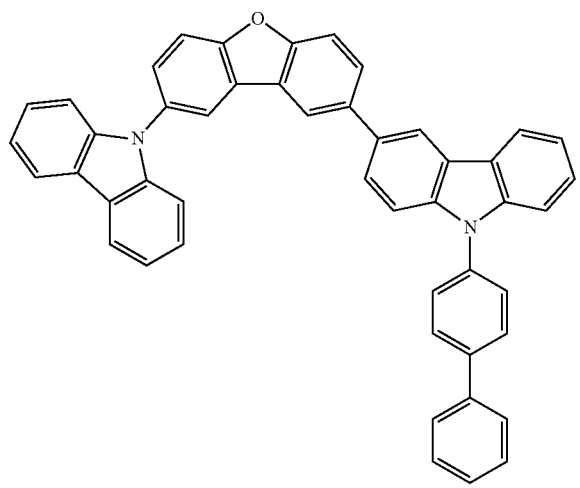
[Chem 63]
H-176
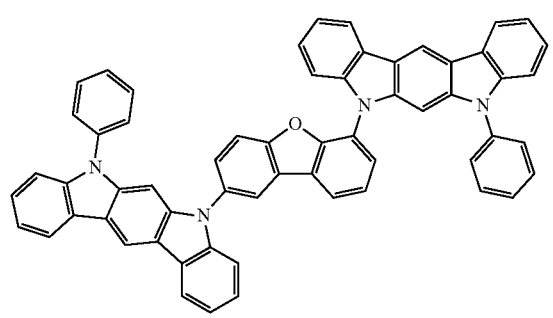
H-177
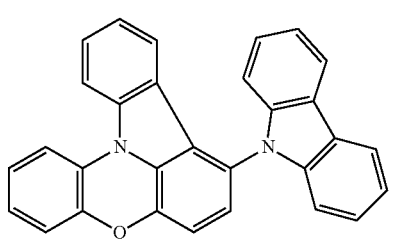

-continued
H-178
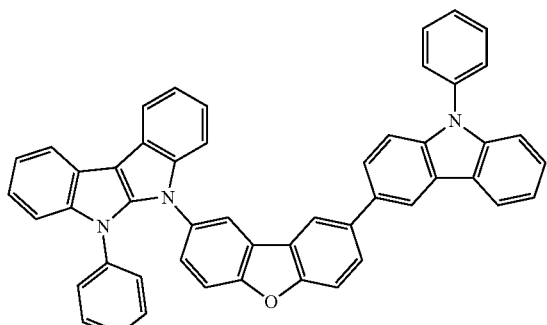
H-179
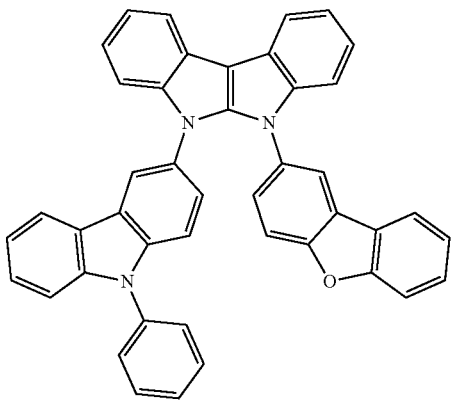
H-180
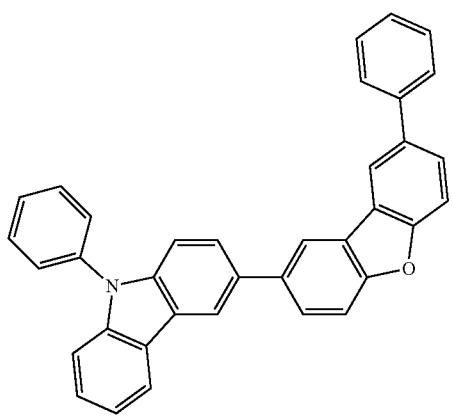
H-181
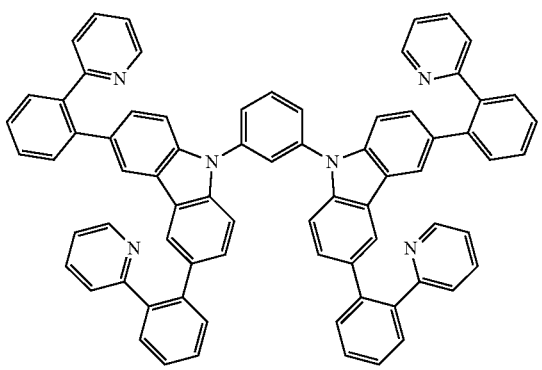
[Chem 64]
H-182
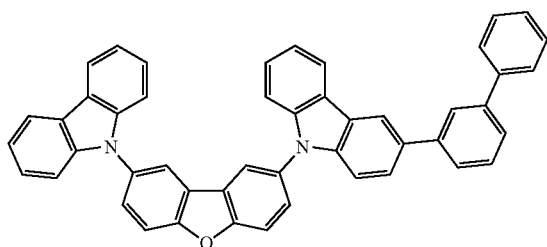
H-183
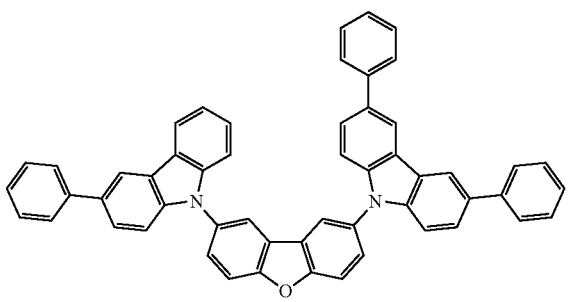
H-184
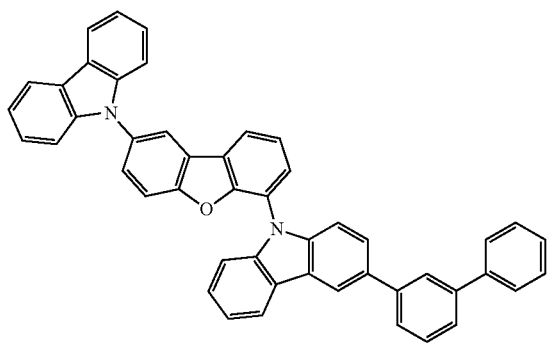
H-185
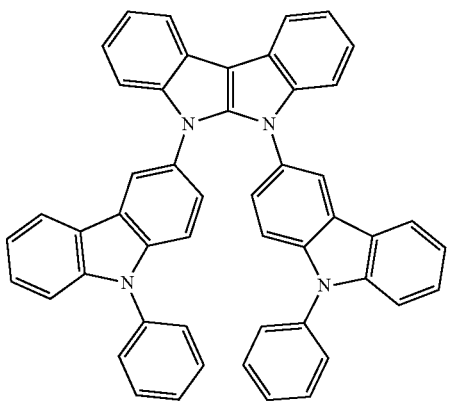

-continued
H-186
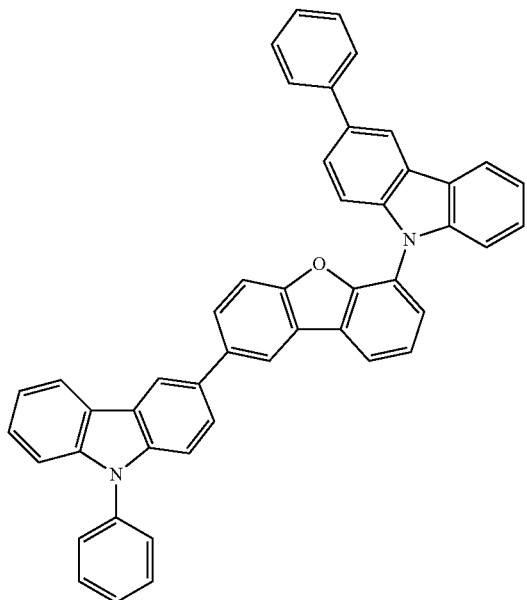
[Chem 65]
H-187
H-188
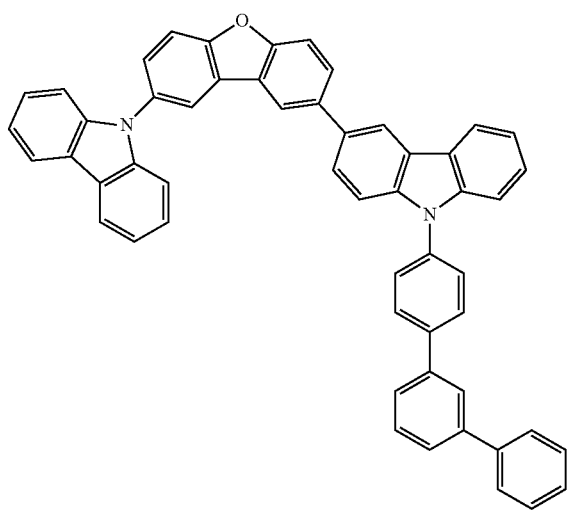
H-189
H-190
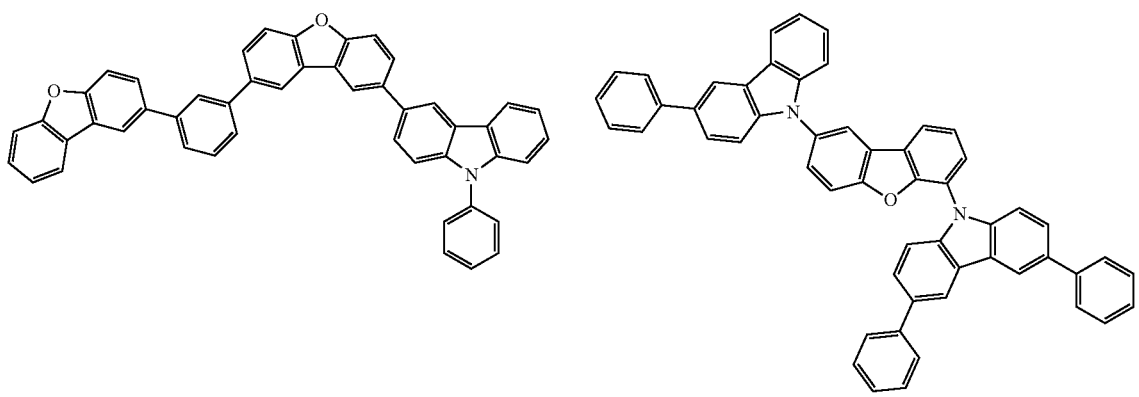

[Chem 66]
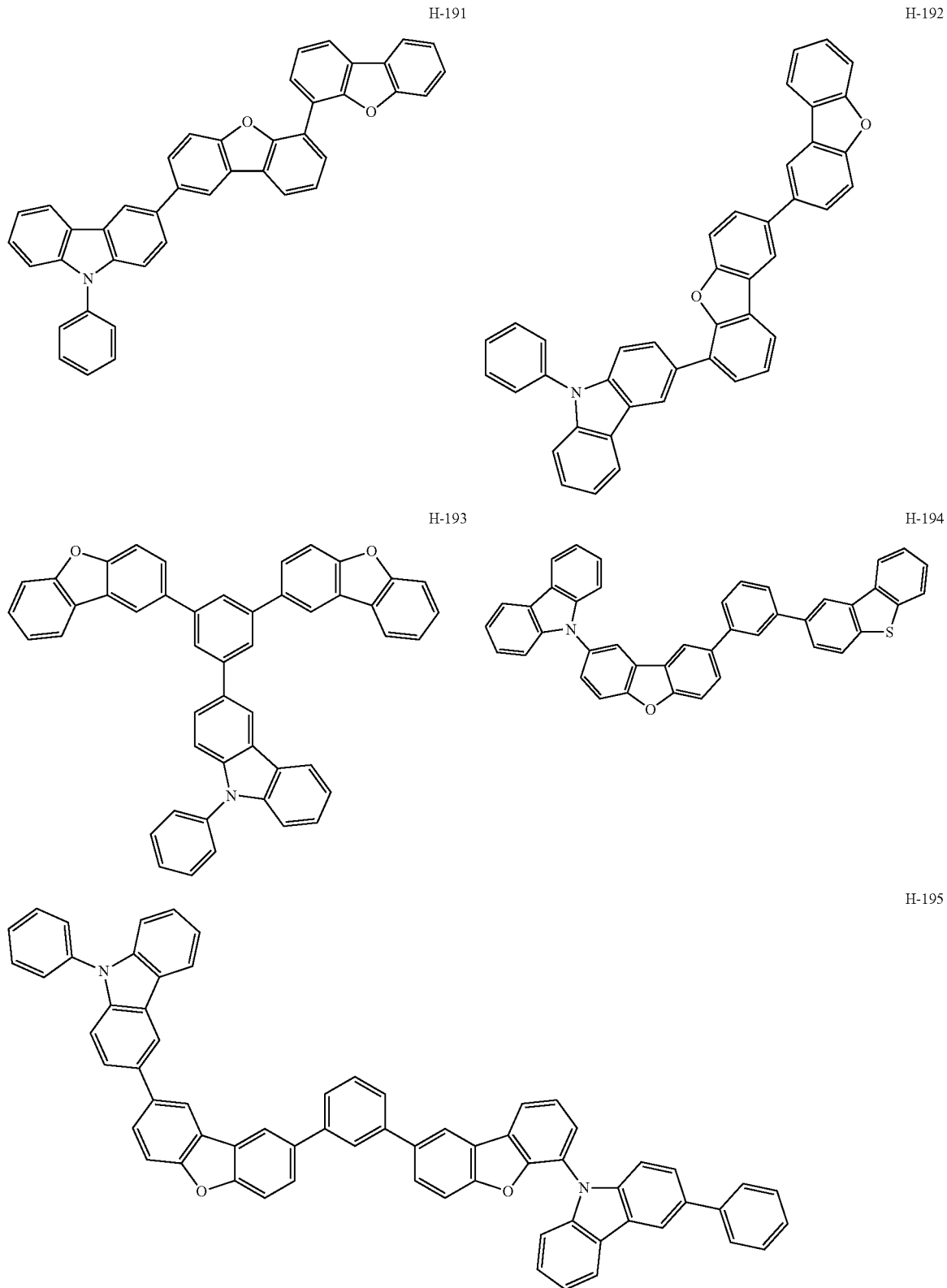

[Chem 67]
H-196
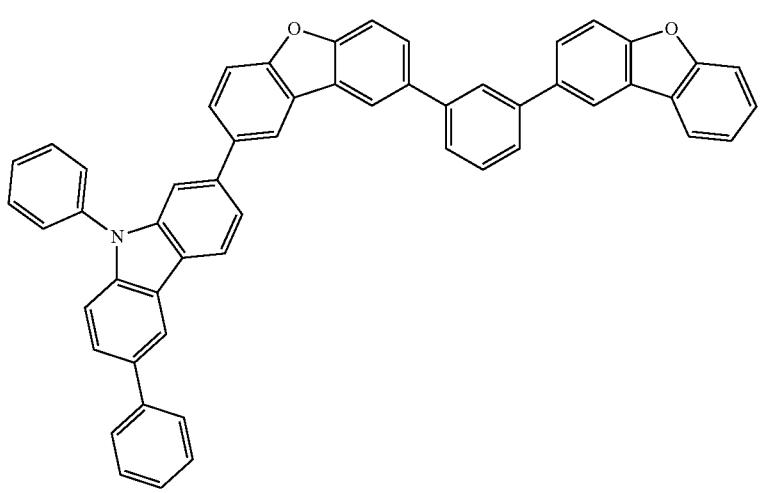
H-197
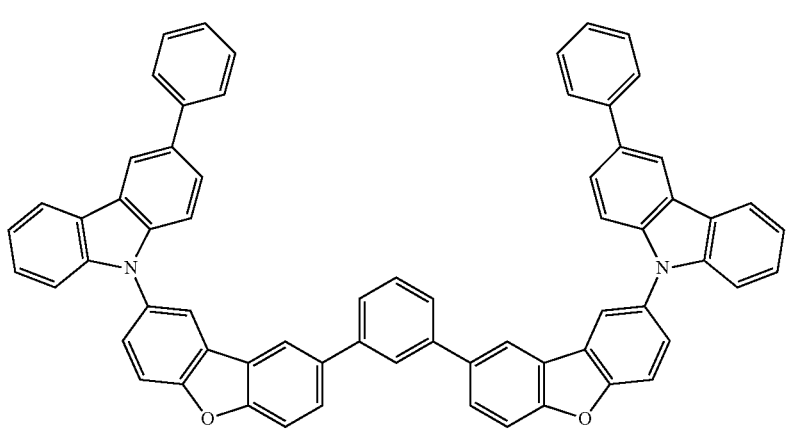
H-198
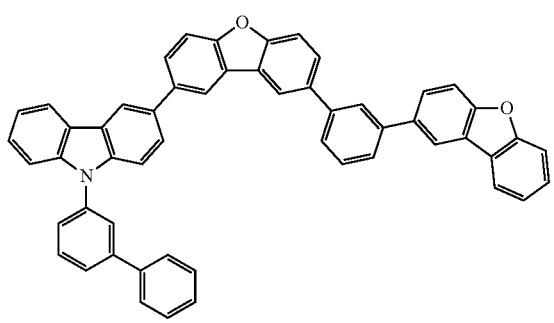
H-199
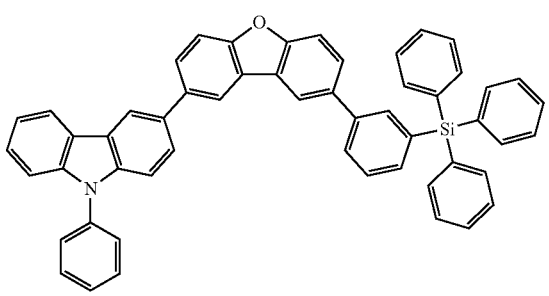

[Chem 68]
H-200
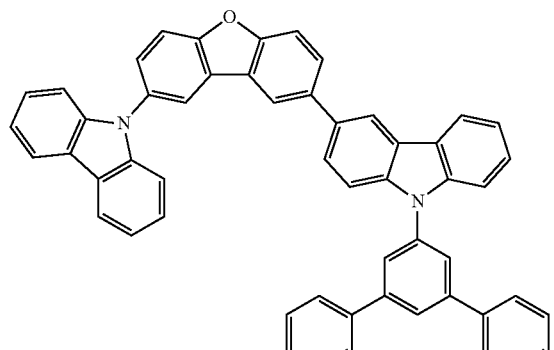
H-201
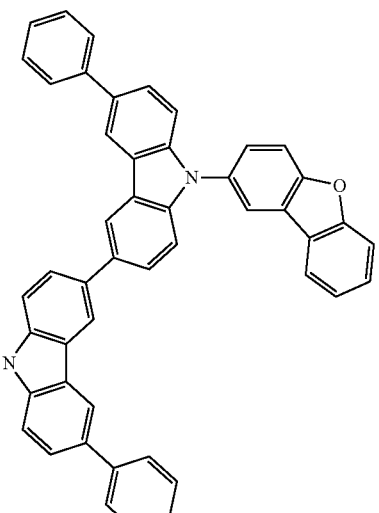
H-202
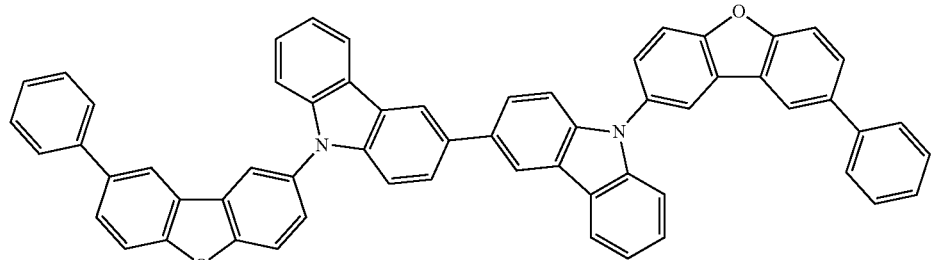
H-203
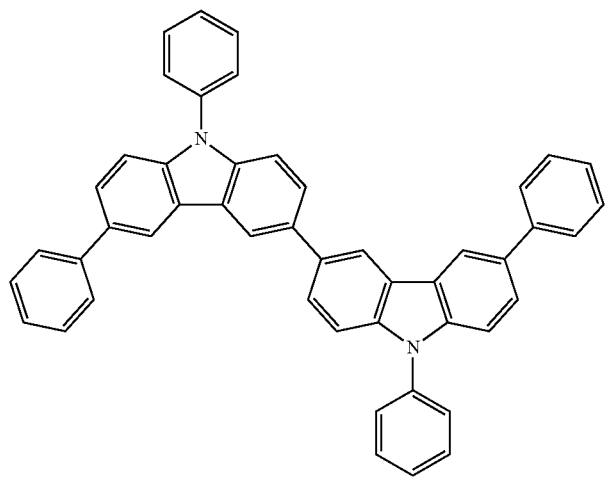
[Chem 69]
H-204
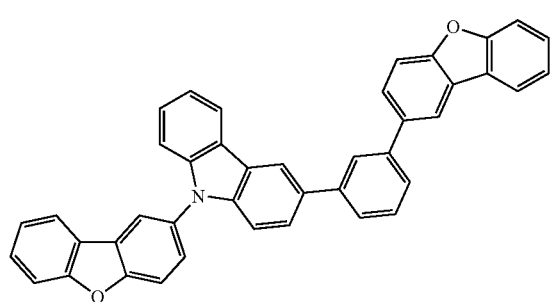
H-205
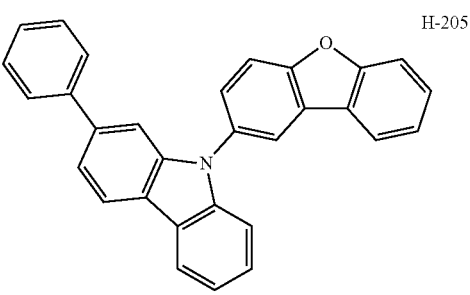

H-206
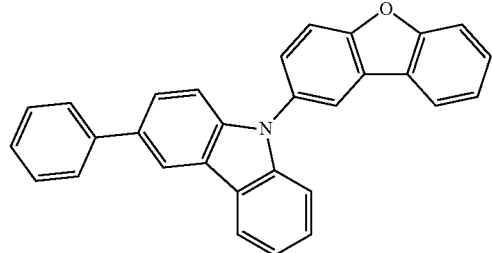
H-207
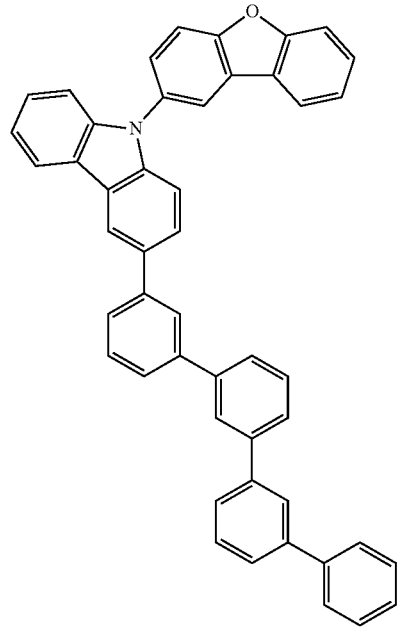
H-208
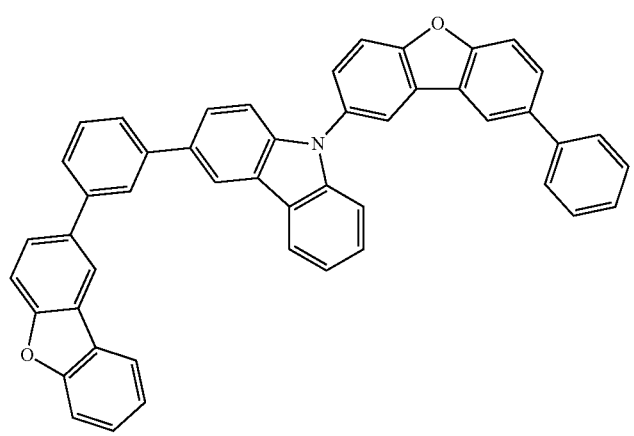
H-209
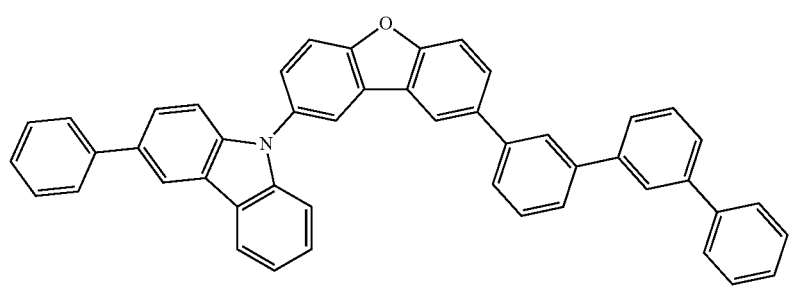
[Chem 70]
H-210
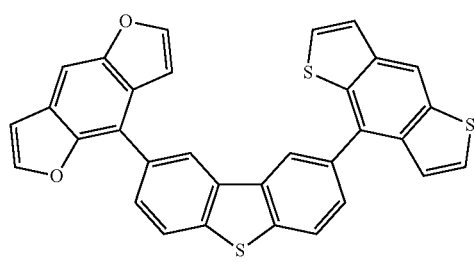
H-211
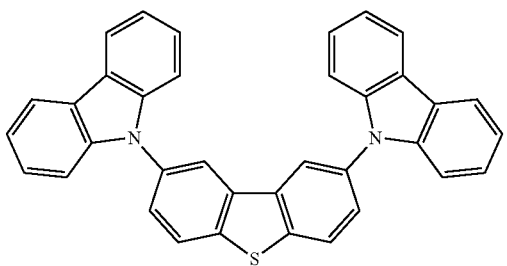

-continued
H-212
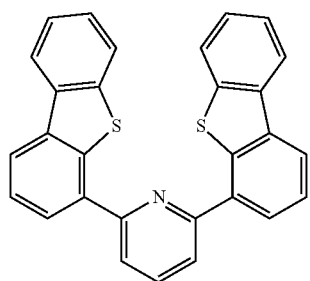
H-213
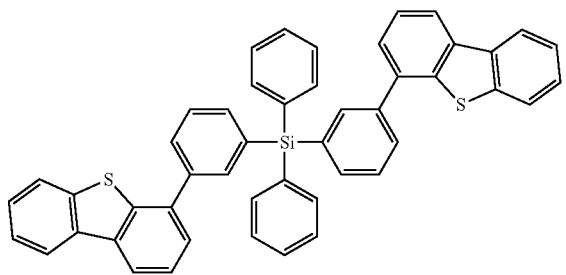
H-214
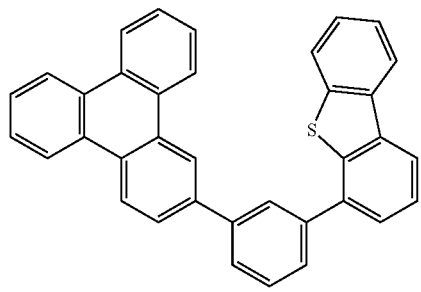
H-215
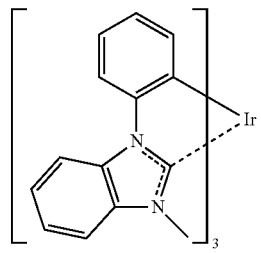
H-216
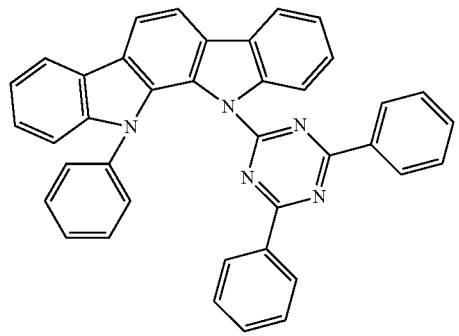
H-217
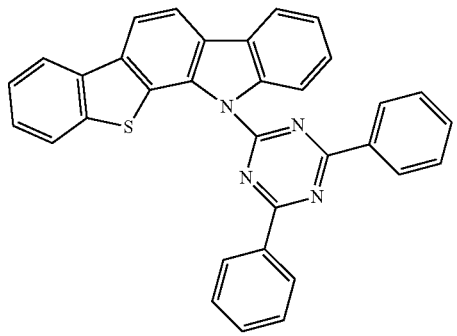
H-218
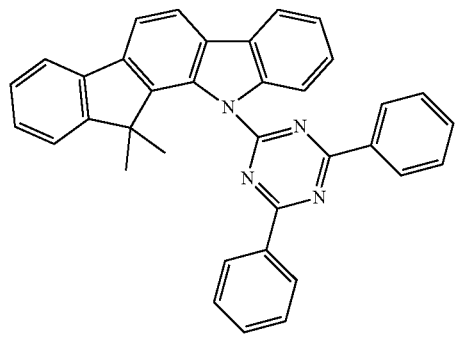
H-219
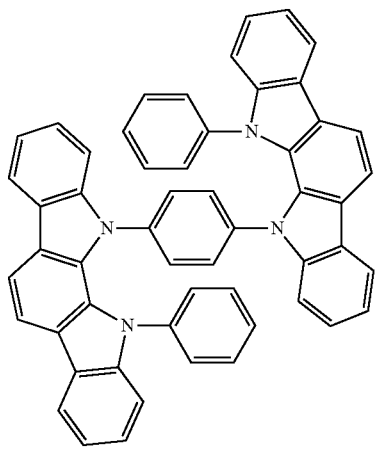

-continued
[Chem 71]
H-220
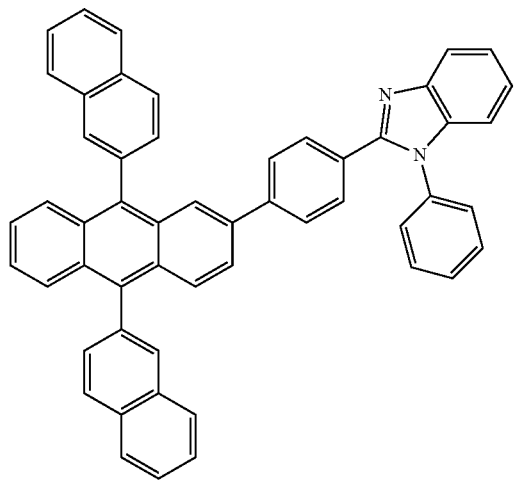
H-221
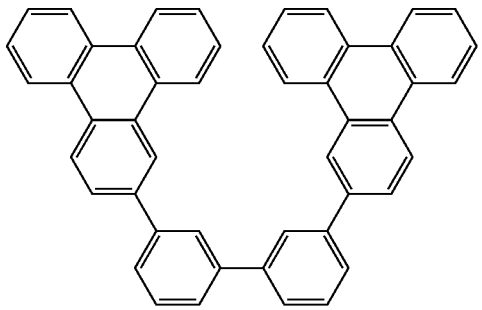
H-222
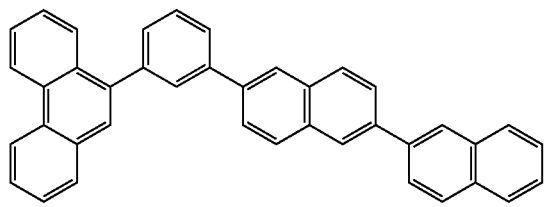
H-223
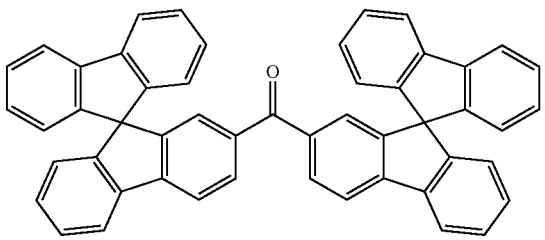
H-224
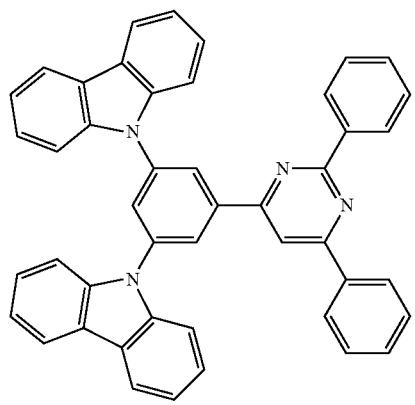
H-225
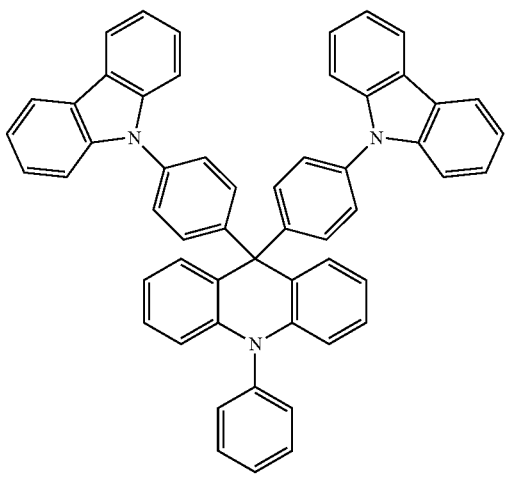

H-226

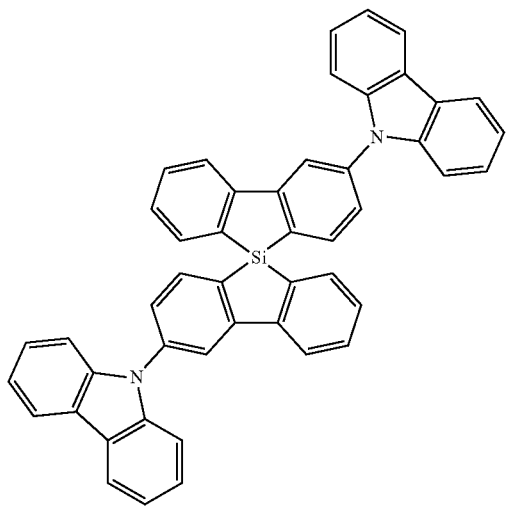

H-227

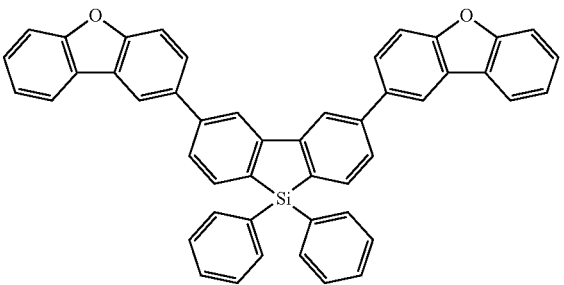

[Chem 72]

H-228

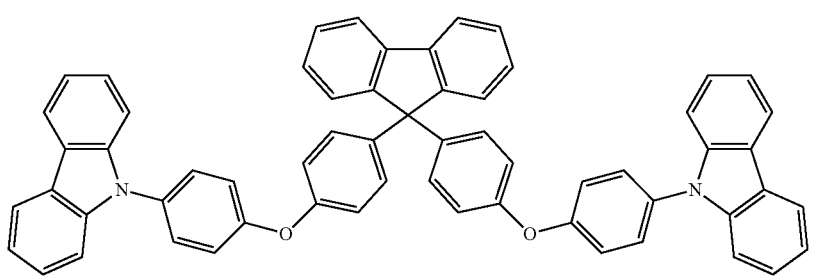

H-229

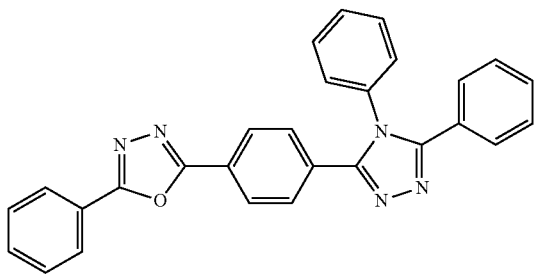

H-230

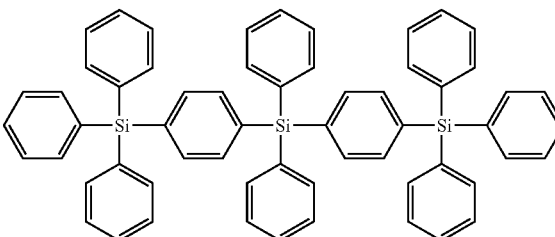

The preferred host compound used in the present invention may be a compound having a low molecular weight that can be purified by sublimation, or may be a polymer having repeating units.

The compound of low molecular weight has an advantage in that it can be readily purified by sublimation into a high-purity material. The compound may have any molecular weight capable of purification by sublimation. The molecular weight is preferably 3,000 or less, more preferably 2,000 or less.

The polymer or oligomer having repeating units has an advantage in that it is readily formed into a film by a wet process. The polymer, which has high Tg in general, is preferred in view of thermal resistance.

The host compound used in the present invention may be any polymer that can impart desired properties to the element, and is preferably a polymer having any of the structures represented by General formulae (I), (II), and (III-1) to (III-3) in the main chain or side chains. The polymer may have any molecular weight. The polymer preferably has a molecular weight of 5,000 or more or 10 or more repeating units.

The host compound preferably has a high glass transition temperature (Tg) in view of hole or electron transportability, prevention of an increase in emission wavelength, and stable operation of the organic EL element at high temperature. The Tg is preferably 90° C. or higher, more preferably 120° C. or higher.

The glass transition point (Tg) is determined by differential scanning calorimetry (DSC) in accordance with JIS K 7121-2012.

<<Electron Transporting Layer>>

The electron transporting layer according to the present invention, which is composed of a material having electron transportability, only needs to have a function of transferring electrons injected from the cathode to the luminous layer.

The electron transporting layer may have any thickness. The electron transporting layer typically has a thickness of 2 nm to 5 μm, more preferably 2 to 500 nm, still more preferably 5 to 200 nm.

During the extracting process of light emitted from the luminous layer through an electrode in the organic EL element, light extracted directly from the luminous layer is known to interfere with light reflected by the counter electrode. On light reflected by the cathode, the thickness of the electron transporting layer can be appropriately adjusted to several nanometers nm to several micrometers, to effectively utilize this interference phenomenon.

An increase in thickness of the electron transporting layer often causes an increase in voltage. Thus, an electron transporting layer having a large thickness preferably has an electron mobility of $10^{-5}$ cm$^2$/Vs or more.

The material used for the electron transporting layer (hereinafter referred to as "electron transporting material") may be any of traditional compounds capable of injecting or transporting electrons or blocking holes.

Examples of the electron transporting material include nitrogen-containing aromatic heterocyclic derivatives (e.g., carbazole derivatives, azacarbazole derivatives (wherein at least one of the carbon atoms forming the carbazole ring is replaced with a nitrogen atom), pyridine derivatives, pyrimidine derivatives, pyrazine derivatives, pyridazine derivatives, triazine derivatives, quinolone derivatives, quinoxaline derivatives, phenanthroline derivatives, azatriphenylene derivatives, oxazole derivatives, thiazole derivatives, oxadiazole derivatives, thiadiazole derivatives, triazole derivatives, benzimidazole derivatives, benzoxazole derivatives, and benzothiazole derivatives), dibenzofuran derivatives, dibenzothiophene derivatives, silole derivatives, and aromatic hydrocarbon derivatives (e.g., naphthalene derivatives, anthracene derivatives, and triphenylene derivatives).

The electron transporting material may be a metal complex having a quinolinol or dibenzoquinolinol skeleton as a ligand. Examples of the metal complex include tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol) aluminum, bis(8-quinolinol)zinc (Znq), and metal complexes where the central metal of any of these complexes is replaced with In, Mg, Cu, Ca, Sn, Ga or Pb.

The electron transporting material may also be a metal phthalocyanine, a metal-free phthalocyanine, or a metal or metal-free phthalocyanine having an end substituted by an alkyl group or a sulfonate group. The electron transporting material may also be a distyrylpyrazine derivative, which has been exemplified above as a material for the luminous layer, or may be an inorganic semiconductor material (e.g., n-type Si or n-type SiC) as in the hole injecting layer or the hole transporting layer.

The electron transporting material may be a polymer material prepared by incorporation of any of these materials into a polymer chain, or a polymer material having a main chain composed of any of these materials.

The electron transporting layer used in the present invention may be a highly negative (electron-rich) electron transporting layer doped with a dopant or a guest. Examples of the dopant include n-type dopants, such as metal compounds (e.g., metal complexes and metal halides). Examples of the electron transporting layer having the aforementioned configuration include those disclosed in Japanese Unexamined Patent Application Publication Nos. H4-297076, H10-270172, 2000-196140, and 2001-102175, and J. Appl. Phys., 95, 5773 (2004).

Examples of known electron transporting materials preferably used in the organic EL element of the present invention include, but are not limited to, compounds described in U.S. Pat. Nos. 6,528,187 and 7,230,107, U.S. Patent Application Publication Nos. 2005/0025993, 2004/0036077, 2009/0115316, 2009/0101870, and 2009/0179554, International Patent Publication WO2003/060956 and WO2008/132085, Appl. Phys. Lett., 75, 4 (1999), Appl. Phys. Lett., 79, 449 (2001), Appl. Phys. Lett., 81, 162 (2002), Appl. Phys. Lett., 81, 162 (2002), Appl. Phys. Lett., 79, 156 (2001), U.S. Pat. No. 7,964,293, U.S. Patent Application Publication No. 2009/030202, International Patent Publication WO2004/080975, WO2004/063159, WO2005/085387, WO2006/067931, WO2007/086552, WO2008/114690, WO2009/069442, WO2009/066779, WO2009/054253, WO2011/086935, WO2010/150593, and WO2010/047707, EP 2311826, Japanese Unexamined Patent Application Publication Nos. 2010-251675, 2009-209133, 2009-124114, 2008-277810, 2006-156445, 2005-340122, 2003-45662, 2003-31367, and 2003-282270, and International Patent Publication WO2012/115034.

Examples of more preferred electron transporting materials in the present invention include aromatic heterocyclic compounds containing at least one nitrogen atom, such as pyridine derivatives, pyrimidine derivatives, pyrazine derivatives, triazine derivatives, dibenzofuran derivatives, dibenzothiophene derivatives, azadibenzofuran derivatives, azadibenzothiophene derivatives, carbazole derivatives, azacarbazole derivatives, and benzimidazole derivatives.

These electron transporting materials may be used alone or in combination.

<<Hole Blocking Layer>>

The hole blocking layer functions as an electron transporting layer in a broad sense and is preferably composed of a material that transports electrons and has a low capability of transporting holes. The hole blocking layer transports electrons and blocks holes, thereby increasing the probability of recombination of electrons and holes.

The electron transporting layer described above may optionally be used as the hole blocking layer according to the present invention.

In the organic EL element of the present invention, the hole blocking layer is preferably disposed on the surface of the luminous layer adjacent to the cathode.

The hole blocking layer used in the present invention has a thickness of preferably 3 to 100 nm, more preferably 5 to 30 nm.

The hole blocking layer is preferably composed of a material used for the electron transporting layer described above, and is also preferably composed of any of the host compounds described above.

<<Electron Injecting Layer>>

The electron injecting layer used in the present invention (also referred to as "cathode buffer layer") is provided between the cathode and the luminous layer for a reduction in driving voltage and an increase in luminance. The electron injecting layer is detailed in Chapter 2 *"Denkyoku Zairyo* (Electrode Material)" (pp. 123-166) of Part 2 of *"Yuuki EL Soshi to Sono Kogyoka Saizensen* (Organic EL Devices and Their Advanced Industrialization) (published by NTS Corporation, Nov. 30, 1998)."

In the present invention, the electron injecting layer is optionally provided. The electron injecting layer may be disposed between the cathode and the luminous layer as described above, or between the cathode and the electron transporting layer.

The electron injecting layer is preferably composed of a very thin film, and has a thickness of preferably 0.1 to 5 nm, which may vary depending on the raw material used. The electron injecting layer may be composed of a non-uniform film containing a discontinuously distributed material.

The electron injecting layer is also detailed in Japanese Unexamined Patent Application Publication Nos. H6-325871, H9-17574, and H10-74586. Examples of materials preferably used for the electron injecting layer include metals, such as strontium and aluminum; alkali metal compounds, such as lithium fluoride, sodium fluoride, and potassium fluoride; alkaline earth metal compounds, such as magnesium fluoride and calcium fluoride; metal oxides, such as aluminum oxide; and metal complexes, such as lithium 8-hydroxyquinolinate (Liq). The electron transporting materials described above may also be used.

These materials for the electron injecting layer may be used alone or in combination.

<<Hole Transporting Layer>>

The hole transporting layer according to the present invention, which is composed of a material having hole transportability, only needs to have a function of transferring holes injected from the anode to the luminous layer.

The hole transporting layer may have any thickness. The electron transporting layer has a thickness of generally 5 nm to 5 μm, more preferably 2 to 500 nm, still more preferably 5 to 200 nm.

The material used for the hole transporting layer (hereinafter referred to as "hole transporting material") may be any of traditional compounds capable of injecting or transporting holes or blocking electrons.

Examples of the hole transporting material include porphyrin derivatives, phthalocyanine derivatives, oxazole derivatives, oxadiazole derivatives, triazole derivatives, imidazole derivatives, pyrazoline derivatives, pyrazolone derivatives, phenylenediamine derivatives, hydrazone derivatives, stilbene derivatives, polyarylalkane derivatives, triarylamine derivatives, carbazole derivatives, indolocarbazole derivatives, isoindole derivatives, acene derivatives (e.g., anthracene and naphthalene), fluorene derivatives, fluorenone derivatives, poly(vinylcarbazole), polymer materials and oligomers having an aromatic amine in the main chain or side chain, polysilanes, and conductive polymers and oligomers (e.g., PEDOT/PSS, aniline copolymers, polyaniline, and polythiophene).

Examples of the triarylamine derivatives include benzidine derivatives, such as α-NPD (4,4'-bis[N-(1-naphthyl)-N-phenylamino]biphenyl), starburst amine derivatives, such as MTDATA, and compounds having fluorene or anthracene on the bonding cores of triarylamines.

The hole transporting material may also be hexaazatriphenylene derivatives described in Japanese Translation of PCT International Application Publication No. 2003-519432 and Japanese Unexamined Patent Application Publication No. 2006-135145.

The hole transporting layer may be a highly positive hole transporting layer doped with an impurity. Examples of such an electron transporting layer include those described in Japanese Unexamined Patent Application Publication Nos. H4-297076, 2000-196140, and 2001-102175, and J. Appl. Phys., 95, 5773 (2004).

The hole transporting material may be a p-type hole transporting material or an inorganic compound (e.g., p-type Si or p-type SiC) described in Japanese Unexamined Patent Application Publication No. H11-251067 and J. Huang, et al., Applied Physics Letters 80 (2002), p. 139. The hole transporting material is preferably an ortho-metalated organometallic complex having Ir or Pt as a central metal, such as $Ir(ppy)_3$.

Among the hole transporting materials described above, preferred are triarylamine derivatives, carbazole derivatives, indolocarbazole derivatives, azatriphenylene derivatives, organometallic complexes, and polymer materials and oligomers having an aromatic amine in the main chain or side chain.

Examples of known hole transporting materials preferably used in the organic EL element of the present invention include, but are not limited to, compounds described in the aforementioned publications and described in Appl. Phys. Lett., 69, 2160 (1996), J. Lumin., 72-74, 985 (1997), Appl. Phys. Lett., 78, 673 (2001), Appl. Phys. Lett., 90, 183503 (2007), Appl. Phys. Lett., 90, 183503 (2007), Appl. Phys. Lett., 51, 913 (1987), Synth. Met., 87, 171 (1997), Synth. Met., 91, 209 (1997), Synth. Met., 111, 421 (2000), SID Symposium Digest, 37, 923 (2006), J. Mater. Chem., 3, 319 (1993), Adv. Mater., 6, 677 (1994), Chem. Mater., 15, 3148 (2003), U.S. Patent Application Publication Nos. 2003/0162053, 2002/0158242, 2006/0240279, and 2008/0220265, U.S. Pat. No. 5,061,569, International Patent Publication WO2007/002683 and WO2009/018009, EP No. 650955, U.S. Patent Application Publication Nos. 2008/0124572, 2007/0278938, 2008/0106190, and 2008/0018221, International Patent Publication WO2012/115034, Japanese Translation of PCT International Application Publication No. 2003-519432, Japanese Unexamined Patent Application Publication No. 2006-135145, and U.S. patent application Ser. No. 13/585,981.

These hole transporting materials may be used alone or in combination.

<<Electron Blocking Layer>>

The electron blocking layer functions as a hole transporting layer in a broad sense and is preferably composed of a material that transports holes and has a low capability of transporting electrons. The electron blocking layer transports holes and blocks electros, thereby increasing the probability of recombination of electrons and holes.

The aforementioned hole transporting layer may optionally be used as the electron blocking layer in the present invention.

In the organic EL element of the present invention, the electron blocking layer is preferably disposed on the surface of the luminous layer adjacent to the anode.

The electron blocking layer used in the present invention has a thickness of preferably 3 to 100 nm, more preferably 5 to 30 nm.

The electron blocking layer is preferably composed of a material used for the hole transporting layer described above, and is also preferably composed of any of the host compounds described above.

<<Hole Injecting Layer>>

The hole injecting layer according to the present invention (also referred to as "anode buffer layer") is provided between the anode and the luminous layer for a reduction in driving voltage and an increase in luminance. The hole injecting layer is detailed in Chapter 2 *"Denkyoku Zairyo (Electrode Material)"* (pp. 123-166) of Part 2 of *"Yuuki EL Soshi to Sono Kogyoka Saizensen* (Organic EL Devices and Their Advanced Industrialization) (published by NTS Corporation, Nov. 30, 1998)."

In the present invention, the hole injecting layer is optionally provided. The hole injecting layer may be disposed between the anode and the luminous layer as described above, or between the anode and the hole transporting layer.

The hole injecting layer is also detailed in Japanese Unexamined Patent Application Publication Nos. H9-45479, H9-260062, and H8-288069. Examples of the material for the hole injecting layer include those used for the hole transporting layer described above.

Examples of particularly preferred materials include phthalocyanine derivatives, such as copper phthalocyanine; hexaazatriphenylene derivatives disclosed in Japanese Translation of PCT International Application Publication No. 2003-519432 and Japanese Unexamined Patent Application Publication No. 2006-135145; metal oxides, such as vanadium oxide; amorphous carbon; conductive polymers, such as polyaniline (emeraldine) and polythiophene; ortho-metalated complexes, such as a tris(2-phenylpyridine) iridium complex; and triarylamine derivatives.

These materials for the hole injecting layer may be used alone or in combination.

<<Additives>>

Each of the aforementioned organic layers according to the present invention may contain any other additive.

Examples of the additive include halogens, such as bromine, iodine, and chlorine; halides; and compounds, complexes, and salts of alkali metals, alkaline earth metals, and transition metals, such as Pd, Ca, and Na.

The additive content of the organic layer may be appropriately determined. The additive content is preferably 1,000 ppm or less, more preferably 500 ppm or less, still more preferably 50 ppm or less, relative to the entire mass of the layer containing the additive.

The additive content may fall outside of this range for improvement of electron or hole transportability or effective energy transfer of excitons.

<<Formation of Organic Layer>>

Now will be described a process of forming the organic layers (hole injecting layer, hole transporting layer, luminous layer, hole blocking layer, electron transporting layer, and electron injecting layer) according to the present invention.

The organic layer according to the present invention can be formed by any known process, such as a vacuum vapor deposition process or a wet process.

Examples of the wet process include spin coating, casting, ink jetting, printing, dye coating, blade coating, roll coating, spray coating, curtain coating, and the Langmuir-Blodgett (LB) method. Preferred are processes highly suitable for a roll-to-roll system, such as die coating, roll coating, ink jetting, and spray coating, in view of easy formation of a thin homogeneous film and high productivity.

Examples of the liquid medium for dissolution or dispersion of the organic EL materials used in the present invention include ketones, such as methyl ethyl ketone and cyclohexanone; fatty acid esters, such as ethyl acetate; halogenated hydrocarbons, such as dichlorobenzene; aromatic hydrocarbons, such as toluene, xylene, mesitylene, and cyclohexylbenzene; aliphatic hydrocarbons, such as cyclohexane, decalin, and dodecane; and organic solvents, such as DMF and DMSO.

Examples of the usable dispersion technique include ultrasonic dispersion, high shearing force dispersion, and media dispersion.

Individual layers may be formed through different processes. Conditions of a vapor evaporation process for formation of a layer may vary depending on the type of a compound used. In general, the process is performed under the following conditions: a boat heating temperature of 50 to 450° C., a vacuum of $10^{-6}$ to $10^{-2}$ Pa, a deposition rate of 0.01 to 50 nm/second, a substrate temperature of −50 to 300° C., and a layer (film) thickness of 0.1 nm to 5 μm (preferably 5 to 200 nm).

The organic EL element of the present invention is preferably produced by forming the aforementioned organic layers (including the hole injecting layer and the cathode) through a single vacuuming process. The vacuuming process may be intermitted, and then the layers may be formed by a deposition process other than the vacuuming process. In such a case, the process is preferably performed in a dry inert gas atmosphere.

<<Anode>>

The anode of the organic EL element is preferably composed of an electrode material having a high work function (4 eV or more, preferably 4.5 eV or more), such as a metal, an alloy, a conductive compound, or a mixture thereof. Examples of the electrode material include metals, such as Au, and transparent conductive materials, such as CuI, indium thin oxide (ITO), $SnO_2$, and ZnO. An amorphous material capable of forming a transparent conductive film, such as IDIXO ($In_2O_3$—ZnO), may also be used.

The anode can be prepared through formation of a thin film from any of the aforementioned electrode materials by vapor deposition or sputtering, followed by patterning through photolithography, to form a desired pattern. If high patterning accuracy is not required (i.e., an accuracy of about 100 μm or more), a pattern may be formed with a mask having a desired shape during deposition or sputtering of the aforementioned electrode material.

In use of an applicable substance (e.g., an organic conductive compound), the anode may be prepared by a wet process, such as printing or coating. For extraction of emitted light through the anode, the transmittance of the anode is preferably 10% or more, and the sheet resistance of the anode is preferably several hundred ohms/square or less.

The anode has a thickness of typically 10 nm to 1 μm, preferably 10 to 200 nm, which may vary depending on the material used.

<<Cathode>>

The cathode is composed of an electrode material having a low work function (4 eV or less), such as a metal (referred to as "electron-injecting metal"), an alloy, a conductive compound, or a mixture thereof. Examples of the electrode material include sodium, sodium-potassium alloys, magnesium, lithium, magnesium-copper mixtures, magnesium-silver mixtures, magnesium-aluminum mixtures, magnesium-indium mixtures, aluminum-aluminum oxide ($Al_2O_3$) mixtures, indium, lithium-aluminum mixtures, aluminum, and rare earth metals. Among these materials, preferred is a mixture of an electron-injecting metal and a second metal that is stable and has a work function higher than that of the electron-injecting material, in view of electron injecting ability and resistance against oxidation, for example. Examples of the mixture include magnesium-silver mixtures, magnesium-aluminum mixtures, magnesium-indium mixtures, aluminum-aluminum oxide ($Al_2O_3$) mixtures, lithium-aluminum mixtures, and aluminum.

The cathode can be prepared through formation of a thin film from any of the aforementioned electrode materials by vapor deposition or sputtering. The cathode has a sheet resistance of preferably several hundred ohms/square or less, and has a thickness of typically 10 nm to 5 μm, preferably 50 to 200 nm.

From the viewpoint of transmission of emitted light, the anode or cathode of the organic EL element is preferably transparent or translucent for an increase in luminance.

The cathode can be provided with transparency or translucency by formation of a film having a thickness of 1 to 20 nm on the cathode from any of the aforementioned metals, followed by coating of the film with any of the transparent conductive materials used for the anode. The application of this process can produce an organic El element including a transparent anode and a transparent cathode.

[Supporting Substrate]

The supporting substrate used for the organic EL element of the present invention (hereinafter also referred to as "substrate," "base," or "support") may be composed of any glass or plastic material, and may be transparent or opaque. In extraction of light through the supporting substrate, the supporting substrate should preferably be transparent. Examples of preferred transparent supporting substrates include glass films, quartz films, and transparent resin films. Particularly preferred is a resin film that can impart flexibility to the organic EL element.

Examples of the resin film include films of polyesters, such as poly(ethylene terephthalate) (PET) and poly(ethylene naphthalate) (PEN), polyethylene, polypropylene, cellophane, cellulose esters and their derivatives, such as cellulose diacetate, cellulose triacetate (TAC), cellulose acetate butyrate, cellulose acetate propionate (CAP), cellulose acetate phthalate, and cellulose nitrate, poly(vinylidene chloride), poly(vinyl alcohol), poly(ethylene-vinyl alcohol), syndiotactic polystyrene, polycarbonates, norbornene resins, polymethylpentene, polyetherketones, polyimides, polyethersulfones (PES), poly(phenylene sulfide), polysulfones, polyetherimides, polyetherketoneimides, polyamides, fluororesins, nylons, poly(methyl methacrylate), acrylic resins, polyarylates, and cycloolefin resins, such as ARTON (trade name, manufactured by JSR Corp.) and APEL (trade name, manufactured by Mitsui Chemicals Inc.).

The surface of the resin film may be provided with an inorganic or organic coating film or a hybrid coating film composed of both. The coating film is preferably a barrier film having a water vapor permeability ($25\pm0.5°$ C., relative humidity ($90\pm2$)% RH) of 0.01 g/($m^2 \cdot 24$ h) or less as determined in accordance with JIS K 7129-1992. The coating film is more preferably a high barrier film having an oxygen permeability of $1\times10^{-3}$ mL/$m^2 \cdot 24$ h·atm or less as determined in accordance with JIS K 7126-1987 and a water vapor permeability of $1\times10^{-5}$ g/$m^2 \cdot 24$ h or less.

The barrier film may be formed from any material capable of preventing intrusion of a substance that causes degradation of the organic EL element, such as moisture or oxygen. Examples of the material include silicon oxide, silicon dioxide, and silicon nitride. In view of enhancement of the strength, the barrier film preferably has a layered structure composed of an inorganic layer and an organic material layer. The inorganic layer and the organic layer may be disposed in any order. Preferably, a plurality of inorganic layers and organic layers are alternately disposed.

The barrier film may be formed by any known process. Examples of the process include vacuum vapor deposition, sputtering, reactive sputtering, molecular beam epitaxy, ionized-cluster beam deposition, ion plating, plasma polymerization, atmospheric pressure plasma polymerization, plasma CVD, laser CVD, thermal CVD, and coating. In particular, the barrier film is preferably formed through atmospheric pressure plasma polymerization as disclosed in Japanese Unexamined Patent Application Publication No. 2004-68143.

Examples of the opaque supporting substrate include metal plates and films composed of aluminum and stainless steel, opaque resin substrates, and ceramic substrates.

The organic EL element of the present invention has an external quantum efficiency at room temperature (25° C.) of preferably 1% or more, more preferably 5% or more.

The external quantum efficiency (%) is determined by the following expression:

external quantum efficiency (%)=(the number of photons emitted to the outside of the organic EL element/the number of electrons flowing through the organic EL element)×100.

The supporting substrate may be used in combination with a hue improving filter (e.g., a color filter). Alternatively, the supporting substrate may be used in combination with a color conversion filter that converts the color of light emitted from the organic EL element into multiple colors with a fluorescent material.

[Sealing]

Examples of the means for sealing of the organic EL element of the present invention include a process of bonding a sealing member to the electrode and the supporting substrate with an adhesive. The sealing member only needs to be disposed to cover a display area of the organic EL element. The sealing member may be in the form of concave plate or flat plate. The sealing member may have transparency or electrical insulating properties.

Examples of the sealing member include a glass plate, a composite of polymer plate and film, and a composite of metal plate and film. Examples of the glass plate include plates of soda-lime grass, glass containing barium and strontium, lead glass, aluminosilicate glass, borosilicate glass, barium borosilicate glass, and quartz. Examples of the polymer plate include plates of polycarbonate, acrylic resin, poly(ethylene terephthalate), poly(ether sulfide), and polysulfone. Examples of the metal plate include plates composed of one or more metals selected from the group consisting of stainless steel, iron, copper, aluminum, magnesium, nickel, zinc, chromium, titanium, molybdenum, silicon, germanium, and tantalum, and plates composed of alloys of these metals.

In the present invention, a polymer film or a metal film is preferably used for reducing the thickness of the organic EL element. The polymer film preferably has an oxygen permeability of $1\times10^{-3}$ mL/$m^2 \cdot 24$ h or less as determined in accordance with JIS K 7126-1987 and a water vapor permeability ($25\pm0.5°$ C., relative humidity of $90\pm2$%) of $1\times10^{-3}$ g/$m^2 \cdot 24$ h or less as determined in accordance with JIS K 7129-1992.

The sealing member may be formed into a concave plate by sandblasting or chemical etching.

Examples of the adhesive include photocurable and thermosetting adhesives containing reactive vinyl groups of acrylic acid oligomers and methacrylic acid oligomers, moisture-curable adhesives, such as 2-cyanoacrylate esters, and thermosetting and chemically curable adhesives (two-component adhesives), such as epoxy adhesives. Other examples include hot-melt polyamides, polyesters, and polyolefins, and cationic UV-curable epoxy resin adhesives.

In consideration that the organic EL element may be degraded through thermal treatment, an adhesive is preferably used which can be cured at a temperature of room temperature to 80° C. The adhesive may contain a desiccant dispersed therein. The adhesive may be applied to a sealing site with a commercially available dispenser or by screen printing.

An inorganic or organic layer (serving as a sealing film) is preferably formed on the electrode that sandwiches the organic layer with the supporting substrate so as to cover the electrode and the organic layer and to come into contact with the supporting substrate. The sealing film may be formed from any material capable of preventing intrusion of a substance that causes degradation of the organic EL element, such as moisture or oxygen. Examples of the material include silicon oxide, silicon dioxide, and silicon nitride.

In view of enhancement of the strength, the sealing film preferably has a layered structure composed of an inorganic layer and an organic material layer. The sealing film may be formed by any known process. Examples of the process include vacuum vapor deposition, sputtering, reactive sputtering, molecular beam epitaxy, ionized-cluster beam deposition, ion plating, plasma polymerization, atmospheric pressure plasma polymerization, plasma CVD, laser CVD, thermal CVD, and coating.

The gap between the sealing member and the display area of the organic EL element is preferably filled with an inert gas (e.g., nitrogen or argon) or an inert liquid (e.g., fluorohydrocarbon or silicone oil). The gap may be vacuum. Alternatively, the gap may be filled with a hygroscopic compound.

Examples of the hygroscopic compound include metal oxides (e.g., sodium oxide, potassium oxide, calcium oxide, barium oxide, magnesium oxide, and aluminum oxide), sulfates (e.g., sodium sulfate, calcium sulfate, magnesium sulfate, and cobalt sulfate), metal halides (e.g., calcium chloride, magnesium chloride, cesium fluoride, tantalum fluoride, cerium bromide, magnesium bromide, barium iodide, and magnesium iodide), and perchlorates (e.g., barium perchlorate and magnesium perchlorate). Preferred are anhydrous salts of sulfates, metal halides, and perchlorates.

[Protective Film, Protective Plate]

In order to increase the mechanical strength of the organic EL element, a protective film or plate may be provided on the outer surface of the sealing film that faces the supporting substrate with the organic layer being disposed therebetween. If the sealing film is used for sealing of the organic EL element, such a protective film or plate is preferably provided because the mechanical strength of the element is not necessarily high. Examples of the material for the protective film or plate include those used for the aforementioned sealing member, such as a glass plate, a composite of polymer plate and film, and a composite of metal plate and film. A polymer film is preferably used in view of a reduction in weight and thickness.

[Technique for Improvement of Light Extraction]

In a common organic EL element, light is emitted in the interior of a layer having a refractive index higher than that of air (i.e., a refractive index of about 1.6 to 2.1), and only about 15 to 20% of the light emitted in the layer is extracted to the outside. The reason for this is attributed to the following fact: light incident on an interface (interface between a transparent substrate and air) at an angle θ equal to or larger than the critical angle cannot be extracted from the element to the outside due to total reflection, or light is totally reflected at the interface between the transparent substrate and the transparent electrode or the luminous layer and is guided along the transparent electrode or the luminous layer, resulting in leakage of the light along the side face of the element.

Examples of the technique for improving the efficiency of light extraction include a technique for preventing total reflection at the interface between the transparent substrate and air by forming irregularities on the surface of the transparent substrate (refer to, for example, U.S. Pat. No. 4,774,435); a technique for improving the efficiency of light extraction by providing the substrate with light collecting properties (refer to, for example, Japanese Unexamined Patent Application Publication No. S63-314795); a technique for forming a reflective surface on the side faces of the element (refer to, for example, Japanese Unexamined Patent Application Publication No. H1-220394); a technique for providing an anti-reflective film by disposing a flat layer between the substrate and the luminous layer, the flat layer having a refractive index intermediate between those of the substrate and the luminous layer (refer to, for example, Japanese Unexamined Patent Application Publication No. S62-172691); a technique for disposing a flat layer between the substrate and the luminous layer, the flat layer having a refractive index lower than that of the substrate (refer to, for example, Japanese Unexamined Patent Application Publication No. 2001-202827); and a technique for providing a diffractive grating between any layers of the substrate, the transparent electrode layer, and the luminous layer (including the gap between the substrate and the outside of the element) (Japanese Unexamined Patent Application Publication No. H11-283751).

In the present invention, any of these techniques can be used for the organic EL element of the present invention. Preferred is a technique for disposing a flat layer between the substrate and the luminous layer, the flat layer having a refractive index lower than that of the substrate, or a technique for forming a diffractive grating between any layers of the substrate, the transparent electrode layer, and the luminous layer (including the gap between the substrate and the outside of the element).

The present invention can provide an organic EL element exhibiting higher luminance and superior durability by combination of the aforementioned techniques.

If a medium (layer) of low refractive index having a thickness larger than a light wavelength is provided between the transparent electrode and the transparent substrate, the efficiency of extraction of light from the transparent electrode to the outside increases with a decrease in refractive index of the medium.

The layer of low refractive index may be composed of, for example, aerogel, porous silica, magnesium fluoride, or a fluorine-containing polymer. The refractive index of the layer of low refractive index is preferably about 1.5 or less because the transparent substrate generally has a refractive index of about 1.5 to 1.7. The refractive index of the layer of low refractive index is more preferably 1.35 or less.

The medium of low refractive index preferably has a thickness twice or more the wavelength of light in the medium for the following reason. If the medium of low refractive index has a thickness nearly equal to the light wavelength, the electromagnetic wave exuding as an evanescent wave enters the substrate, leading to a reduction in the effects of the layer of low refractive index.

The technique for providing a diffractive grating at any interface where total reflection occurs or in any layer can highly improve the efficiency of light extraction. A diffractive grating directs light to a specific direction other than the refractive direction by Bragg diffraction (e.g., a primary diffraction or a secondary diffraction). This technique uses the diffractive grating disposed at any interface or in any layer (e.g., in the transparent substrate or the transparent electrode), and achieves extraction of a light component emitted from the luminous layer, which would otherwise fail to be extracted to the outside due to the total reflection, to the outside by diffraction with the diffractive grating.

The diffractive grating used preferably has a two-dimensional periodic refractive index profile, for the following reasons. Since light is emitted in any direction randomly in the luminous layer, a common one-dimensional diffractive grating having a periodic refractive index profile in a specific direction diffracts light only in the specific direction, resulting in a low effect of improving the efficiency of light extraction.

In contrast, the diffractive grating having a two-dimensional diffractive index profile can diffract light in any direction and thus highly improve the efficiency of light extraction.

The diffractive grating may be disposed at any interface or any layer (e.g., in the transparent substrate or the transparent electrode). Preferably, the diffractive grating is disposed adjacent to the organic luminous layer, which emits light. The pitch of the diffractive grating is preferably about a half to three times of the wavelength of light in the layer. The diffractive grating preferably has a two-dimensional repeated pattern, such as a square lattice, triangular lattice, or honeycomb lattice pattern.

[Light Condensing Sheet]

In the organic EL element of the present invention, a microlens array structure or a light condensing sheet may be disposed on the supporting substrate at the surface for light extraction, to collect light in a specific direction (e.g., in a front direction of the luminous face of the element), thereby increasing luminance in the specific direction.

For example, the microlens array includes two-dimensionally arranged quadrangular pyramids each having a 30-μm side and a vertex angle of 90°. Each side of the quadrangular pyramid has a length of preferably 10 to 100 μm. A side having a length below this range leads to coloring caused by diffraction, whereas an excessively long side leads to an undesirable increase in thickness of the element.

The light condensing sheet may be, for example, a commercially available sheet used in an LED backlight of a liquid crystal display device. Examples of such a sheet include Brightness Enhancement Film (BEF) (prism sheet) manufactured by Sumitomo 3M Ltd. The prism sheet may be composed of a substrate with triangular stripes having a vertex angle of 90° C. which are arranged at pitches of 50 μm. The vertexes of the triangular prisms may be rounded, or the pitches may be randomly varied. The prism sheet may have any other structure.

In order to control the radiation angle of light from the organic EL element, the light condensing sheet may be used in combination with a light diffusing plate or film; for example, a diffusing film (LIGHT-UP, manufactured by KIMOTO Co., Ltd.).

[Applications]

The organic EL element of the present invention may be used for electronic devices, such as display devices and various light sources.

Examples of light sources include, but are not limited to, lighting devices (e.g., household and in-vehicle lighting devices), backlight units of clocks and liquid crystal displays, billboards, traffic signals, light sources for optical storage media, light sources for electrophotocopiers, light sources for optical communication processors, and light sources for optical sensors. In particular, the organic EL element can be effectively used for a backlight unit of a liquid crystal display device and a light source for illumination.

In the organic EL element of the present invention, the layers may optionally be patterned with a metal mask or by ink jet printing during formation of the layers. The patterning process may be performed on only the electrodes, both the electrodes and the luminous layer, or all the layers of the element. Any known process may be used for preparation of the element.

<Display Device>

The display device of the present invention includes the organic EL element of the present invention. The display device of the present invention may be a monochromatic or multicolor display device. Now will be described a multicolor display device.

In the case of a multicolor display device, a shadow mask is provided only during formation of the luminous layer, and each of the other layers may be formed over the entire surface by, for example, vacuum vapor deposition, casting, spin coating, ink jetting, or printing.

Any process can be used for patterning of only the luminous layer. The patterning is preferably performed by vacuum vapor deposition, ink jetting, spin coating, or printing.

The configuration of the organic EL element of the display device is optionally selected from the above-exemplified configurations.

The process of producing the organic EL element of the present invention is as described above in one embodiment.

Application of a DC voltage of about 2 to 40V (anode: positive electrode, cathode: negative electrode) to the resultant multicolor display device leads to emission of light. In contrast, application of a voltage with reverse polarity results in no current flow through the device and no emission of light. If an AC voltage is applied to the device, light is emitted only in the state where the anode is positive and the cathode is negative. The AC voltage to be applied may have any waveform.

The multicolor display device can be used for various display devices or light sources. In the display device, full-color display is achieved with three types of organic EL elements; i.e., blue, red, and green light-emitting elements.

Examples of the display device include television sets, personal computers, mobile devices, AV devices, teletext displays, and information displays in automobiles. In particular, the display device may be used for reproducing still images or moving images. The driving system used in the display device for reproducing moving images may be a simple matrix (passive matrix) type or an active matrix type.

Examples of the light source include, but are not limited to, household lighting devices, in-vehicle lighting devices, backlight units of clocks and liquid crystal displays, billboards, traffic signals, light sources for optical storage media, light sources for electrophotocopiers, light sources for optical communication processors, and light sources for optical sensors.

Now will be described an example of the display device including the organic EL element of the present invention with reference to the drawings.

Figure 7:
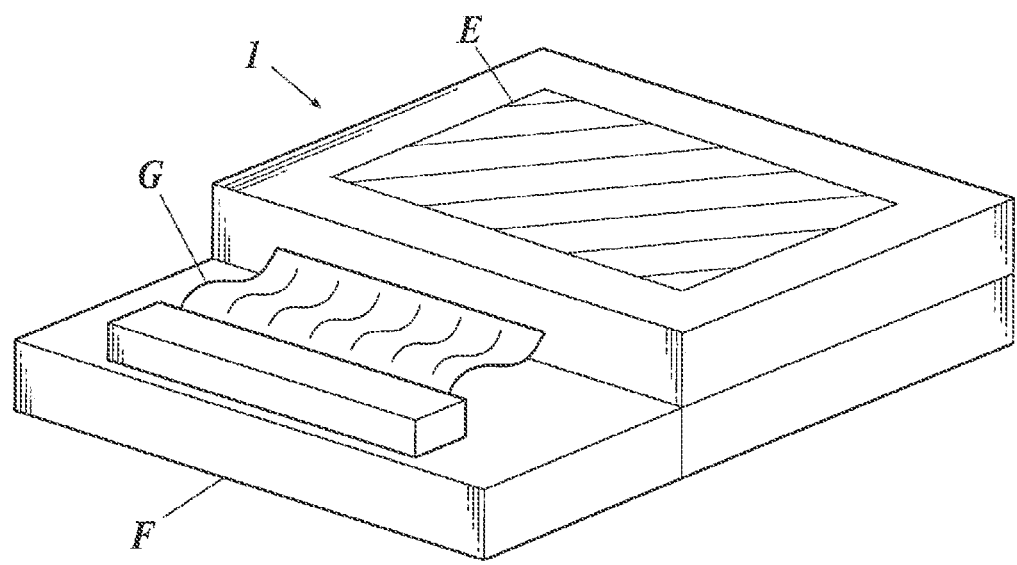
FIG. 7 is a schematic illustration of a display apparatus including an organic EL device.

FIG. 7 is a schematic illustration of an exemplary display device including the organic EL element. FIG. 7 schematically illustrates a display for, for example, a mobile phone to display image information through emission of light by the organic EL element.

A display 1 includes a display unit A having a plurality of pixels, a control unit B for image scanning on the display unit A on the basis of image information, and a wiring unit C that electrically connects the display unit A and the control unit B.

The control unit B, which is electrically connected to the display unit A via the wiring unit C, transmits scanning signals and image data signals to the individual pixels on the basis of external image information. The pixels in each scanning line sequentially emit light in response to the scanning signal on the basis of the image data signal, and the image information is displayed on the display unit A through image scanning.

Figure 8:
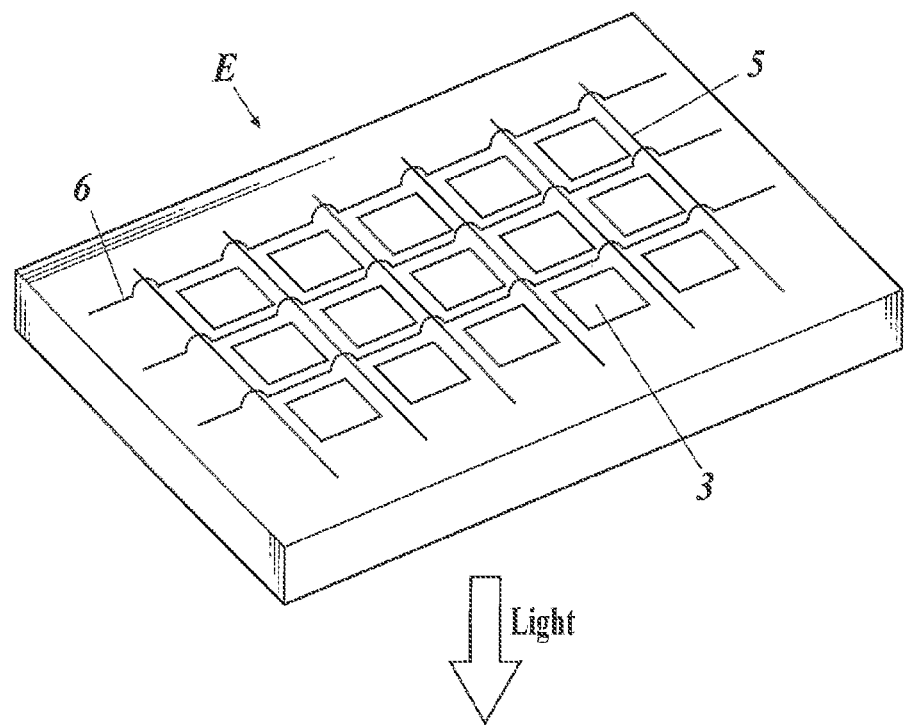
FIG. 8 is a schematic illustration of an active matrix display apparatus.

FIG. 8 is a schematic illustration of an active matrix display device.

A display unit A has, on a substrate, a wiring unit C including a plurality of scanning lines 5 and data lines 6, and a plurality of pixels 3. The main components of the display unit A will be described below.

With reference to FIG. 8, light emitted from the pixels 3 is extracted to the direction shown by the white arrow (downward direction).

The scanning lines 5 and the data lines 6 of the wiring unit are composed of a conductive material and are orthogonal to each other to form a grid pattern. The scanning lines 5 and the data lines 6 are connected to the pixels 3 at orthogonal intersections (details are not illustrated).

When a scanning signal is applied to the scanning lines 5, the pixels 3 receive an image data signal from the data lines 6 and emit light in response to the received image data.

Full-color display is achieved by appropriate arrangement of red, green, and blue light-emitting pixels on a single substrate.

Figure 9:
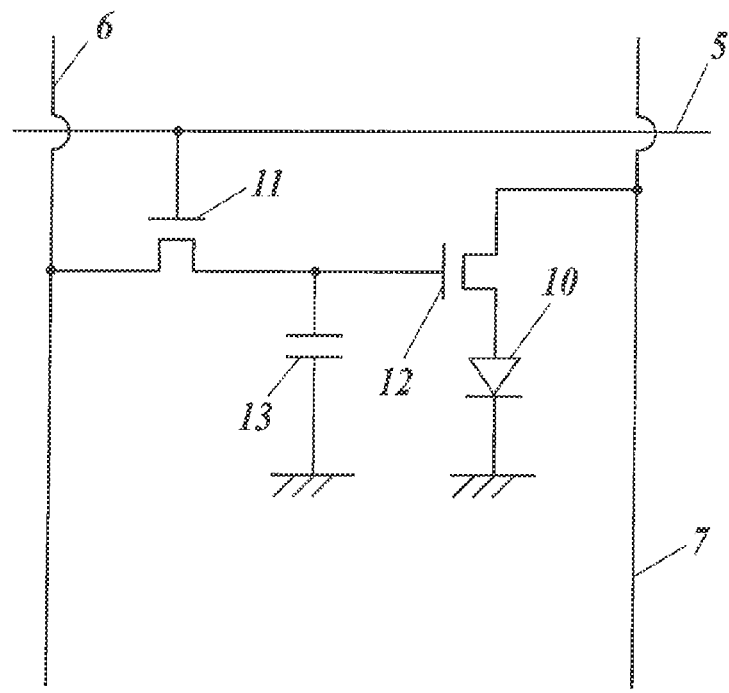
FIG. 9 is a schematic illustration of a pixel circuit.

Now will be described the emission process of a pixel. FIG. 9 is a schematic illustration of a pixel circuit.

The pixel includes an organic EL element 10, a switching transistor 11, a driving transistor 12, and a capacitor 13. Full color display is achieved by using a plurality of pixels arranged on a single substrate, each of the pixels including red, green, and blue light-emitting organic EL elements 10.

With reference to FIG. 9, an image data signal from the control unit B is applied to the drain of the switching transistor 11 via the data line 6. When a scanning signal from the control unit B is applied to the gate of the switching transistor 11 via the scanning line 5, the switching transistor 11 is turned on, and the image data signal applied to the drain is transmitted to the gates of the capacitor 13 and the driving transistor 12.

The capacitor 13 is charged through transmission of the image data signal depending on the potential of the image data signal, and the driving transistor 12 is turned on. The drain and source of the driving transistor 12 are connected to a power source line 7 and the electrode of the organic EL element 10, respectively. Depending on the potential of the image data signal applied to the gate, a current is supplied from the power source line 7 to the organic EL element 10.

When the scanning signal is transmitted to the next scanning line 5 through sequential scanning by the control unit B, the switching transistor 11 is turned off. Since the capacitor 13 maintains the charged potential corresponding to the image data signal even after turning off of the switching transistor 11, the driving transistor 12 is maintained in an ON state, and the organic EL element 10 continues to emit light until application of the next scanning signal. Through application of the next scanning signal by sequential scanning, the driving transistor 12 is driven depending on the potential of the subsequent image data signal in synchronization with the scanning signal, and the organic EL element 10 emits light.

In each of the pixels 3, the organic EL element 10 emits light through driving of the switching transistor 11 and the driving transistor 12 serving as active elements. This light-emitting system is called "active matrix type."

Multi-tone light may be emitted from the organic EL element 10 in response to multivalued image data signals having different gradient potentials. Alternatively, light with a specific intensity from the organic EL element 10 may be turned on or off in response to a binary image data signal. The potential of the capacitor 13 may be maintained until application of the subsequent scanning signal, or the capacitor 13 may be discharged immediately before application of the subsequent scanning signal.

In the present invention, the display device may be not only of the aforementioned active matrix type, but also of a passive matrix type, in which light is emitted from the organic EL element in response to the data signal only during application of the scanning signals.

Figure 10:
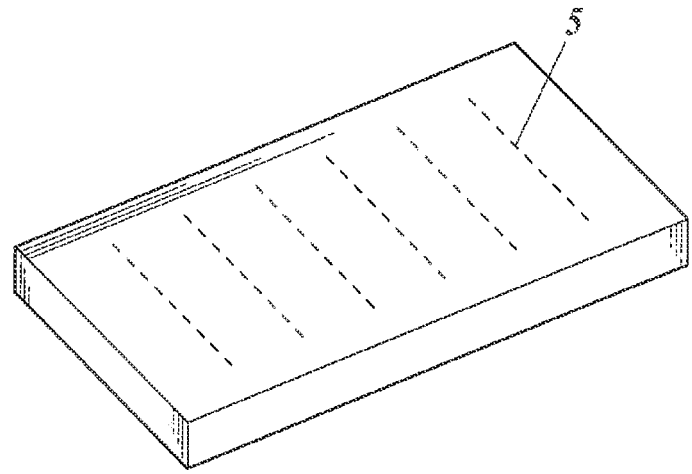
FIG. 10 is a schematic illustration of a passive matrix display apparatus.
Figure 10:
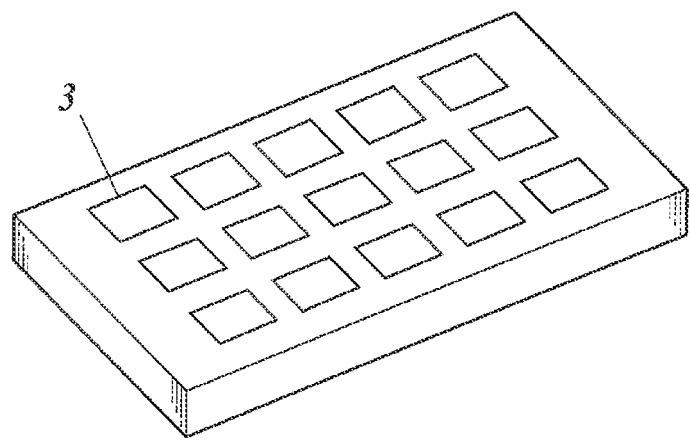
Figure 10:
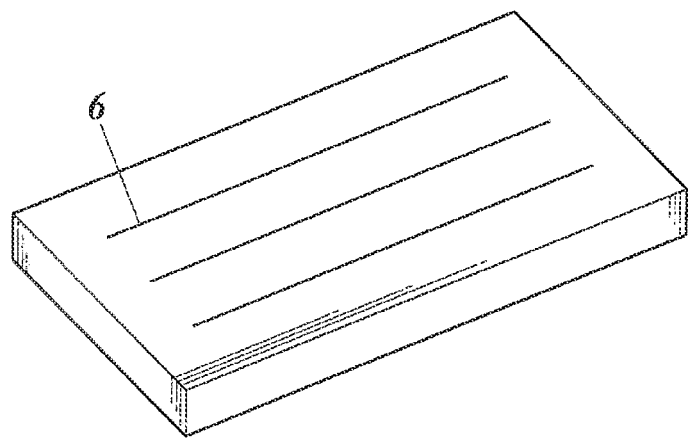

FIG. 10 is a schematic illustration of a passive matrix display device. With reference to FIG. 10, pixels 3 are disposed between a plurality of scanning lines 5 and a plurality of image data lines 6 to form a grid pattern.

When a scanning signal is applied to a scanning line 5 through sequential scanning, the pixel 3 connected to the scanning line 5 emits light in response to the image data signal.

The passive matrix display device can reduce production cost because of no active element in each pixel 3.

The use of the organic EL element of the present invention achieves a display device exhibiting improved emission efficiency.

<Lighting Device>

The organic EL element of the present invention can also be used for a lighting device.

The organic EL element of the present invention may have a resonator structure. Examples of the application of the organic EL element having a resonator structure include, but are not limited to, light sources for optical storage media, light sources for electrophotocopiers, light sources for optical communication processors, and light sources for optical sensors. Alternatively, the organic EL element of the present invention may be used for the aforementioned purposes by laser oscillation.

The organic EL element of the present invention may be used in a lamp, such as a lighting source or an exposure light source, or may be used in a projector for projecting images or a display device for directly viewing still or moving images.

If the organic EL element is used in a display device for playback of moving images, the display device may be of a passive matrix type or an active matrix type. A full-color display device can be produced from two or more organic EL elements of the present invention that emit light of different colors.

The fluorescent compound used in the present invention can be applied to a lighting device including an organic EL element that emits substantially white light. White light is produced by mixing light of different colors simultaneously emitted from a plurality of luminous materials. The combination of emitted light of different colors may include light of three primary colors (red, green, and blue) with three maximum emission wavelengths, or light of complementary colors (e.g., blue and yellow or blue-green and orange) with two maximum emission wavelengths.

For preparation of the organic EL element of the present invention, a mask is disposed only during formation of the luminous layer, the hole transporting layer, or the electron transporting layer such that a patterning process is performed simply through the mask. The other layers, which have a common structure, do not require any patterning process with a mask. Thus, an electrode film can be formed on the entire surface of such a layer through, for example, vacuum vapor deposition, casting, spin coating, ink jetting, or printing, resulting in improved productivity.

The element produced by this process emits white light, unlike a white light-emitting organic EL device including arrayed luminous elements that emit light of a plurality of colors.

[Embodiment of Lighting Device of the Present Invention]

Now will be described an embodiment of the lighting device including the organic EL element of the present invention.

The non-luminous surface of the organic EL element of the present invention is covered with a glass casing, and a glass substrate having a thickness of 300 μm is used as a sealing substrate. A photocurable epoxy adhesive (LUX-TRACK LC0629B, manufactured by TOAGOSEI CO., LTD.), serving as a sealing material, is applied to the periphery of the substrate, and the glass casing is placed on the cathode and is attached to the transparent supporting substrate, followed by curing of the adhesive by irradiation of the glass substrate with UV rays. A lighting device shown in FIG. 11 or 12 is thereby produced.

Figure 11:
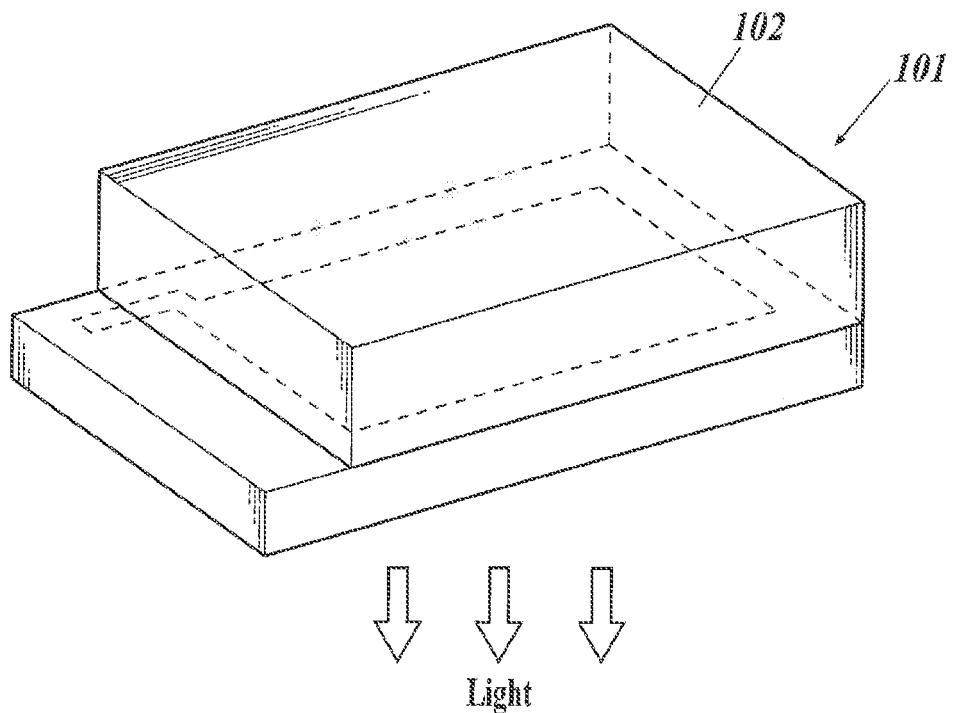
FIG. 11 is a schematic illustration of a lighting apparatus.

FIG. 11 is a schematic illustration of the lighting device. The organic EL element 101 (in the lighting device) of the present invention is covered with a glass casing 102 (sealing with the glass casing is performed in a glove box under a nitrogen atmosphere (an atmosphere of nitrogen gas having a purity of 99.999% or more) for preventing the organic EL element 101 from being exposed to air).

Figure 12:
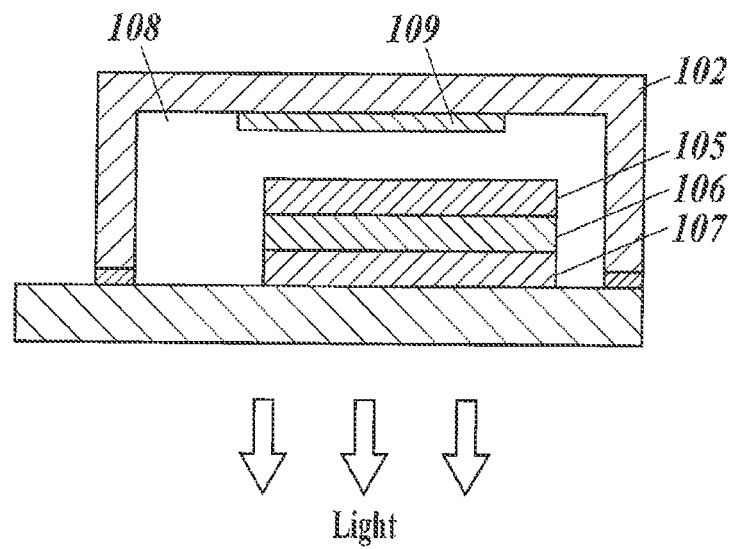
FIG. 12 is a cross-sectional view of the lighting apparatus.

FIG. 12 is a cross-sectional view of the lighting device. As illustrated in FIG. 12, the lighting device includes a cathode 105, an organic EL layer 106, and a glass substrate 107 having a transparent electrode. The interior of the glass casing 102 is filled with nitrogen gas 108 and is provided with a desiccant 109.

The use of the organic EL element of the present invention achieves a lighting device exhibiting improved emission efficiency.

<Luminous Material>

In the present invention, the luminous material contains at least one of π-conjugated compounds having structures represented by General formula (A).

This material leads to an improvement in electron mobility in the organic EL device, and prevention of a reduction in emission efficiency due to high current density in the organic EL device (i.e., an improvement in roll off properties), resulting in high emission efficiency and prolonged lifetime.

The luminous material preferably contains a host compound having a structure represented by General formula (I), General formula (II), and/or General formulae (III-1) to (III-3) besides the π-conjugated compound. This configuration leads to further improved emission efficiency and prolonged lifetime.

The π-conjugated compound used as a luminous material in the present invention can also be applied to a thin luminous film, a thin charge-transfer film, a display apparatus, and a lighting apparatus.

The thin luminous film of the present invention will now be described.

<Thin Luminous Film>

The thin luminous film of the present invention can be formed as in the organic layer described above.

The thin luminous film of the present invention can be formed by any known process, such as a vacuum vapor deposition process or a wet process.

Examples of the wet process include spin coating, casting, ink jetting, printing, die coating, blade coating, roll coating, spray coating, curtain coating, and the Langmuir-Blodgett (LB) method. Preferred are processes highly suitable for a roll-to-roll system, such as die coating, roll coating, ink jetting, and spray coating, in view of easy formation of a thin homogeneous film and high productivity.

Examples of the liquid medium for dissolution or dispersion of the luminous material used in the present invention include ketones, such as methyl ethyl ketone and cyclohexanone; fatty acid esters, such as ethyl acetate; halogenated hydrocarbons, such as dichlorobenzene; aromatic hydrocarbons, such as toluene, xylene, mesitylene, and cyclohexylbenzene; aliphatic hydrocarbons, such as cyclohexane, decalin, and dodecane; and organic solvents, such as DMF and DMSO.

Examples of the usable dispersion technique include ultrasonic dispersion, high shearing force dispersion, and media dispersion.

Individual layers may be formed through different processes. Conditions of a vapor evaporation process for formation of a layer may vary depending on the type of a compound used. In general, the process is performed under the following conditions: a boat heating temperature of 50 to 450° C., a vacuum of $10^{-6}$ to $10^{-2}$ Pa, a deposition rate of 0.01 to 50 nm/second, a substrate temperature of −50 to 300° C., and a layer thickness of 0.1 nm to 5 μm (preferably 5 to 200 nm).

In the case of spin coating for formation of a layer, the process is preferably performed in a dry inert gas atmosphere under the following conditions: a spin coater rotation rate of 100 to 1,000 rpm and a coating period of 10 to 120 seconds.

The thin luminous film of the present invention can be applied to a display or lighting apparatus.

The resultant display or lighting apparatus exhibits improved emission efficiency.

EXAMPLES

The present invention will now be described in detail by way of Examples, which should not be construed to limit the invention. Unless otherwise specified, the terms "part(s)" and "%" in the following description indicate "part(s) by mass" and "mass %," respectively.

In the Examples, the vol % of a compound is determined on the basis of the thickness of a layer composed of the compound measured by a quartz crystal microbalance technique, the calculated mass of the layer, and the specific weight of the compound.

The structures of compounds used in Examples and Comparative Examples are described below.

[Chem 73]

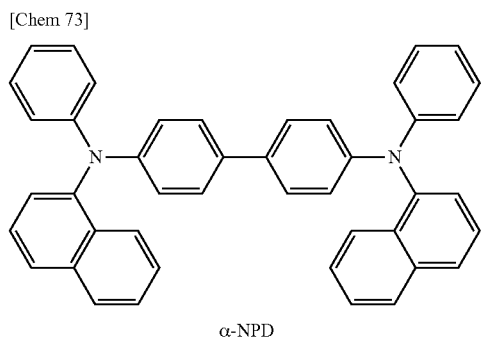

α-NPD

157
-continued
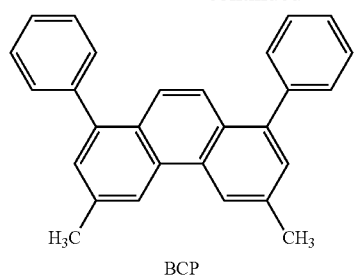
BCP
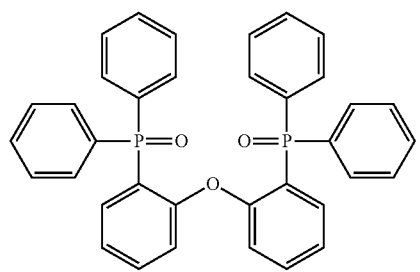
DPEPO
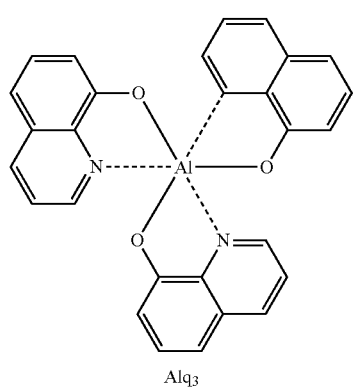
Alq₃
[Chem 74]
Comparative compound 1
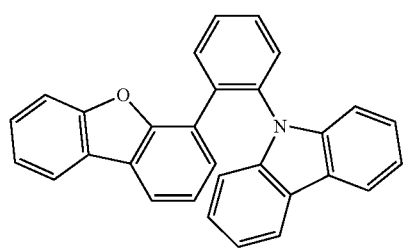
Comparative compound 2
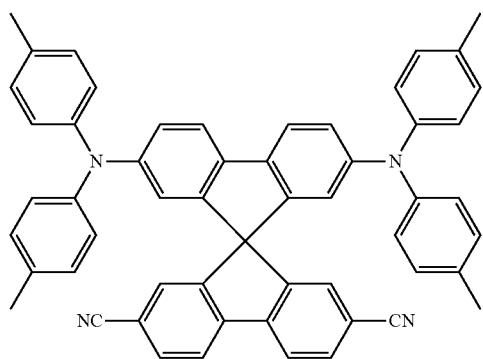
158
-continued
Comparative compound 3
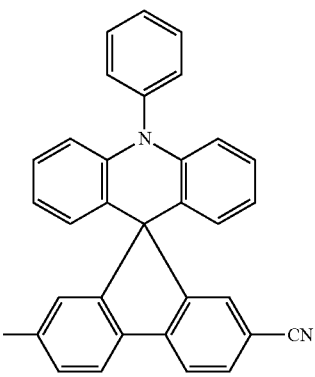
Comparative compound 4
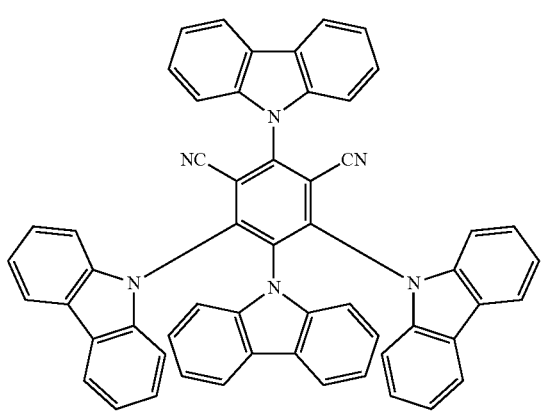
Comparative compound 5
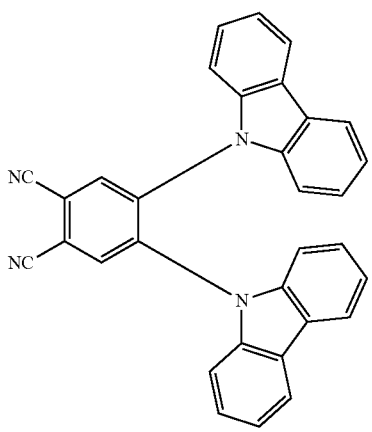

-continued

Comparative compound 6

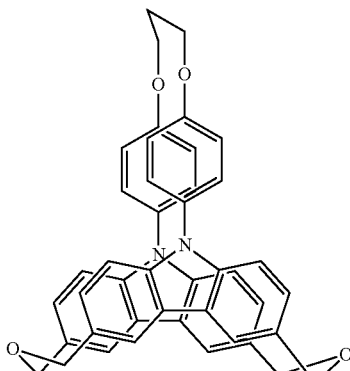

Comparative compound 11

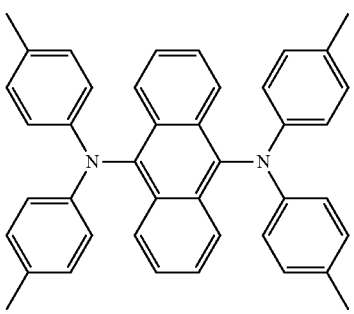

Comparative compound 12

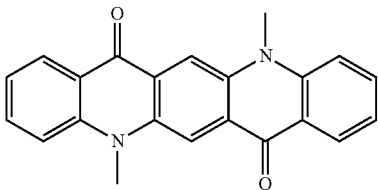

Comparative compound 13

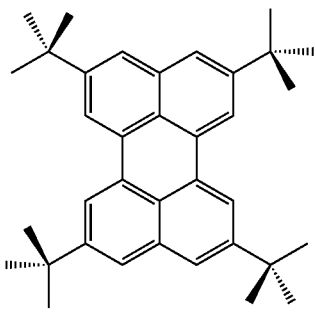

Example 1

(Preparation of Organic EL Device 1-1)

An indium tin oxide (ITO) anode having a thickness of 150 nm was formed on a glass substrate (50 mm by 50 mm, thickness: 0.7 mm), followed by patterning. The transparent substrate provided with the transparent ITO electrode was ultrasonically cleaned in isopropyl alcohol, dried with dry nitrogen gas, and then subjected to UV ozone cleaning for five minutes. The resultant transparent substrate was fixed to a substrate holder of a commercially available vacuum vapor deposition apparatus.

Materials for layers were placed in vapor deposition crucibles in the vacuum vapor deposition apparatus in amounts suitable for preparation of an organic EL device. The crucibles were composed of molybdenum or tungsten; i.e., a material for resistance heating.

The apparatus was evacuated to a vacuum of $1 \times 10^{-4}$ Pa, and a vapor deposition crucible containing α-NPD was heated by energization. α-NPD was vapor-deposited onto the ITO transparent electrode at a deposition rate of 0.1 nm/second, to form a hole transporting layer having a thickness of 40 nm.

Subsequently, H-46 (host compound) and comparative compound 1 (dopant) were co-deposited onto the hole transporting layer at a deposition rate of 0.1 nm/second, to form a luminous layer having a thickness of 35 nm and containing 94 vol % H-46 and 6 vol % comparative compound 1.

BCP (electron transporting material) was then vapor-deposited onto the luminous layer at a deposition rate of 0.1 nm/second, to form an electron transporting layer having a thickness of 30 nm.

A lithium fluoride layer having a thickness of 0.5 nm was then formed on the electron transporting layer, and aluminum was vapor-deposited onto the lithium fluoride layer, to form a cathode having a thickness of 100 nm.

The non-luminous surface of the device was covered with a cylindrical glass casing in an atmosphere of nitrogen gas having a purity of 99.999% or more, and lead wires for the electrodes were provided, to prepare an organic EL device 1-1.

(Preparation of Organic EL Devices 1-2 to 1-12)

Organic EL devices 1-2 to 1-12 were prepared as in organic EL device 1-1, except that the dopant was varied as shown in Table 1.

(Evaluation)

Organic EL devices 1-1 to 1-12 were evaluated as described below.

(Evaluation of External Quantum Efficiency (Luminance) EQE)

Each of the prepared organic EL devices was driven at room temperature (about 25° C.) and a constant current of 2.5 mA/cm², and a luminance immediately after the initiation of emission was measured with a spectroradiometer CS-2000 (manufactured by Konica Minolta, Inc.).

Subsequently, the relative luminance of the organic EL device was determined on the basis of the luminance (taken as 100) of organic EL device 1-1 (Comparative Example). The determined relative luminance was used as an indicator of emission efficiency (external quantum efficiency). A larger relative luminance indicates a higher emission efficiency.

(Increase in Voltage During Driving)

An increase in voltage of each organic EL device (sample) during driving was determined as described below.

(A) Measurement of Initial Driving Voltage

The luminance of each sample was measured at room temperature (about 25° C.) with a spectroradiometer CS-2000 (manufactured by Konica Minolta, Inc.), and the initial driving voltage at a luminance of 1,000 cd/m² was determined.

(B) Measurement of Voltage after Evaluation of Half-Life

The luminance of each sample was measured at room temperature (about 25° C.) with a spectroradiometer CS-2000 (manufactured by Konica Minolta, Inc.) after evaluation of half-life, and the driving voltage at a luminance of 1,000 cd/m² was determined. The half-life was evaluated as described below.

(Increase in Voltage During Driving)

Driving voltage was determined by the following expression:

increase in voltage=(($B$)driving voltage at a luminance of 1,000 cd/m$^2$ after half-life)/(($A$)initial driving voltage at a luminance of 1,000 cd/m$^2$).

As illustrated in Table 1, a smaller increase in voltage indicates a better performance.

TABLE 1

| Organic EL device | Dopant | Host compound | External quantum efficiency (Relative value) | Increase in voltage during driving | Remarks |
|---|---|---|---|---|---|
| 1-1 | Comparative compound 1 | H-46 | 100 | 2.0 | Comparative Example |
| 1-2 | Comparative compound 2 | H-46 | 50 | 2.3 | Comparative Example |
| 1-3 | Comparative compound 3 | H-46 | 55 | 2.2 | Comparative Example |
| 1-4 | Comparative compound 5 | H-46 | 110 | 2.4 | Comparative Example |
| 1-5 | Comparative compound 6 | H-46 | 98 | 2.3 | Comparative Example |
| 1-6 | Exemplary compound 36 | H-46 | 128 | 1.4 | Present invention |
| 1-7 | Exemplary compound 46 | H-46 | 125 | 1.6 | Present invention |
| 1-8 | Exemplary compound 57 | H-46 | 124 | 1.6 | Present invention |
| 1-9 | Exemplary compound 63 | H-46 | 128 | 1.6 | Present invention |
| 1-10 | Exemplary compound 50 | H-46 | 129 | 1.5 | Present invention |
| 1-11 | Exemplary compound 78 | H-46 | 133 | 1.4 | Present invention |
| 1-12 | Exemplary compound 90 | H-46 | 131 | 1.5 | Present invention |

(Results)

Organic EL devices 1-6 to 1-12, each containing the fluorescent compound according to the present invention as a dopant, exhibits improved external quantum efficiency (EQE) and reduced driving voltage.

Example 2

(Preparation of Organic EL Device 2-1)

An indium tin oxide (ITO) anode having a thickness of 150 nm was formed on a glass substrate (50 mm by 50 mm, thickness: 0.7 mm), followed by patterning. The transparent substrate provided with the transparent ITO electrode was ultrasonically cleaned in isopropyl alcohol, dried with dry nitrogen gas, and then subjected to UV ozone cleaning for five minutes. The resultant transparent substrate was fixed to a substrate holder of a commercially available vacuum vapor deposition apparatus.

Materials for layers were placed in vapor deposition crucibles in the vacuum vapor deposition apparatus in amounts suitable for preparation of an organic EL device. The crucibles were composed of molybdenum or tungsten; i.e., a material for resistance heating.

The apparatus was evacuated to a vacuum of $1 \times 10^{-4}$ Pa, and a vapor deposition crucible containing α-NPD was heated by energization. α-NPD was vapor-deposited onto the ITO transparent electrode at a deposition rate of 0.1 nm/second, to form a hole transporting layer having a thickness of 40 nm.

Subsequently, H-46 (host compound) and comparative compound 1 (dopant) were co-deposited onto the hole transporting layer at a deposition rate of 0.1 nm/second, to form a luminous layer having a thickness of 35 nm and containing 90 vol % H-46 and 10 vol % comparative compound 1.

DPEPO was then vapor-deposited onto the luminous layer at a deposition rate of 0.1 nm/second, to form a hole blocking layer having a thickness of 10 nm. Alq$_3$ (electron transporting material) was then vapor-deposited onto the hole blocking layer at a deposition rate of 0.1 nm/second, to form a hole transporting layer having a thickness of 30 nm.

A lithium fluoride layer having a thickness of 0.5 nm was then formed on the hole transporting layer, and aluminum was vapor-deposited onto the lithium fluoride layer, to form a cathode having a thickness of 100 nm.

The non-luminous surface of the device was covered with a cylindrical glass casing in an atmosphere of nitrogen gas having a purity of 99.999% or more, and lead wires for the electrodes were provided, to prepare an organic EL device 2-1.

(Preparation of Organic EL Devices 2-2 to 2-13)

Organic EL devices 2-2 to 2-13 were prepared as in organic EL device 2-1, except that the dopant and the host compound were varied as shown in Table 2.

(Evaluation)

Organic EL devices 2-1 to 2-13 were evaluated as described below.

(Evaluation of External Quantum Efficiency (Luminance))

Each of the prepared organic EL devices was driven at room temperature (about 25° C.) and a constant current of 2.5 mA/cm$^2$, and a luminance immediately after the initiation of emission was measured with a spectroradiometer CS-2000 (manufactured by Konica Minolta, Inc.).

Subsequently, the relative luminance of the organic EL device was determined on the basis of the luminance (taken as 100) of organic EL device 2-1 (Comparative Example). The determined relative luminance was used as an indicator of emission efficiency (external quantum efficiency). A larger relative luminance indicates a higher emission efficiency.

(Evaluation of Half-Life (Continuous Driving Stability))

While each sample was continuously driven at an initial luminance of 3,000 cd/m$^2$, the luminance of the sample was measured with a spectroradiometer CS-2000, to determine a half-life of luminance (LT50).

The relative LT50 of each organic EL device was determined on the basis of the LT50 (taken as 100) of organic EL element 2-1 (Comparative Example). The determined relative value was used as an indicator of continuous driving stability. Table 2 illustrates the results of evaluation. In Table 2, a larger relative value indicates a higher continuous driving stability (longer lifetime).

TABLE 2

| Organic EL device | Dopant | Host compound | External quantum efficiency (Relative value) | Half-life (Relative value) | Remarks |
|---|---|---|---|---|---|
| 2-1 | Comparative compound 1 | H-46 | 100 | 100 | Comparative Example |
| 2-2 | Comparative compound 2 | H-159 | 46 | 80 | Comparative Example |

TABLE 2-continued

| Organic EL device | Dopant | Host compound | External quantum efficiency (Relative value) | Half-life (Relative value) | Remarks |
|---|---|---|---|---|---|
| 2-3 | Comparative compound 3 | H-46 | 38 | 65 | Comparative Example |
| 2-4 | Comparative compound 4 | H-46 | 105 | 115 | Comparative Example |
| 2-5 | Comparative compound 6 | H-159 | 95 | 112 | Comparative Example |
| 2-6 | Exemplary compound 35 | H-46 | 120 | 146 | Present invention |
| 2-7 | Exemplary compound 46 | H-115 | 122 | 155 | Present invention |
| 2-8 | Exemplary compound 48 | H-46 | 124 | 148 | Present invention |
| 2-9 | Exemplary compound 50 | H-159 | 122 | 155 | Present invention |
| 2-10 | Exemplary compound 57 | H-46 | 130 | 165 | Present invention |
| 2-11 | Exemplary compound 84 | H-60 | 120 | 130 | Present invention |
| 2-12 | Exemplary compound 90 | H-46 | 124 | 170 | Present invention |
| 2-13 | Exemplary compound 99 | H-46 | 122 | 168 | Present invention |

(Results)

The results demonstrate that organic EL devices 2-6 to 2-13, each containing the π-conjugated compound according to the present invention, exhibit higher external quantum efficiency and half-life than comparative organic EL devices.

Example 3

Red light-emitting organic EL device 2-10, green light-emitting organic EL device 2-4, and blue light-emitting organic EL device 2-7, which were prepared in Example 2, were arranged on a single substrate, to prepare an active matrix full-color display apparatus illustrated in FIG. 8. FIG. 8 is a schematic illustration of display A of the full-color display apparatus. In detail, the display has, on a single substrate, a wiring unit including a plurality of scanning lines 5 and data lines 6, and a plurality of arranged pixels 3 (red light-emitting, green light-emitting, and blue light-emitting pixels). The scanning lines 5 and data lines 6 of the wiring unit are composed of a conductive material and are orthogonal to each other to form a grid pattern. The scanning lines 5 and the data lines 6 are connected to the pixels 3 at orthogonal intersections (details are not illustrated). The pixels 3 are driven by the active matrix system including the organic EL devices that emit light of different colors, and a switching transistor and a driving transistor serving as active devices. If a scanning signal is applied to the scanning lines 5, the pixels 3 receive an image data signal from the data lines 6 and emit light in response to the received image data. Thus, full-color display is achieved by appropriate arrangement of red light-emitting, green light-emitting, and blue light-emitting pixels on the substrate. In Example 3, the full-color display apparatus was driven to display a clear full-color moving image of high luminance.

Example 4

Table 3 illustrates the HOMO and LUMO electron densities of moieties L, $\theta_{DA}$, distance r between orbital centroids, probability of electron transition, and ΔEst of π-conjugated compounds according to the present invention, and those of comparative compounds.

ΔEst was calculated by the following expression: ΔEst=E(S$_1$)−E(T$_1$) where E(S$_1$) and E(T$_1$) are respectively the excited energy levels S$_1$ and T$_1$, which are calculated through the time-dependent density functional theory (time-dependent DFT) on the basis of the structural optimization determined using B3LYP (functional) and 6-31G(d) (basis function).

TABLE 3

| π-conjugated compound | HUMO electron density of L (%) | LUMO electron density of L (%) | $\theta_{DA}$ (°) | Distance between the centroids of orbitals r (nm) | Probability of electron transition (%) | ΔEst (eV) |
|---|---|---|---|---|---|---|
| Comparative compound 1 | 0 | 15 | 54 | 0.57 | 49 | 0.52 |
| Comparative compound 2 | 0 | 2 | 180 | 0.34 | 99 | 0.01 |
| Comparative compound 3 | 0 | 1 | 180 | 0.34 | 99 | 0.01 |
| Comparative compound 4 | 0 | 14 | 120 | 0.56 | 98 | 0.12 |
| Comparative compound 5 | 11 | 67 | 120 | 0.56 | 99 | 0.34 |
| Comparative compound 6 | — | — | — | — | 97 | 0.15 |
| Exemplary compound 35 | 9 | 4 | 63 | 0.43 | 99 | 0.39 |
| Exemplary compound 36 | 3 | 2 | 67 | 0.52 | 99 | 0.48 |
| Exemplary compound 46 | 3 | 3 | 66 | 0.46 | 99 | 0.01 |
| Exemplary compound 48 | 2 | 2 | 58 | 0.59 | 98 | 0.08 |

TABLE 3-continued

| π-conjugated compound | HOMO electron density of L (%) | LUMO electron density of L (%) | $\theta_{DA}$ (°) | Distance between the centroids of orbitals r (nm) | Probability of electron transition (%) | ΔEst (eV) |
|---|---|---|---|---|---|---|
| Exemplary compound 50 | 5 | 0 | 19 | 0.38 | 98 | 0.24 |
| Exemplary compound 57 | 6 | 6 | 17 | 0.34 | 97 | 0.17 |
| Exemplary compound 63 | 5 | 0 | 83 | 0.59 | 99 | 0.03 |
| Exemplary compound 68 | 7 | 8 | 47 | 0.37 | 99 | 0.52 |
| Exemplary compound 78 | 4 | 1 | 71 | 0.48 | 95 | 0.07 |
| Exemplary compound 84 | 2 | 0 | 17 | 0.38 | 99 | 0.52 |
| Exemplary compound 90 | 6 | 4 | 28 | 0.46 | 96 | 0.44 |
| Exemplary compound 99 | 4 | 2 | 42 | 0.48 | 98 | 0.39 |

As illustrated in Table 3, the π-conjugated compounds according to the present invention exhibit ΔEst equal to or lower than that of the comparative compounds, and satisfy the requirements for electron transition between the HOMO and the LUMO by a through-space interaction; i.e., a HOMO electron density of moiety L of less than 10%, a LUMO electron density of moiety L of less than 10%, an angle $\theta_{DA}$ of less than 90°, a distance r between orbital centroids of 0.6 nm or less, and a probability of electron transition of 90% or more.

Example 5

(Preparation of Organic EL Device 3-1)

An indium tin oxide (ITO) anode having a thickness of 150 nm was formed on a glass substrate (50 mm by 50 mm, thickness: 0.7 mm), followed by patterning. The transparent substrate provided with the transparent ITO electrode was ultrasonically cleaned in isopropyl alcohol, dried with dry nitrogen gas, and then subjected to UV ozone cleaning for five minutes. The resultant transparent substrate was fixed to a substrate holder of a commercially available vacuum vapor deposition apparatus.

Materials for layers were placed in vapor deposition crucibles in the vacuum vapor deposition apparatus in amounts suitable for preparation of an organic EL device. The crucibles were composed of molybdenum or tungsten; i.e., a material for resistance heating.

The apparatus was evacuated to a vacuum of $1 \times 10^{-4}$ Pa, and a vapor deposition crucible containing α-NPD was heated by energization. α-NPD was vapor-deposited onto the ITO transparent electrode at a deposition rate of 0.1 nm/second, to form a hole transporting layer having a thickness of 40 nm.

Subsequently, H-46 (host compound) and comparative compound 1 were co-deposited onto the hole transporting layer at a deposition rate of 0.1 nm/second, to form a luminous layer having a thickness of 35 nm and containing 93 vol % H-46 and 7 vol % comparative compound 1.

Compound H-42 was then vapor-deposited onto the luminous layer at a deposition rate of 0.1 nm/second, to form a hole blocking layer (also serving as an electron transporting layer) having a thickness of 30 nm.

A lithium fluoride layer having a thickness of 0.5 nm was then formed on the hole blocking layer, and aluminum was vapor-deposited onto the lithium fluoride layer, to form a cathode having a thickness of 100 nm.

The non-luminous surface of the device was covered with a cylindrical glass casing in an atmosphere of nitrogen gas having a purity of 99.999% or more, and lead wires for the electrodes were provided, to prepare an organic EL device 3-1.

(Preparation of Organic EL Devices 3-2 to 3-7)

Organic EL devices 3-2 to 3-7 were prepared as in organic EL device 3-1, except that the host, dopant, and assist dopant compounds were varied as shown in Table 4.

(Evaluation of Organic EL Devices 3-1 to 3-7) (Evaluation)

Organic EL devices 3-1 to 3-7 were evaluated as described below.

(Evaluation of External Quantum Efficiency (Luminance))

Each of the prepared organic EL devices was driven at room temperature (about 25° C.) and a constant current of 2.5 mA/cm², and a luminance immediately after the initiation of emission was measured with a spectroradiometer CS-2000 (manufactured by Konica Minolta, Inc.).

Subsequently, the relative luminance of the organic EL device was determined on the basis of the luminance (taken as 100) of organic EL device 3-1 (Comparative Example). The determined relative luminance was used as an indicator of emission efficiency (external quantum efficiency). A larger relative luminance indicates a higher emission efficiency.

(Evaluation of Half-Life (Continuous Driving Stability))

While each sample was continuously driven at an initial luminance of 3,000 cd/m², the luminance of the sample was measured with a spectroradiometer CS-2000, to determine a half-life of luminance (LT50).

The relative LT50 of each organic EL device was determined on the basis of the LT50 (taken as 100) of organic EL element 3-1 (Comparative Example). The determined relative value was used as an indicator of continuous driving stability. Table 4 illustrates the results of evaluation. In Table 4, a larger relative value indicates a higher continuous driving stability (longer lifetime).

TABLE 4

| Organic EL device | π-conjugated compound (a) | Host compound (b) | Fluorescent compound (c) | Doping ratio (Volume ratio = (a)/(b)/(c)) | External quantum efficiency (Relative value) | Half-life (Relative value) | Remarks |
|---|---|---|---|---|---|---|---|
| 3-1 | — | H-46 | Comparative compound 11 | 0/93/7 | 100 | 100 | Comparative Example |
| 3-2 | Comparative compound 13 | H-46 | Comparative compound 11 | 20/74/6 | 103 | 104 | Comparative Example |
| 3-3 | Comparative compound 13 | CBP | Comparative compound 12 | 30/60/10 | 102 | 110 | Comparative Example |
| 3-4 | Exemplary compound 46 | H-46 | Comparative compound 12 | 25/65/10 | 170 | 184 | Present invention |
| 3-5 | Exemplary compound 50 | DPEPO | Comparative compound 11 | 18/77/5 | 180 | 166 | Present invention |
| 3-6 | Exemplary compound 57 | H-46 | Comparative compound 12 | 20/72/8 | 174 | 175 | Present invention |
| 3-7 | Exemplary compound 90 | DPEPO | Comparative compound 11 | 22/70/8 | 195 | 160 | Present invention |

(Results)

The results demonstrate that organic EL devices 3-4 to 3-7 exhibit higher external quantum efficiency and half-life than comparative organic EL devices.

This is probably attributed to the fact that the π-conjugated compound according to the present invention assists the emission of another fluorescent compound. In detail, the fluorescent compound can efficiently receive energy from the π-conjugated compound according to the present invention (which exhibits a higher energy level than the fluorescent compound) during excitation of the π-conjugated compound in the organic EL device, resulting external quantum efficiency comparable to that in the case of emission of the π-conjugated compound according to the present invention.

INDUSTRIAL APPLICABILITY

As described above, the present invention provides an organic electroluminescent device exhibiting high emission efficiency and high stability (i.e., a slight variation in emission properties over time). The present invention also provides a thin luminous film containing a π-conjugated compound for use in the organic electroluminescent device. The present invention also provides a display apparatus and a lighting apparatus, each of the apparatuses including the organic electroluminescent device.

EXPLANATION OF REFERENCE NUMERALS

A: electron-accepting moiety
D: electron-donating moiety
L: linkage moiety
1: display
3: pixel
5: scanning line
6: data line
7: power source line
10: organic EL device
11: switching transistor
12: driving transistor
13: capacitor
101: organic EL device in lighting apparatus
102: glass casing
105: cathode
106: organic layer
107: glass substrate having transparent electrode
108: nitrogen gas
109: water-collecting agent
E: display unit
F: control unit
G: wiring unit

The invention claimed is:

1. An organic electroluminescent device comprising:
an anode;
a cathode; and
an organic layer comprising at least one luminous layer, the organic layer being disposed between the anode and the cathode, wherein
at least one of the at least one luminous layer comprises a π-conjugated compound exhibiting no overlap between the electron density distributions of the HOMO and the LUMO in the molecule, such that electron transition between the HOMO and the LUMO occurs by a through-space interaction in the molecule, and the π-conjugated compound has a π-conjugated aromatic ring at a moiety on which at least one of the HOMO and the LUMO is localized,
wherein the π-conjugated compound is at least one of compounds having structures represented by General formulae (1), (2), (3), and (5):

General formula (1)

$$\begin{array}{c} R_{11} \quad R_{12} \quad R_{13} \quad R_{14} \\ R_{15} \underset{R_{16}}{\underset{R_{17}}{\bigvee}} \underset{N}{\overset{}{\bigvee}} \underset{R_{20}}{\overset{}{\bigvee}} R_{18} \\ R_{19} \end{array}$$

where $R_{11}$, $R_{12}$, $R_{13}$, $R_{14}$, $R_{15}$, $R_{16}$, $R_{17}$, $R_{18}$, $R_{19}$, and $R_{20}$ each independently represent a hydrogen atom or a substituent, and at least one of $R_{11}$, $R_{12}$, $R_{13}$, and $R_{14}$ is represented by General formula (1-A):

General formula (1-A)

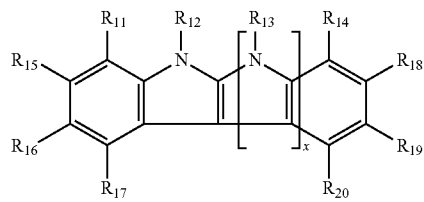

-continued

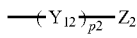 General formula (1-B)

where $Y_{11}$ represents a divalent linkage group, $Z_1$ represents an electron-donating aromatic hydrocarbon or heteroaromatic group, at least one of $R_{11}$, $R_{12}$, $R_{13}$, and $R_{14}$ is represented by General formula (1-B) where $Y_{12}$ represents a divalent linkage group and $Z_2$ represents an electron-accepting aromatic hydrocarbon or heteroaromatic group, x represents an integer of 1, and p1 and p2 each represent an integer of 0 or 1;

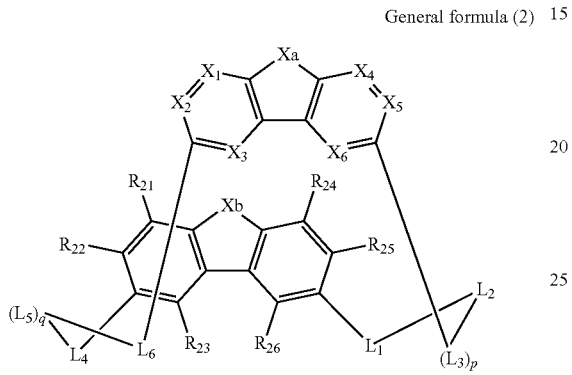 General formula (2)

where $X_a$ and $X_b$ each independently represent an oxygen atom, a sulfur atom, or $NR_c$, $X_1$, $X_2$, $X_3$, $X_4$, $X_5$, and $X_6$ each independently represent a nitrogen atom or $CR_d$ and at least one of $X_1$, $X_2$, $X_3$, $X_4$, $X_5$, and $X_6$ is a nitrogen atom, $R_c$, $R_d$, $R_{21}$, $R_{22}$, $R_{23}$, $R_{24}$, $R_{25}$, and $R_{26}$ each independently represent a hydrogen atom or a substituent, $L_1$, $L_2$, $L_3$, $L_4$, $L_5$, and $L_6$ each represent a divalent linkage group, and p and q each represent an integer of 0 or 1;

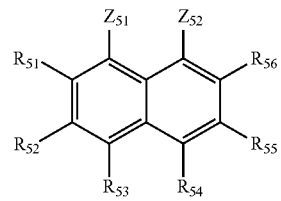 General formula (3)

where $X_{31}$ represents $PR_b$ (=O), $SO_2$, or SO, $R_b$, $R_{31}$, $R_{32}$, $R_{33}$, $R_{34}$, $R_{35}$, $R_{36}$, $R_{37}$, and $R_{38}$ each independently represent a hydrogen atom or a substituent, and at least one of $R_{31}$, $R_{33}$, $R_{36}$, and $R_{38}$ is represented by General formula (3-A):

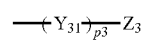 General formula (3-A)

where $Y_{31}$ represents a divalent linkage group, $Z_3$ represents an electron-donating aromatic hydrocarbon or heteroaromatic group, and p3 represents an integer of 0 or 1; and

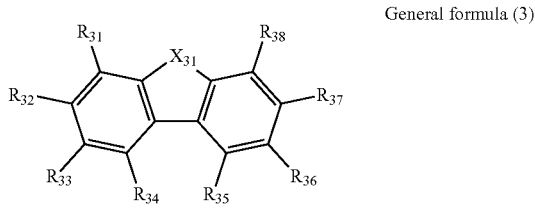 General formula (5)

where $R_{51}$, $R_{52}$, $R_{53}$, $R_{54}$, $R_{55}$, and $R_{56}$ each independently represent a hydrogen atom or a substituent, and $Z_{51}$ and $Z_{52}$ each independently represent an electron-donating aromatic hydrocarbon or heteroaromatic group or an electron-accepting aromatic hydrocarbon or heteroaromatic group, with the proviso that both $Z_{51}$ and $Z_{52}$ are not an electron-donating aromatic hydrocarbon or heteroaromatic group and that both $Z_{51}$ and $Z_{52}$ are not an electron-accepting aromatic hydrocarbon or heteroaromatic group.

2. The organic electroluminescent device according to claim 1, wherein the π-conjugated compound exhibits a ΔEst of 0.5 eV or less where ΔEst represents the absolute value of the difference between the lowest excited singlet energy level and the lowest excited triplet energy level.

3. The organic electroluminescent device according to claim 1, wherein the luminous layer comprises the π-conjugated compound and at least one of a fluorescent compound and a phosphorescent compound.

4. The organic electroluminescent device according to claim 1, wherein the luminous layer comprises the π-conjugated compound, at least one of a fluorescent compound and a phosphorescent compound, and a host compound.

5. A display apparatus comprising the organic electroluminescent device according to claim 1.

6. A lighting apparatus comprising the organic electroluminescent device according to claim 1.

* * * * *